(12) United States Patent
Brennan et al.

(10) Patent No.: US 9,016,221 B2
(45) Date of Patent: Apr. 28, 2015

(54) SURFACE TOPOGRAPHIES FOR NON-TOXIC BIOADHESION CONTROL

(75) Inventors: Anthony B. Brennan, Gainesville, FL (US); Christopher James Long, Titusville, FL (US); Joseph W. Bagan, Greenwood Village, CO (US); James Frederick Schumacher, Cumming, GA (US); Mark M. Spiecker, Denver, CO (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 646 days.

(21) Appl. No.: 12/550,870

(22) Filed: Aug. 31, 2009

(65) Prior Publication Data

US 2010/0226943 A1 Sep. 9, 2010

Related U.S. Application Data

(63) Continuation-in-part of application No. 11/567,103, filed on Dec. 5, 2006, now Pat. No. 7,650,848, which is a continuation-in-part of application No. 11/202,532, filed on Aug. 12, 2005, now Pat. No. 7,143,709, which is a continuation-in-part of application No. 10/780,424, filed on Feb. 17, 2004, now Pat. No. 7,117,807.

(51) Int. Cl.
*B63B 59/04* (2006.01)
*B08B 17/02* (2006.01)
(Continued)

(52) U.S. Cl.
CPC .............. *B08B 17/06* (2013.01); *Y02T 70/123* (2013.01); *A61F 2002/009* (2013.01);
(Continued)

(58) Field of Classification Search
CPC ........ B63B 1/36; B63B 59/04; Y02T 70/121; Y02T 70/123; B08B 17/06; B08B 17/065; B81C 1/00023; B81C 1/00031; B81C 1/00047; B81C 1/00055; B81C 1/00063; B81C 1/00071; A61F 2/0077; A61F 2/12; A61F 2/24; A61F 2002/0086; A61F 2002/009; A41D 31/0077; B64D 15/00; A61L 2/02; F05C 2253/12
USPC ........... 114/67 A, 222, 67 R; 405/216; 422/6; 428/141–145; 244/200, 200.1, 204, 244/204.1, 130; 424/400; 473/378–385; 623/23.5, 23.74
See application file for complete search history.

(56) References Cited

U.S. PATENT DOCUMENTS 3,243,850 A 4/1966 Zieg
3,351,441 A 11/1967 Gewiss et al.
(Continued)

FOREIGN PATENT DOCUMENTS

CA 2368204 10/2000
DE 3801139 C1 3/1989
(Continued)

OTHER PUBLICATIONS

Machine translation of JP 05-010309 A.*
(Continued)

*Primary Examiner* — Ajay Vasudeva
(74) *Attorney, Agent, or Firm* — Cantor Colburn LLP

(57) ABSTRACT

Disclosed herein is an article that includes a first plurality of spaced features. The spaced features are arranged in a plurality of groupings; the groupings of features include repeat units; the spaced features within a grouping are spaced apart at an average distance of about 1 nanometer to about 500 micrometers; each feature having a surface that is substantially parallel to a surface on a neighboring feature; each feature being separated from its neighboring feature; the groupings of features being arranged with respect to one another so as to define a tortuous pathway. The plurality of spaced features provide the article with an engineered roughness index of about 5 to about 20.

48 Claims, 15 Drawing Sheets

(51) Int. Cl.
| | |
|---|---|
| *B08B 17/06* | (2006.01) |
| *A61F 2/02* | (2006.01) |
| *A61L 27/00* | (2006.01) |
| *A41D 31/00* | (2006.01) |
| *A61L 2/02* | (2006.01) |
| *B64D 15/00* | (2006.01) |
| *A61F 2/00* | (2006.01) |
| *A61F 2/12* | (2006.01) |
| *A61F 2/24* | (2006.01) |
| *B63B 1/36* | (2006.01) |

(52) U.S. Cl.
CPC .... *A61F 2002/0086* (2013.01); *A41D 31/0077* (2013.01); *A61F 2/0077* (2013.01); *A61F 2/12* (2013.01); *A61F 2/24* (2013.01); *A61L 2/02* (2013.01); *B08B 17/065* (2013.01); *B63B 1/36* (2013.01); *B63B 59/04* (2013.01); *B64D 15/00* (2013.01); *F05C 2253/12* (2013.01); *Y02T 70/121* (2013.01)

(56) References Cited

U.S. PATENT DOCUMENTS

| | | | | |
|---|---|---|---|---|
| 3,354,022 | A | * | 11/1967 | Johnson, Jr. et al. ......... 428/167 |
| 3,795,471 | A | | 3/1974 | Milani |
| 3,935,485 | A | | 1/1976 | Yoshida et al. |
| 3,971,084 | A | | 7/1976 | Spier |
| 3,992,162 | A | | 11/1976 | Gewiss |
| 3,996,323 | A | | 12/1976 | Hegler et al. |
| 4,101,625 | A | | 7/1978 | Haley |
| 4,283,461 | A | | 8/1981 | Wooden et al. |
| 4,284,689 | A | * | 8/1981 | Craighead et al. ............ 428/620 |
| 4,297,394 | A | | 10/1981 | Wooden et al. |
| 4,640,859 | A | | 2/1987 | Hansen et al. |
| 4,865,603 | A | * | 9/1989 | Noiles ........................... 623/23.5 |
| 5,008,140 | A | | 4/1991 | Schmertz |
| 5,028,474 | A | | 7/1991 | Czaplicki |
| 5,328,200 | A | * | 7/1994 | Pelizzari ....................... 280/609 |
| 5,344,691 | A | | 9/1994 | Hanschen et al. |
| 5,403,680 | A | | 4/1995 | Otagawa et al. |
| 5,645,764 | A | | 7/1997 | Angelopoulos et al. |
| 5,650,214 | A | | 7/1997 | Anderson et al. |
| 5,842,937 | A | * | 12/1998 | Dalton et al. .................. 473/384 |
| 5,971,326 | A | | 10/1999 | Bechert |
| 5,976,284 | A | | 11/1999 | Calvert et al. |
| 6,010,442 | A | * | 1/2000 | Lemons et al. ................ 473/384 |
| 6,075,585 | A | | 6/2000 | Minne et al. |
| D430,734 | S | | 9/2000 | Bredendick et al. |
| D436,738 | S | | 1/2001 | Bredendick et al. |
| D440,051 | S | | 4/2001 | Bredendick et al. |
| 6,231,463 | B1 | * | 5/2001 | Tavares et al. ................. 473/378 |
| D443,766 | S | | 6/2001 | Bredendick et al. |
| 6,394,652 | B2 | | 5/2002 | Meyer et al. |
| D459,897 | S | | 7/2002 | Bredendick et al. |
| 6,458,447 | B1 | | 10/2002 | Cabell et al. |
| 6,569,038 | B2 | * | 5/2003 | Sullivan ........................ 473/383 |
| 6,616,882 | B1 | | 9/2003 | Lidgett |
| 6,660,363 | B1 | | 12/2003 | Barthlott |
| 6,686,026 | B2 | | 2/2004 | Spiewak et al. |
| 6,911,243 | B2 | | 6/2005 | Sher et al. |
| 6,946,170 | B2 | * | 9/2005 | Gerber et al. ................... 428/13 |
| D518,648 | S | | 4/2006 | Broering et al. |
| 7,117,536 | B2 | | 10/2006 | Burnett et al. |
| 7,117,807 | B2 | * | 10/2006 | Bohn, Jr. et al. .............. 114/222 |
| 7,143,709 | B2 | * | 12/2006 | Brennan et al. ............... 114/222 |
| 7,303,491 | B2 | * | 12/2007 | Nardacci et al. .............. 473/378 |
| 7,650,848 | B2 | * | 1/2010 | Brennan et al. ............... 114/222 |
| 7,691,464 | B2 | * | 4/2010 | Gerber et al. ................... 428/99 |
| 2002/0150724 | A1 | | 10/2002 | Nun et al. |
| 2003/0228445 | A1 | | 12/2003 | Vaughn et al. |
| 2004/0086674 | A1 | | 5/2004 | Holman |
| 2004/0191538 | A1 | | 9/2004 | Huang |
| 2005/0003146 | A1 | * | 1/2005 | Spath ............................ 428/105 |
| 2005/0008828 | A1 | | 1/2005 | Libera et al. |
| 2005/0119723 | A1 | * | 6/2005 | Peacock, III ................. 623/1.15 |
| 2005/0119758 | A1 | * | 6/2005 | Alexander et al. ........... 623/23.5 |
| 2005/0136217 | A1 | * | 6/2005 | Barthlott et al. .............. 428/141 |
| 2005/0178286 | A1 | | 8/2005 | Bohn, Jr. et al. |
| 2006/0219143 | A1 | | 10/2006 | Brennan et al. |
| 2007/0098957 | A1 | | 5/2007 | Barthlott et al. |
| 2007/0227428 | A1 | | 10/2007 | Brennan |
| 2008/0202370 | A1 | | 8/2008 | Muraoka |
| 2010/0033818 | A1 | | 2/2010 | Petcavich |
| 2010/0119755 | A1 | | 5/2010 | Chung |
| 2010/0226943 | A1 | | 9/2010 | Brennan |

FOREIGN PATENT DOCUMENTS

| | | | | |
|---|---|---|---|---|
| DE | 19613304 | A1 | * 10/1997 | |
| DE | 19840303 | A1 | * 3/2000 | ............... F15D 1/12 |
| EP | 0015312 | A1 | 9/1980 | |
| EP | 1469198 | A1 | * 10/2004 | ............... F03D 1/06 |
| GB | 722591 | | 1/1955 | |
| JP | 05010309 | A | * 1/1993 | ............... F15D 1/10 |
| JP | 2001207123 | A | * 7/2001 | ........... C09D 185/00 |
| WO | WO9302517 | | 12/1993 | |
| WO | wo9604123 | | 2/1996 | |
| WO | WO0058410 | | 10/2000 | |
| WO | WO2006026993 | | 3/2006 | |
| WO | WO2008070625 | | 6/2008 | |

OTHER PUBLICATIONS

Machine translation of JP 05-010309 A (Undated).*
J.M. Hills, et al. "Settlement of Barnacle Larvae is Governed by Euclidean and not Fractal Surface Characteristics" Functional Ecology (1999), pp. 868-875, vol. 13, British Ecological Society.
J. Bico, et al. "Pearl Drops" Europhysics Letters (Jul. 15, 1999) pp. 220-226; vol. 47 (2); EDP Sciences.
D.W. Bechert, et al. "Fluid Mechanics of Biological Surfaces and their Technological Application", Naturwissenschaften (2000) pp. 157-171; vol. 87; Springer-Verlag, Germany.
M.E. Callow, et al. "Microtopographic Cues for Settlement of Zoospores of the Green Fouling Alga *Enteromorpha*", Biofouling (2002) pp. 237-245; vol. 18 (3); Taylor & Francis, UK.
H.C. Flemming, "Biofouling in Water Systems—Cases, Causes and Countermeasures", Appl. Microbiol Biotechnol (2002), pp. 629-640, vol. 59; Springer-Verlag, Germany.
J. Bico, et al. "Wetting of Textured Surfaces", Colliods and Surfaces (2002) pp. 41-46, vol. 206; Elsevier Science B.V.
B. He, et al. "Multiple Equilibrium Droplet Shapes and Design Criterion for Rough Hydrophobic Surfaces", Langmuir (2003) pp. 4999-5003, vol. 19; American Chemical Society.
Y. Chen, et al. "Anisotropy in the Wetting of Rough Surfaces", Journal of Colloid and Interface Sciences (2005), pp. 458-464, vol. 281; Elsevier Inc.
R. Furstner, et al. "Wetting and Self-Cleaning Properties of Artificial Superhydrophobic Surfaces", Langmuir (2005), pp. 956-961, vol. 21; American Chemical Society.
W.R. Hansen, et al. "Evidence for Self-Cleaning in Gecko Setae" Evolution (Jan. 11, 2005) pp. 385-389, vol. 102 vol. 2; PNAS.
M.E. Abdelsalam, et al. "Wetting of Regularly Structured Gold Surfaces" Langmuir (2005) pp. 1753-1757, vol. 21, American Chemical Society.
Z. Burton, et al. "Hydrophobicity, Adhesion, and Friction Properties of Nanopatterned Polymers and Scale Dependence for Micro- and Nanoelectromechanical Systems" Nano Letters (2005) pp. 1607-1613, vol. 5 No. 8, American Chemical Society.
E. Martines, et al. "Superhydrophobicity and Superhydrophilicity of Regular Nanopatterns" Nano Letters (2005) pp. 2097-2103, vol. 5, No. 10, American Chemical Society.
G.McHale, et al. "Analysis of Droplet Evaporation on a Superhydrophobic Surface" Langmuir (2005) pp. 11053-11060, vol. 21, American Chemical Society.
L.D. Chambers, et al. "Modern Approaches to Marine Antifouling Coatings" Surface and Coatings Technology (2006) pp. 3642-3652, vol. 201, Elsevier B.V.

(56) References Cited

OTHER PUBLICATIONS

J. Genzer, et al. "Recent Developments in Superhydrophobic Surfaces and their Relevance to Marine Fouling: A Review" Biofouling (2006) pp. 1-22, Taylor & Francis.
A. Tuteja, et al. "Designing Superoleophobic Surfaces" Science (Dec. 7, 2007) pp. 1618-1622, ScienceMag.org.
D. Quere "Wetting and Roughness" Annu. Rev. Mater. Res. (2008) pp. 71-99 vol. 38, Annual Reviews.
D.M. Spori, et al. "Beyond the Lotus Effect: Roughness Influences on Wetting Over a Wide Surface-Energy Range" Langmuir (2008) pp. 5411-5417, vol. 24, American Chemical Society.
International Search Report dated May 22, 2008 for App # PCT/US07/86289.
Callow et al. "Primary adhesion of enteromorphia (chlorophyta, ulvales) propagules: quantitative settlement studies and video microscopy", J. Phycol., 1997, vol. 33 pp. 938-947.
Cassie et al. "Wettability of porous surfaces", Trans. Faraday Society, 1944, vol. 40, pp. 546-551.
Fractals Are Smart: Fractal Pack 1 Educators' Guide. Downloaded from the FractalFoundation.org. Copyright 2009.
Horiuchi et al. "Optical lithography onto inside surfaces of small-diameter pipes" Microelectronic Engineering 85 (2008) 1043-1046—Elsevier.
International Search Report dated Jun. 13, 2006 for Application No. PCT/US05/04972—4 pages.
Quere "Rough ideas on wetting", Physica A, 2002 vol. 313, pp. 32-46.
Search Report dated Jun. 25, 2010 for Application No. PCT/US09/064160—8 pages.
Wenzel "Resistance of solid surfaces to wetting by water", Industrial and Engineering Chemistry, 1936, vol. 28, No. 8, pp. 988-994.
Written Opinion dated Jun. 13, 2006 for Application No. PCT/US05/04972—6 pages.
Written Opinion dated May 22, 2008 for Application No. PCT/US07/86289—6 pages.
Written Opinion dated Jun. 25, 2010 for Application No. PCT/US09/064160—6 pages.
Xia et al. "Soft Lithography", Annu. Rev. Mater. Sci., 1998, vol. 28, pp. 153-184.
Patent Abstract of Japan; Publication No. 10-123693; May 15, 1998 (1 page).
Patent Abstracts of Japan; 62-046232 dated Feb. 28, 1987—(1 page).
European Search Report for Appl. 12172148.4 dated Nov. 23, 2012, 13 pages.

* cited by examiner

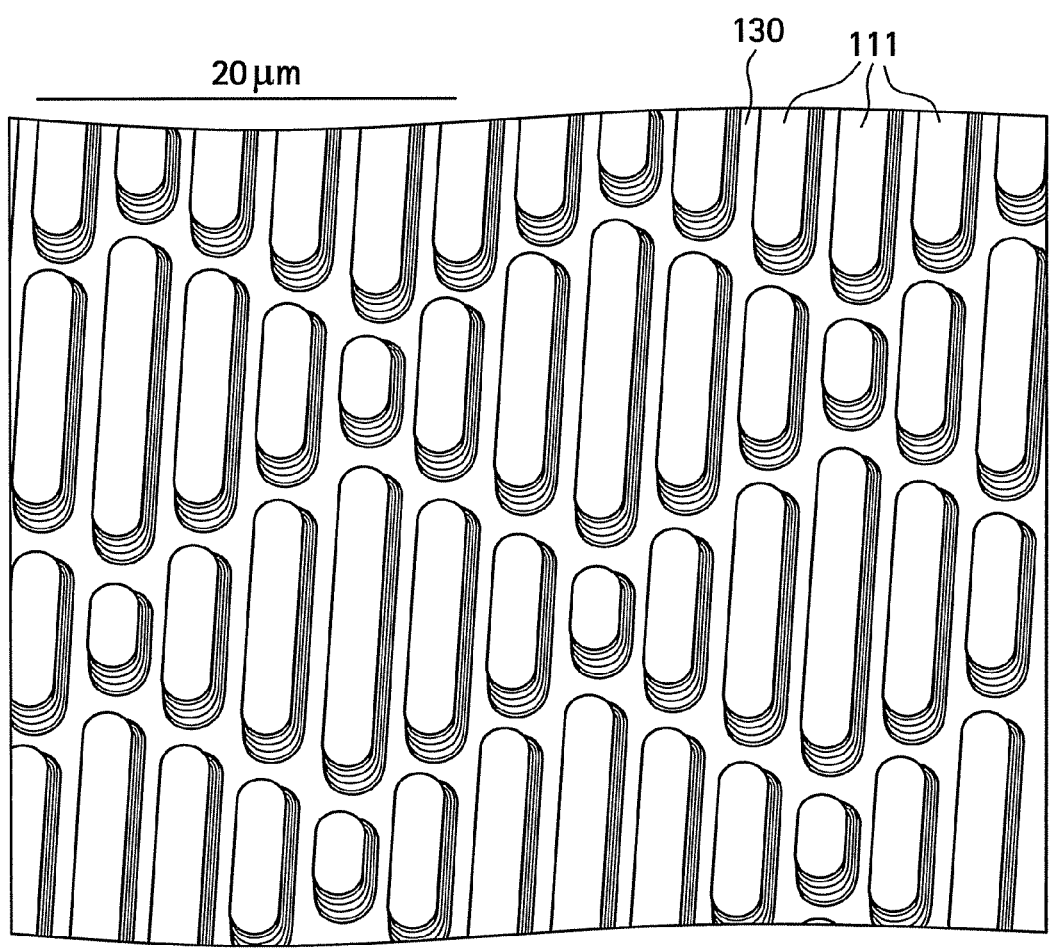

FIG. 3

| | Depth (um) | Spacing (um) | Width (um) | Roughness Factor |
|---|---|---|---|---|
| Riblet | 5 | 2 | 2 | 5.0 |
| | 8 | 2 | 2 | 7.3 |
| | 10 | 2 | 2 | 8.9 |
| Star/Clover | 5 | 2 | 4 | 4.5 |
| | 8 | 2 | 4 | 6.6 |
| | 10 | 2 | 4 | 8.0 |
| | 5 | 2 | 2,4 | 3.6 |
| | 8 | 2 | 2,4 | 5.2 |
| | 10 | 2 | 2,4 | 6.2 |
| Gradient | 5 | 1,2,3,4 | 2 | 2.8 |
| | 8 | 1,2,3,4 | 2 | 3.8 |
| | 10 | 1,2,3,4 | 2 | 4.5 |
| Triangle/Circle | 5 | 1 | 1,5 | 7.5 |
| | 5 | 2 | 2,10 | 4.2 |
| | 5 | 3 | 3,15 | 3.2 |
| | 8 | 1 | 1,5 | 11.3 |
| | 8 | 2 | 2,10 | 6.2 |
| | 8 | 3 | 3,15 | 4.4 |
| | 10 | 1 | 1,5 | 13.9 |
| | 10 | 2 | 2,10 | 7.5 |
| | 10 | 3 | 3,15 | 5.3 |

100 μm

Ulva Settlement vs ERI
Gradient Studies

SURFACE TOPOGRAPHIES FOR NON-TOXIC BIOADHESION CONTROL

CROSS-REFERENCE TO RELATED APPLICATIONS

This application is a continuation-in-part (CIP) application of U.S. patent application Ser. No. 11/567,103, now U.S. Pat. No. 7,650,848, which is a continuation-in-part (CIP) application of U.S. patent application Ser. No. 11/202,532 entitled "SURFACE TOPOGRAPHY FOR NON-TOXIC BIOADHESION CONTROL" which was filed on Aug. 12, 2005, now U.S. Pat. No. 7,143,709, which is a CIP of U.S. patent application Ser. No. 10/780,424 entitled "DYNAMICALLY MODIFIABLE POLYMER COATINGS AND DEVICES" which was filed on Feb. 17, 2004, now U.S. Pat. No. 7,117,807, each of which are incorporated by reference in their entirety into the present application.

STATEMENT REGARDING FEDERALLY SPONSORED RESEARCH OR DEVELOPMENT

The United States Government has rights in this invention pursuant to Office of Naval Research (ONR) Grant No. N00014-02-1-0325

FIELD OF THE INVENTION

The invention relates to articles and related devices and systems having surface topography and/or surface elastic properties for providing non-toxic bioadhesion control.

BACKGROUND

Biofouling is the unwanted accumulation of organic and inorganic matter of biological origin on surfaces. For example, in the marine environment bio fouling is the result of marine organisms settling, attaching, and growing on submerged marine surfaces. The bio fouling process is initiated within minutes of a surface being submerged in a marine environment by the absorption of dissolved organic materials which result in the formation of a conditioning film. Once the conditioning film is deposited, bacteria (e.g. unicellular algae) colonize the surface within hours of submersion. The resulting biofilm produced from the colonization of the bacteria is referred to as microfouling or slime and can reach thicknesses on the order of 500 μm.

Biofouling is estimated to cost the U.S. Navy alone over $1 billion per year by increasing the hydrodynamic drag of naval vessels. This in turn decreases the range, speed, and maneuverability of naval vessels and increases the fuel consumption by up to 30-40%. Thus, biofouling weakens the national defense. Moreover, biofouling is also a major economical burden on commercial shipping, recreational craft, as well as civil structures, bridges, and power generating facilities.

Any substrate in regular contact with water is likely to become fouled. No surface has been found that is completely resistant to fouling. Due to the vast variety of marine organisms that form biofilms, the development of a single surface coating with fixed surface properties for the prevention biofilm formation for all relevant marine organisms is a difficult if not impossible task.

Anti-fouling and foul-release coatings are two main approaches currently used for combating biofilm formation. Anti-fouling coatings prevent or deter the settling of biofouling organisms on a surface by the use of leached biocides, typically cuprous oxide or tributyltin, into the water. The biocides are either tethered to the coated surface or are released from the surface into the surrounding environment. Use of these types of coatings has caused damage to the marine ecosystem, especially in shallow bays and harbors, where the biocides can accumulate. As such, the use of tributyltin has been banned in many parts of the world. These products are effective for only approximately 2 to 5 years.

Foul release coatings present a hydrophobic, low surface energy, and resulting slippery surface that minimizes the adhesion of the biofouling organisms. The most commonly used and highly successful of these is a nontoxic silicone-based paint. The silicone-based coating requires several layers to make it effective, and therefore it can be quite costly. Effectiveness lasts up to 5 years at which time recoating may become necessary. These products are considered to be more environmentally sound as compared to anti-fouling coatings because they do not leach toxins. However, they are subject to abrasion, and therefore their use is limited to areas that are not susceptible to damage caused by ice or debris.

Biofouling is similarly a problem for surfaces used in biomedical applications. The accumulations of bacteria, i.e. a biofilm, on implanted devices such as orthopedic prostheses present a significant risk of infection leading to complications as severe as death. In cosmetic implants, devices such as breast implants are fouled with fibroblasts and acellular extracellular matrix resulting in a hard fibrous capsule and subsequent implant rupture. Blood contacting surfaces such as artificial heart valves and artificial vascular grafts are fouled by proteins such as fibrinogen that initiate the coagulation cascade leading in part to heart attack and stroke. The accumulated affect of bio fouling on chronic and acute disease states, its contribution to morbidity and its massive medical expenses places biofouling as one of the major issues facing modern medicine.

SUMMARY OF THE INVENTION

An article has a surface topography for resisting bioadhesion of organisms and includes a base article having a surface. The chemical composition of the surface comprises a polymer. The surface has a topography comprising a pattern defined by a plurality of spaced apart features attached to or projected into the base article. The plurality of features each have at least one microscale dimension and at least one neighboring feature having a substantially different geometry. An average spacing between adjacent ones of the features is between 10 μm and 100 μm in at least a portion of the surface.

Surface topographies according to the invention resist bioadhesion as compared to the base article. As used herein, a surface that provides a surface topography according to the invention can be applied to a surface as either a printed patterned, adhesive coating containing the topography, or applied directly to the surface of the device through micromolding. In the case of micromolding, the surface topography will be monolithically integrated with the underlying article.

The feature spacing distance as used herein refers to the distance between adjacent features. Moreover, as used herein, "microscale features" includes micron size or smaller features, thus including microscale and nanoscale.

In one embodiment of the invention referred to as a hierarchical architecture, at least one multi-element plateau layer is disposed on a portion of the surface. A spacing distance between elements of the plateau layer provides a second feature spacing being substantially different as compared to the first feature spacing. The hierarchical architecture can simultaneously repel organisms having substantial different sizes, such as spores and barnacles. In one embodiment the surface is monolithically integrated with the base article, wherein a composition of the base article is the same as the composition of the surface. In another embodiment, the surface comprises a coating layer disposed on the base article. In this coating embodiment, the composition of the coating layer is different as compared to a composition of the base article, and the polymer can comprise a non-electrically conductive polymer, such as selected from elastomers, rubbers, polyurethanes and polysulfones.

The topography can provide an average roughness factor (R) of from 4 to 50 and an elastic modulus of between 10 kPa and 10 MPa. In another embodiment, the topography is numerically representable using at least one sinusoidal function, such as two different sinusoidal waves. An example of a two different sinusoidal wave topography comprises a Sharklet topography. In another embodiment, the plurality of spaced apart features can have a substantially planar top surface. In a preferred embodiment for controlling barnacles, the first feature spacing can be between 15 and 60 µm.

In the multi-element plateau layer disposed on a portion of surface embodiment, wherein a spacing distance between elements of the plateau layer provide a second feature spacing being substantially different as compared to the first feature spacing, the surface can comprise a coating layer disposed on the base article. The elastic modulus of the coating layer can be between 10 kPa and 10 MPa.

The base article can comprise a roofing material. In another embodiment, the base article comprises a water pipe, wherein the surface is provided on an inner surface of a water inlet pipe. In this embodiment, the inlet pipe can be within a power plant in another embodiment, the base article comprises an implantable device or material, such as a breast implant, a catheter or a heart valve.

In another embodiment of the invention, an article has a surface topography for resisting bioadhesion of organisms, comprising a base article having a surface. The composition of the surface comprises a polymer, the surface having a topography comprising a pattern defined by a plurality of spaced apart features attached to or projected into the base article. The plurality of features each have at least one microscale dimension and at least one neighboring feature having a substantially different geometry, wherein an average first feature spacing between adjacent ones of the features is microscale and topography is numerically representable using at least one sinusoidal function. The surface can comprise a coating layer disposed on the base article. In a first embodiment the first feature spacing is between 0.5 and 5 µm in at least a portion of the surface, while in a second embodiment the first feature spacing is between 15 and 60 µm in at least a portion of the surface. The at least one sinusoidal function can comprise two different sinusoidal waves, such as a Sharklet topography. The article can further comprise at least one multi-element plateau layer disposed on a portion of the surface, wherein a spacing distance between elements of the plateau layer provide a second feature spacing being substantially different as compared to the first feature spacing.

Disclosed herein is an article comprising a plurality of spaced features; the spaced features arranged in a plurality of groupings; the groupings of features comprising repeat units; the spaced features within a grouping being spaced apart at an average distance of about 1 nanometer to about 500 micrometers; each feature having a surface that is substantially parallel to a surface on a neighboring feature; each feature being separated from its neighboring feature; the groupings of features being arranged with respect to one another so as to define a tortuous pathway.

Disclosed herein too is an article comprising a plurality of spaced features; the features arranged in a plurality of groupings; the groupings of features comprising repeat units; the spaced features within a grouping being spaced apart at an average distance of about 1 nanometer to about 500 micrometers; the groupings of features being arranged with respect to one another so as to define a tortuous pathway and wherein a tangent to the tortuous pathway intersects with a spaced feature; the spaced feature being different from each nearest neighbor and not in contact with the nearest neighbor.

BRIEF DESCRIPTION OF THE DRAWINGS

A fuller understanding of the present invention and the features and benefits thereof will be obtained upon review of the following detailed description together with the accompanying drawings, in which:

FIG. 1(a) is a scanned SEM image of an exemplary "Sharklet" anti-algae surface topography comprising a plurality of raised surface features which project out from the surface of a base article, according to an embodiment of the invention.

FIG. 3 provides a table of exemplary feature depths, feature spacings, feature widths and the resulting roughness factor (R) based on the patterns shown in FIGS. 2(a)-(d).

FIG. 7(b) shows the result of applying sinusoidal waves to define aperiodic structures, while

FIG. 8(b) is a scanned light micrograph image showing algae spores on the surface of the control sample, while

FIG. 11(*b*) is a chart of barnacle cyprid settlement for a second assay (assay 2). Cyprids were allowed to settle for up to 72 hrs on each of the test surfaces. Topographies used included 20×20 channels (20CH), 20×20 Sharklet (20SK), 40×40 channels (40CH) and 40×40 Sharklet (40SK). Error bars represent ±1 standard error.

FIG. 11(*c*) is a chart of barnacle cyprid settlement for a third assay (assay 3). Cyprids were allowed to settle for up to 48 hrs on each of the test surfaces. Topographies used included 20×20 channels (20CH), 20×20 Sharklet (20SK), 40×40 channels (40CH) and 40×40 Sharklet (40SK). Error bars represent ±1 standard error.

FIG. 14 depicts how the degrees of freedom are calculated.

DETAILED DESCRIPTION OF THE INVENTION

Figure 1B:
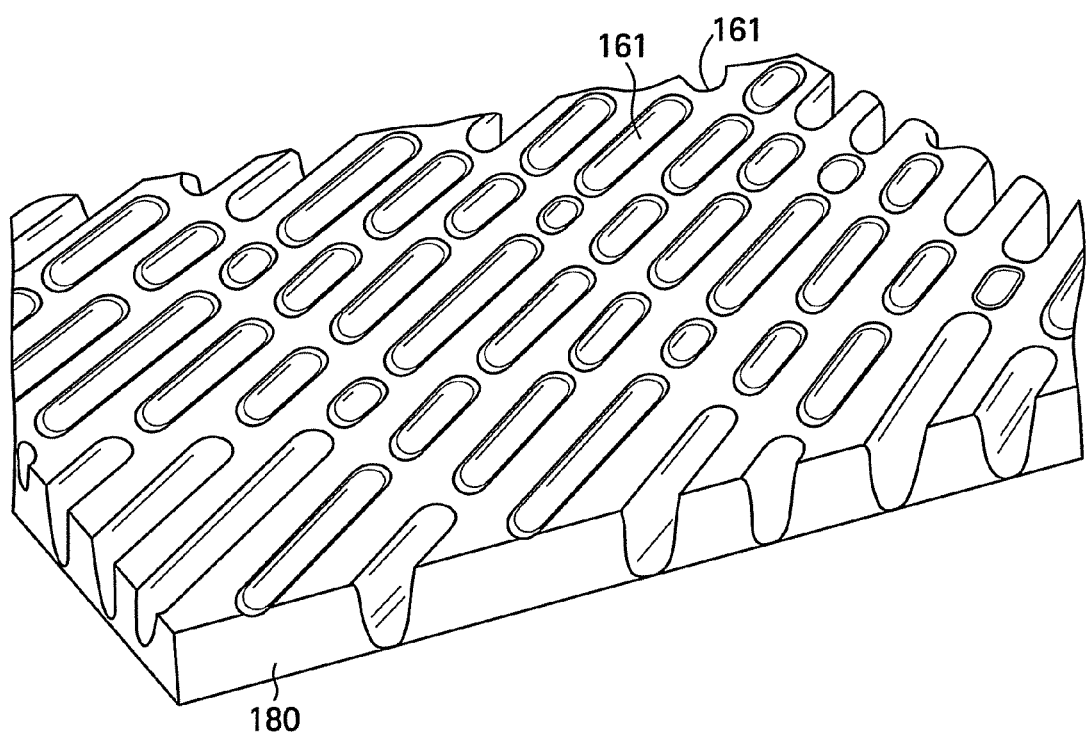
FIG. 1(b) is a scanned optical profilometry image of a pattern having a plurality of features projecting into the surface of a base article, according to another embodiment of the invention.

The present invention describes a variety of scalable surface topographies for modification of biosettlement and bioadhesion, such as bioadhesion of biofouling organisms, including, but not limited to, algae, bacteria and barnacles. As described in the Examples below, it has been proven through experimental testing that surface topographies according to the invention provide a passive and non-toxic surface, which through selection of appropriate feature sizes and spacing, can significantly and generally dramatically reduce settlement and adhesion of the most common fouling marine algae known, as well as the settlement of barnacles. In one embodiment, the plurality of spaced features increase the effectiveness of algaecides or antibiotics. The algaecides and/or antibiotics can be contained in the surface and can be released gradually when desired.

Disclosed herein are articles comprising a plurality of spaced features; the features arranged in a plurality of groupings; the groupings of features being arranged with respect to one another so as to define a tortuous pathway when viewed in a first direction. When viewed in a second direction, the groupings of features are arranged to define a linear pathway.

In one embodiment, when viewed in a second direction, the pathway between the features may be non-linear and non-sinusoidal. In other words, the pathway can be non-linear and aperiodic. In another embodiment, the pathway between the features may be linear but of a varying thickness. The plurality of spaced features may be projected outwards from a surface or projected into the surface. In one embodiment, the plurality of spaced features may have the same chemical composition as the surface. In another embodiment, the plurality of spaced features may have a different chemical composition from the surface.

In one embodiment, an article having a surface topography for resisting bioadhesion of organisms, comprises a base article having a surface. The composition of the surface and/or the base article comprises a polymer, a metal or an alloy, a ceramic. Combinations of polymers, metals and ceramics may also be used in the surface or the base article. The surface having a topography comprising a plurality of patterns; each pattern being defined by a plurality of spaced apart features attached to or projected into the base article. The plurality of features each have at least one microscale (micrometer or nanometer sized) dimension and has at least one neighboring feature having a substantially different geometry. The average first feature spacing between the adjacent features is between 10 µm and 100 µm in at least a portion of the surface, wherein said plurality of spaced apart features are represented by a periodic function. It is to be noted that each of the features of the plurality of features are separated from each other and do not contact one another.

In one embodiment, the surface is monolithically integrated with said base article, wherein a composition of the base article is the same as the composition of the surface. In another embodiment, the surface comprises a coating layer disposed on the base article. In yet another embodiment, the composition of the coating layer is different from the composition of the base article. In one embodiment, the polymer comprises a non-electrically conducting polymer.

In another embodiment, the topography provides an average roughness factor (R) of from 4 to 50. The surface may comprise an elastomer that has an elastic modulus of about 10 kPa to about 10 MPa.

As noted above, the pattern is separated from a neighboring pattern by a tortuous pathway. The tortuous pathway may be represented by a periodic function. The periodic functions may be different for each tortuous pathway. In one embodiment, the patterns can be separated from one another by tortuous pathways that can be represented by two or more periodic functions. The periodic functions may comprise a sinusoidal wave. In an exemplary embodiment, the periodic function may comprise two or more sinusoidal waves.

In another embodiment, when a plurality of different tortuous pathways are represented by a plurality of periodic functions respectively, the respective periodic functions may be separated by a fixed phase difference. In yet another embodiment, when a plurality of different tortuous pathways are represented by a plurality of periodic functions respectively, the respective periodic functions may be separated by a variable phase difference.

In one embodiment, the plurality of spaced apart features have a substantially planar top surface. In another embodiment, a multi-element plateau layer can be disposed on a portion of the surface, wherein a spacing distance between elements of said plateau layer provide a second feature spacing; the second feature spacing being substantially different when compared to the first feature spacing.

In one embodiment, the pattern comprises a coating layer disposed on said base article. In other words, the coating layer comprises the pattern and is disposed on the base article.

In another embodiment, an article having a surface topography for controlling (e.g., resisting or facilitating) the bioadhesion of organisms, comprises a base article having a surface; wherein the composition of the surface comprises a polymer, a ceramic or a metal. The surface has a topography comprising a pattern defined by a plurality of spaced apart features attached to or projected into the base article. The plurality of features each have at least one microscale dimension and have at least one neighboring feature having a substantially different geometry. The features are separated from each other and the average feature spacing is about 1 nanometer to about 500 micrometers. The topography is numerically representable using at least one periodic function; the periodic function being representable by a pathway situated substantially between a plurality of patterns of the spaced apart features.

In one embodiment, the first feature spacing is between 0.5 micrometers (μm) and 5 μm in at least a portion of the surface. In another embodiment, the first feature spacing is between 15 and 60 μm in at least a portion of said surface. As noted above, the periodic function comprises two different sinusoidal waves. In one embodiment, the topography resembles the topography of shark-skin (e.g., a Sharklet). In another embodiment, the pattern comprises at least one multi-element plateau layer disposed on a portion of the surface, wherein a spacing distance between elements of the plateau layer provides a second feature spacing; the second feature spacing being substantially different when compared to said first feature spacing.

In yet another embodiment, an article having a surface topography for resisting bioadhesion of organisms, comprises a base article having a surface. The surface has a topography that comprises a pattern defined by a plurality of spaced apart features attached to or projected into the base article. The plurality of features comprise at least one feature having a substantially different geometry. The features are separated from each other. One of these features that is a part of the pattern is shared by a neighboring pattern. The plurality of spaced apart features has at least one microscale dimension. The neighboring patterns are separated from each other by a tortuous pathway. The tortuous pathway has at least two or more directions.

In another embodiment, an article comprises a plurality of spaced features. The features are arranged in a plurality of groupings; the groupings of features comprise repeat units. The spaced features within a grouping are spaced apart at an average distance of about 0.5 to about 200 micrometers. The groupings of features are arranged with respect to one another so as to define a tortuous pathway, the groupings have patterns of features wherein one or more features are shared between groupings. These are generally referred to as shared features. The plurality of spaced feature extend outwardly from a surface.

In one embodiment, a sum of a number of features shared by two neighboring groupings is equal to an odd number. In another embodiment, a sum of a number of features shared by two neighboring groupings is equal to an even number.

In one embodiment, the plurality of spaced features has a similar chemical composition to the surface. In another embodiment, the plurality of spaced features has a different chemical composition from that of the surface. In one embodiment, the features have similar geometries, while in another embodiment, the features can have different geometries. As will be detailed below, the groupings show dilational symmetry.

The plurality of spaced features is applied to the surface in the form of a coating and can comprise an organic polymer, a ceramic or a metal. As noted above, the groupings of features are arranged with respect to one another so as to define a linear pathway or a plurality of channels. The tortuous pathway is defined by a sinusoidal function.

In one embodiment, the features are periodic. In another embodiment, the features are aperiodic. The features have a roughness factor (R) of about 2 to about 20.

As can be seen in the FIGS. 1(a), 1(b), 2(a), 2(b), 2(c), 2(d), 5, 5(a), 7(a), 7(b) and 7(c), the article comprises a plurality of spaced features; the spaced features being arranged in a plurality of groupings. The FIGS. 1(a), 1(b), 2(a), 2(b), 2(c), 2(d), 5 (a), 5(b), 7(a), 7(b) and 7(c) show that the groupings of features comprise at least some repeat units. As can be seen in these Figures, the groupings have patterns of features. As can also be seen in these figures, the groupings of features are arranged with respect to one another so as to define a tortuous pathway when viewed in one direction and define linear pathways when viewed in other directions.

Figure 5A:
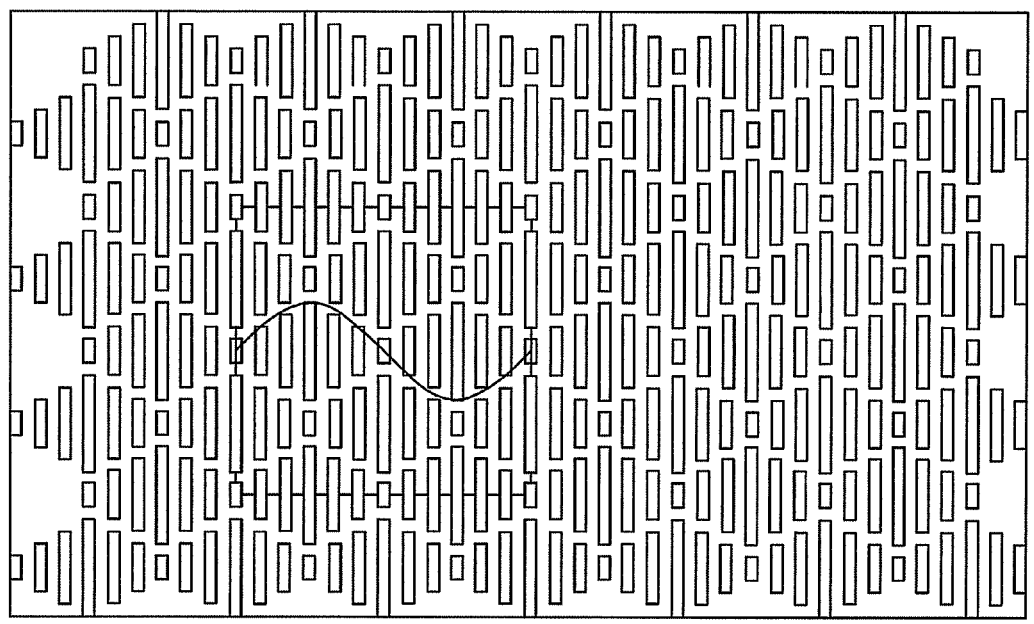
FIG. 5(a) shows a sinusoidal wave beginning at the centroid of the smallest (shortest) of the four features comprising the Sharklet pattern.
Figure 5B:
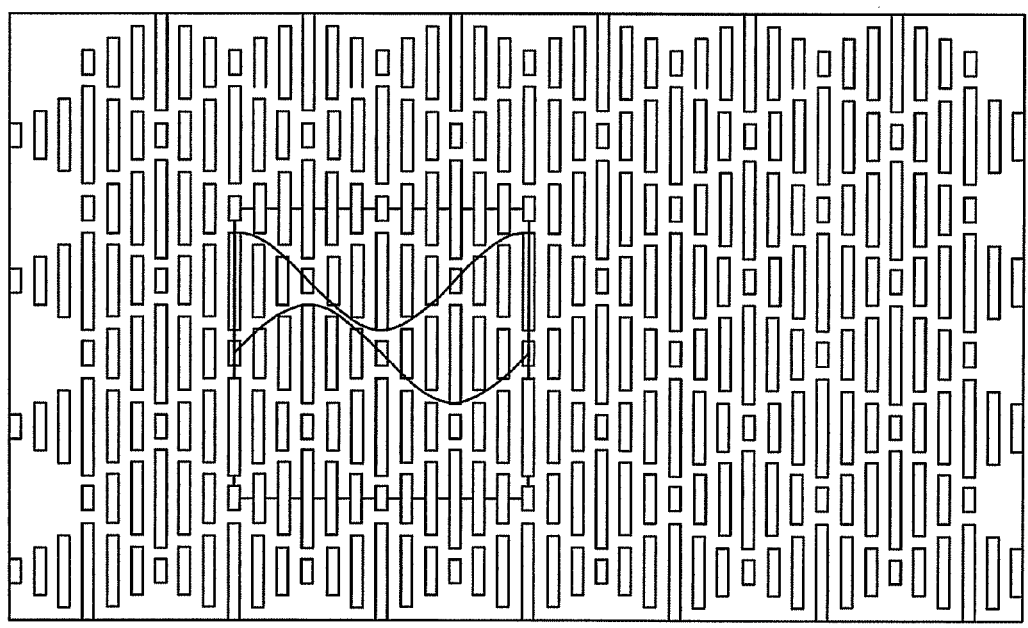
FIG. 5(b) shows sine and cosine waves describing the periodicity and packing of the Sharklet pattern.

As can be seen in the FIGS. 5(a) and 5(b), the tortuous pathway exists substantially between pluralities of groupings of such features. As can be seen in the FIG. 5(a), an occasional feature may lie in the otherwise tortuous pathway. In one embodiment, a tangent to the tortuous pathway will always intersect a single separated feature of the pattern. In one embodiment, a frequency of intersection between the tangent to the tortuous pathway and the spaced feature is periodic. In another embodiment, a frequency of intersection between a tangent to the tortuous pathway and a spaced feature is aperiodic. In another embodiment, a frequency of intersection between a tangent to the tortuous pathway and a shared feature is periodic. In another embodiment, a frequency of intersection between a tangent to the tortuous pathway and the shared spaced feature is aperiodic.

It is generally desirable for the groupings of features to comprise at least one repeat unit and to share at least one common feature. For example, in the FIGS. 1(a), 1(b), the groupings of feature have a repeat unit that has a diamond shape. It can also be seen that the smallest feature in each repeat unit is shared by two adjacent repeat units or by two adjacent groups of features. The sharing of the feature by two or more groups of patterns results in the formation of the tortuous pathway. Similarly the FIGS. 2(a) and 2(b) show at least one feature that is shared by two adjacent repeat units.

The number of features in a given pattern can be odd or even. In one embodiment, if the total number of features in a given pattern are equal to an odd number, then the number of shared features are generally equal to an odd number. In another embodiment, if the total number of features in a given pattern are equal to an even number, then the number of features in the given pattern are equal to an even number.

The spaced features can have variety of geometries and can exist in one, two or three dimensions or any dimensions therebetween. The spaced features can have similar geometries with different dimensions or can have different geometries with different dimensions. For example, in the FIG. 1(a), the spaced features are of a similar shape, with each shape having a different sizes, while in the FIGS. 7(a), 7(b) and 7(c), the spaced features have different geometries and different dimensions.

The geometries can be regular (e.g., described by Euclidean mathematics) or irregular (e.g., described by non-Euclidean mathematics). Euclidean mathematics describes those structures whose mass is directly proportional to a characteristic dimension of the spaced feature raised to an integer power (e.g., a first power, a second power or a third power). In one embodiment, the geometries can comprise shapes that are described by Euclidean mathematics such as, for example, lines, triangles, circles, quadrilaterals, polygons, spheres, cubes, fullerenes, or combinations of such geometries.

Figure 2A:
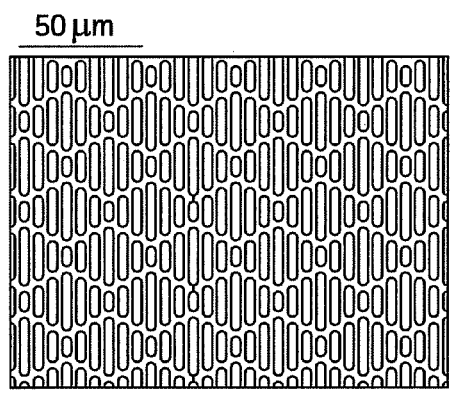
FIG. 2(a)-(d) illustrate some exemplary surface architectural patterns according to the invention.
Figure 2B:
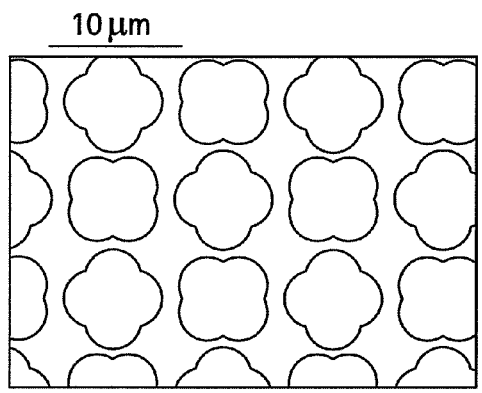
Figure 2C:
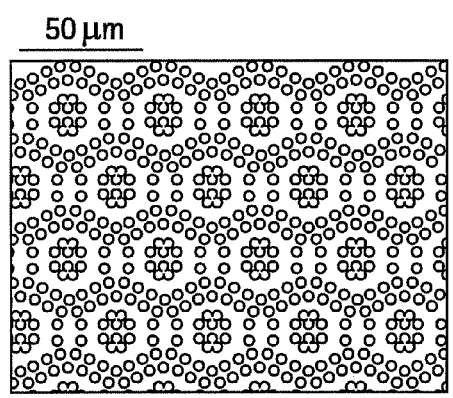
Figure 2D:
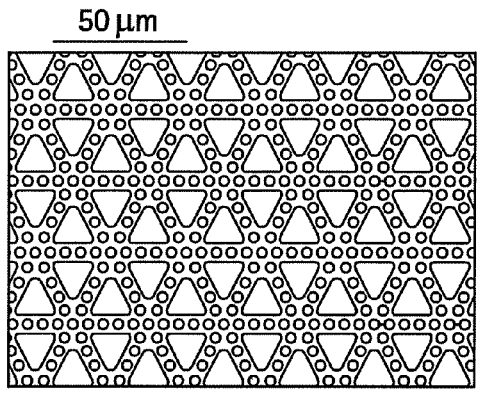

For example, the FIGS. 1(a) and 1(b) show that the spaced features are almost elliptical, i.e., the cross-sectional geometry of each feature when viewed from the top-down is similar to that which could be obtained by combining rectangles with semi-circles. Similarly, the FIGS. 2(b), 2(c) and 2(d) show features that comprise circles, sections of circles (e.g., semi-circles, quarter-circles), triangles, and the like.

In one embodiment, a repeat unit can be combined with a neighboring repeat unit so as to produce a combination of spaced apart features that have a geometry that is described by Euclidean mathematics. As can be seen in the FIGS. 2(c) and 2(d), the respective repeat units can be combined to produce different geometries. For example in the FIG. 2(d), the repeat unit can be combined with a single neighboring repeat unit to produce a diamond shaped geometry. Similarly, 3 or more neighboring repeat units can be combined to produce a rhombohedral, while six repeat units can be combined to produce a hexagon. Thus repeat units may be combined to produce structures whose geometries can be described by Euclidean mathematics.

In one embodiment, the spaced features can have irregular geometries that can be described by non-Euclidean mathematics. Non-Euclidean mathematics is generally used to describe those structures whose mass is directly proportional to a characteristic dimension of the spaced feature raised to a fractional power (e.g., fractional powers such as 1.34, 2.75, 3.53, or the like). Examples of geometries that can be described by non-Euclidean mathematics include fractals and other irregularly shaped spaced features.

In one embodiment, spaced features whose geometries can be described by Euclidean mathematics may be combined to produce features whose geometries can be described by non-Euclidean mathematics. In other words, the groupings of features can have dilational symmetry. The fractal dimension can be measured perpendicular to the surface upon which the features are disposed or may be measured parallel to the surface upon which the features are disposed. The fractal dimensions are measured in the inter-topographical gaps.

In one embodiment, the fractal dimensions can have fractional powers of about 1.00 to about 3.00, specifically about 1.25 to about 2.25, more specifically about 1.35 to about 1.85 in a plane measured parallel to the surface upon which the features are disposed. In another embodiment, the fractal dimensions can have fractional powers of about 1.00 to about 3.00, specifically about 1.25 to about 2.25, more specifically about 1.35 to about 1.85 in a plane measured perpendicular to the surface upon which the features are disposed.

In yet another embodiment, the fractal dimensions can have fractional powers of about 3.00 to about 4.00, specifically about 3.25 to about 3.95, more specifically about 3.35 to about 3.85 in a plane measured perpendicular to the surface upon which the features are disposed. In other words, the tortuous pathway or the surface of each feature may be textured with features similar to those of the pattern (albeit on a smaller scale), thus creating micro-tortuous pathways and nano-tortuous pathways within the tortuous pathway itself.

Figure 12:
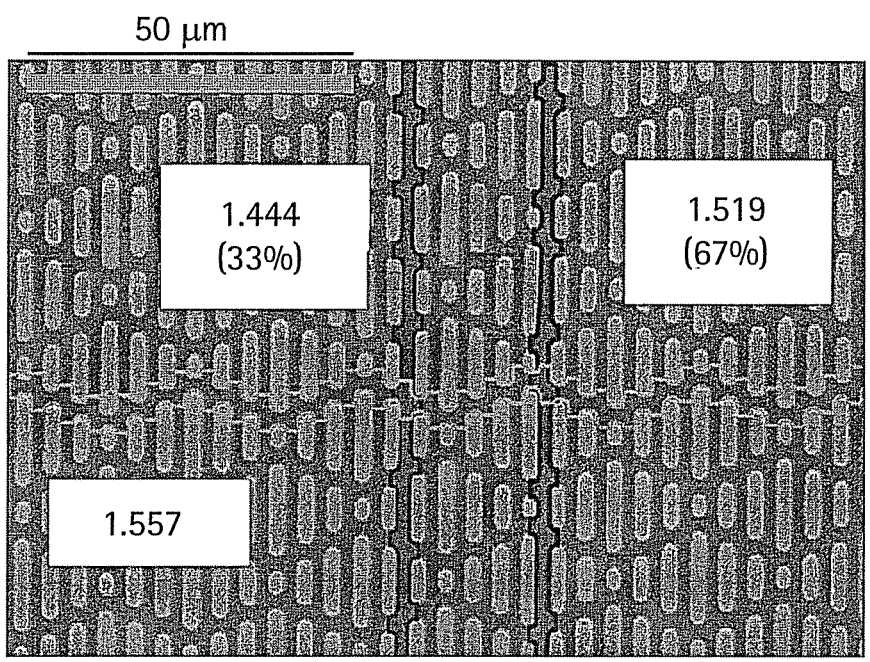
FIG. 12 is a photograph showing the fractal dimensions measured parallel to the surface of the substrate.

In another embodiment, the spaced features may have multiple fractal dimensions in a direction parallel to the surface upon which the features are disposed. The spaced features may be arranged to have 2 or more fractal dimensions, specifically 3 or more dimensions, specifically 4 or more dimensions in a direction parallel to the surface upon which the features are disposed. As can be seen in the FIG. 12 (a), the features have 3 different fractal dimensions in a plane parallel to the surface upon which the features are disposed. The fractal dimensions created by the features in a direction from the top to the bottom of the micrograph are 1.444 and 1.519 respectively, while the fractal dimension created by the features in a direction from left to right have dimensions of 1.557. The presence of the texture having multiple fractal dimensions prevents bioadhesion of algae, bacteria, virus, and other organisms.

In yet another embodiment, the spaced features may have multiple fractal dimensions in a direction perpendicular to the surface upon which the features are disposed. The spaced features may be arranged to have 2 or more fractal dimensions, specifically 3 or more dimensions, specifically 4 or more dimensions in a direction parallel to the surface upon which the features are disposed.

As will be noted below, the tortuous pathway may be defined by a sinusoidal function, a spline function, a polynomial function, or the like. The tortuous pathway generally exists between a plurality of groupings of spaced features and may occasionally be interrupted by the existence of a feature or by contact between two features. For example, in the FIGS. 5(a) and 5(b), the sinusoidal tortuous pathway intersects with the commonly shared feature and is thereby interrupted by it. The frequency of the intersection between the tortuous pathway and the spaced feature may be periodic or aperiodic. In one embodiment, the tortuous pathway may have a periodicity to it. In another embodiment, the tortuous pathway may be aperiodic. In one embodiment, two or more separate tortuous pathways never intersect one another.

The tortuous pathway can have a length that extends over the entire length of the surface upon which the pattern is disposed, if the features that act as obstructions in the tortuous pathway are by-passed. The width of the tortuous pathway as measured between two adjacent features of two adjacent patterns are about 10 nanometers to about 500 micrometers, specifically about 20 nanometers to about 300 micrometers, specifically about 50 nanometers to about 100 micrometers, and more specifically about 100 nanometers to about 10 micrometers.

The spaced features have linear pathways or channels between them. In one embodiment, the spaced features can have a plurality of linear pathways or a plurality of channels between them.

The spaced features can be periodic or aperiodic. As can be seen in the FIG. 1(a), the spaced features can be periodic, while as seen in the FIGS. 7(a), 7(b) and 7(c), the spaced features can be aperiodic. In a similar manner, the patterns can be periodic or aperiodic.

As noted above, the spaced features can have different dimensions (sizes). The average size of the spaced features can be nanoscale (e.g., they can be less than 100 nanometers) or greater than or equal to about 100 nanometers. In one embodiment, the spaced features can have average dimensions of 1 nanometer to 500 micrometers, specifically about 10 nanometers to about 200 micrometers, and more specifically about 50 nanometers to about 100 micrometers.

In another embodiment, the average periodicity between the spaced features can be about 1 nanometer to about 500 micrometers. In one embodiment, the periodicity between the spaced features can be about 2, 5, 10, 20, 50, 100 or 200 nanometers. In another embodiment, the average periodicity between the spaced features can be about 2, 5, 10, 20, 50, 100 or 200 nanometers. In another embodiment, the periodicity can be about 0.1, 0.2, 0.5, 1, 5, 10, 20, 50, 100, 200, 300, 400 or 450 micrometers. In yet another embodiment, the average periodicity can be about 0.1, 0.2, 0.5, 1, 5, 10, 20, 50, 100, 200, 300, 400 or 450 micrometers.

In one embodiment, the spaced features can have dimensions of 1 nanometer to 500 micrometers, specifically about 10 nanometers to about 200 micrometers, and more specifically about 50 nanometers to about 100 micrometers.

In another embodiment, the periodicity between the spaced features can be about 1 nanometer to about 500 micrometers. In one embodiment, the periodicity between the spaced features can be up to about 2, 5, 10, 20, 50, 100 or 200 nanometers. In another embodiment, the periodicity between the spaced features can be about 2, 5, 10, 20, 50, 100 or 200 nanometers. In another embodiment, the periodicity can be up to about 0.1, 0.2, 0.5, 1, 5, 10, 20, 50, 100, 200, 300, 400 or 450 micrometers. In yet another embodiment, the periodicity can be up to about 0.1, 0.2, 0.5, 1, 5, 10, 20, 50, 100, 200, 300, 400 or 450 micrometers.

In one embodiment, each feature of a pattern has at least one neighboring feature that has a different geometry (e.g., size or shape). A feature of a pattern is a single element. Each feature of a pattern has at least 2, 3, 4, 5, or 6 neighboring features that have a different geometry from the feature. In one embodiment, there are at least 2 or more different features that form the pattern. In another embodiment, there are at least 3 or more different features that form the pattern. In yet another embodiment, there are at least 4 or more different features that form the pattern. In yet another embodiment, there are at least 5 or more different features that form the pattern.

In another embodiment, at least two identical features of the pattern have at least one neighboring feature that has a different geometry (e.g., size or shape). A feature of a pattern is a single element. In one embodiment, two identical features of the pattern have at least 2, 3, 4, 5, or 6 neighboring features that have a different geometry from the identical features. In another embodiment, three identical features of the pattern have at least 2, 3, 4, 5, or 6 neighboring features that have a different geometry from the identical features.

In another embodiment, each pattern has at least one or more neighboring patterns that have a different size or shape. In other words, a first pattern can have a second neighboring pattern that while comprising the same features as the first pattern can have a different shape from the first pattern. In yet another embodiment, each pattern has at least two or more neighboring patterns that have a different size or shape. In yet another embodiment, each pattern has at least three or more neighboring patterns that have a different size or shape. In yet another embodiment, each pattern has at least four or more neighboring patterns that have a different size or shape.

As noted above the chemical composition of the spaced features can be different from the surface. The spaced features and the surfaces from which these features are projected or projected into can also comprise organic polymers or inorganic materials.

Organic polymers used in the spaced features and/or the surface can be may be selected from a wide variety of thermoplastic polymers, blend of thermoplastic polymers, thermosetting polymers, or blends of thermoplastic polymers with thermosetting polymers. The organic polymer may also be a blend of polymers, copolymers, terpolymers, or combinations comprising at least one of the foregoing organic polymers. The organic polymer can also be an oligomer, a homopolymer, a copolymer, a block copolymer, an alternating block copolymer, a random polymer, a random copolymer, a random block copolymer, a graft copolymer, a star block copolymer, a dendrimer, a polyelectrolyte (polymers that have some repeat groups that contain electrolytes), a polyampholyte (a polyelectrolyte having both cationic and anionic repeat groups), an ionomer, or the like, or a combination comprising at last one of the foregoing organic polymers.

Examples of the organic polymers are polyacetals, polyolefins, polyacrylics, polycarbonates, polystyrenes, polyesters, polyamides, polyamideimides, polyarylates, polyarylsulfones, polyethersulfones, polyphenylene sulfides, polyvinyl chlorides, polysulfones, polyimides, polyetherimides, polytetrafluoroethylenes, polyetherketones, polyether etherketones, polyether ketone ketones, polybenzoxazoles, polyphthalides, polyacetals, polyanhydrides, polyvinyl ethers, polyvinyl thioethers, polyvinyl alcohols, polyvinyl ketones, polyvinyl halides, polyvinyl nitriles, polyvinyl esters, polysulfonates, polysulfides, polythioesters, polysulfones, polysulfonamides, polyureas, polyphosphazenes, polysilazanes, styrene acrylonitrile, acrylonitrile-butadiene-styrene (ABS), polyethylene terephthalate, polybutylene terephthalate, polyurethane, ethylene propylene diene rubber (EPR), polytetrafluoroethylene, perfluoroelastomers, fluorinated ethylene propylene, perfluoroalkoxyethylene, polychlorotrifluoroethylene, polyvinylidene fluoride, polysiloxanes, or the like, or a combination comprising at least one of the foregoing organic polymers.

Examples of polyelectrolytes are polystyrene sulfonic acid, polyacrylic acid, pectin, carageenan, alginates, carboxymethylcellulose, polyvinylpyrrolidone, or the like, or a combination comprising at least one of the foregoing polyelectrolytes.

Examples of thermosetting polymers suitable for use in the polymeric composition include epoxy polymers, unsaturated polyester polymers, polyimide polymers, bismaleimide polymers, bismaleimide triazine polymers, cyanate ester polymers, vinyl polymers, benzoxazine polymers, benzocyclobutene polymers, acrylics, alkyds, phenol-formaldehyde polymers, novolacs, resoles, melamine-formaldehyde polymers, urea-formaldehyde polymers, hydroxymethylfurans, isocyanates, diallyl phthalate, triallyl cyanurate, triallyl isocyanurate, unsaturated polyesterimides, or the like, or a combination comprising at least one of the foregoing thermosetting polymers.

Examples of blends of thermoplastic polymers include acrylonitrile-butadiene-styrene/nylon, polycarbonate/acrylonitrile-butadiene-styrene, acrylonitrile butadiene styrene/polyvinyl chloride, polyphenylene ether/polystyrene, polyphenylene ether/nylon, polysulfone/acrylonitrile-butadiene-styrene, polycarbonate/thermoplastic urethane, polycarbonate/polyethylene terephthalate, polycarbonate/polybutylene terephthalate, thermoplastic elastomer alloys, nylon/elastomers, polyester/elastomers, polyethylene terephthalate/polybutylene terephthalate, acetal/elastomer, styrene-maleicanhydride/acrylonitrile-butadiene-styrene, polyether etherketone/polyethersulfone, polyether etherketone/polyetherimide polyethylene/nylon, polyethylene/polyacetal, or the like.

Polymers that can be used for the pattern or the substrate include biodegradable materials. Suitable examples of biodegradable polymers are as polylactic-glycolic acid (PLGA), poly-caprolactone (PCL), copolymers of polylactic-glycolic acid and poly-caprolactone (PCL-PLGA copolymer), polyhydroxy-butyrate-valerate (PHBV), polyorthoester (POE), polyethylene oxide-butylene terephthalate (PEO-PBTP), poly-D,L-lactic acid-p-dioxanone-polyethylene glycol block copolymer (PLA-DX-PEG), or the like, or combinations comprising at least one of the foregoing biodegradable polymers. The biodegradable polymers upon undergoing degradation can be consumed by the body without any undesirable side effects.

In one embodiment, the pattern can comprise a polymeric resin that is blended with a biologically active agent to form a drug coating. The biologically active agent is then gradually released from the pattern, which simply acts as a carrier. When the polymeric resin is physically blended (i.e., not covalently bonded) with the biologically active agent, the release of the biologically active agent from the drug coating is diffusion controlled. It is generally desirable for the pattern to comprise an amount of about 5 weight percent (wt %) to about 90 wt % of the biologically active agent based on the total weight of the drug coating. Within this range, it is generally desirable to have the biologically active agent present in an amount of greater than or equal to about 10, preferably greater than or equal to about 20, and more preferably greater than or equal to about 30 wt % based on the total weight of the drug coating. Within this range it is generally desirable to have the biologically active agent present in an amount of less than or equal to about 75, preferably less than or equal to about 70, and more preferably less than or equal to about 65 wt % based on the total weight of the drug coating. The drug coating may be optionally coated with an additional surface coating if desired. When an additional surface coating is used, the release of the biologically active agent is interfacially controlled. The drug coating may be disposed only on the surface of the features or alternatively on the surface of the tortuous pathway.

In another exemplary embodiment, the biologically active agent may be covalently bonded with a biodegradable polymer to form the drug coating. The rate of release is then controlled by the rate of degradation of the biodegradable polymer. Suitable examples of biodegradable polymers are provided above. Within this range, it is generally desirable to have the biologically active agent present in an amount of greater than or equal to about 10, preferably greater than or equal to about 20, and more preferably greater than or equal to about 30 wt % based on the total weight of the drug coating. Within this range, it is also generally desirable to have the biologically active agent present in an amount of less than or equal to about 75, preferably less than or equal to about 70, and more preferably less than or equal to about 65 wt %, based on the total weight of the drug coating.

When the pattern is used in a medical device, the drug coating may be coated onto the medical device in a variety of ways. In one embodiment, the drug coating may be dissolved in a solvent such as water, acetone, alcohols such ethanol, isopropanol, methanol, toluene, dimethylformamide, dimethylacetamide, hexane, and the like, and coated onto the medical device in the form of the pattern. In another embodiment, a monomer may be covalently bonded with the biologically active agent and then polymerized to form the drug coating, which is then applied onto the medical device in the form of the pattern. In yet another embodiment, the polymeric resin may first be applied as a coating (in the form of the pattern) onto the medical device, following which the coated device is immersed into the biologically active agent, thus permitting diffusion into the coating to form the drug coating.

In one embodiment, a biologically active agent can be added to the pattern. Te biologically active agent can be disposed upon the surface of the pattern or can be included in the pattern (e.g., mixed with the material forming the pattern). It may also be desirable to have two or more biologically active agents dispersed in a single drug coating layer. Alternatively, it may be desirable to have two or more layers of the drug coating coated upon the medical device. Various methods of coating may be employed to coat the medical device such as spin coating, electrostatic painting, dip-coating, painting with a brush, and the like, and combinations comprising at least one of the foregoing methods of coating.

Various types of biologically active agents may be used in the drug coating, which is used to coat the medical device. The coatings on the medical device may be used to deliver therapeutic and pharmaceutically biologically active agents including anti-analgesic agents, anti-arrhythmic agents, anti-bacterial agents, anti-cholinergic agents, anti-coagulant agents, anti-convulsant agents, anti-depressant agents, anti-diabetic agents, anti-diuretic agents, anti-fungal agents, anti-hypertensive agents, anti-inflammatory agents, anti-malarial agents, anti-neoplastic agents, anti-nootropic agents, anti-Parkinson agents, anti-retroviral agents, anti-tuberculosis agents, anti-tussive agents, anti-ulcerative agents, anti-viral agents, or the like, or a combination comprising at least one of the foregoing therapeutic and pharmaceutically biologically active agents.

Examples of other suitable therapeutic and pharmaceutically biologically active agents are anti-proliferative/antimitotic agents including natural products such as vinca alkaloids (e.g., vinblastine, vincristine, and vinorelbine), paclitaxel, epidipodophyllotoxins (e.g., etoposide, teniposide), antibiotics (e.g., dactinomycin, actinomycin D, daunorubicin, doxorubicin, penicillin V, penicillin G, ampicillin, amoxicillin, cephalosporin, tetracycline, doxycycline, minocycline, demeclocycline, erythromycin, aminoglycoside antibiotics, polypeptide antibiotics, nystatin, griseofulvin, and idarubicin), anthracyclines, mitoxantrone, bleomycins, plicamycin, mithramycin and mitomycin, enzymes (L-asparaginase, which systemically metabolizes L-asparagine and deprives cells which do not have the capacity to synthesize their own asparagine), antiplatelet agents such as G(GP) IIb/IIIa inhibitors and vitronectin receptor antagonists, anti-proliferative/antimitotic alkylating agents such as nitrogen mustards (e.g., mechlorethamine, cyclophosphamide and analogs, melphalan, chlorambucil), ethylenimines and methylmelamines (e.g., hexamethylmelamine and thiotepa), alkyl sulfonates-busulfan, nitrosoureas (e.g., carmustine (BCNU) and analogs, streptozocin), trazenes-dacarbazinine (DTIC), anti-proliferative/antimitotic antimetabolites such as folic acid analogs (e.g., methotrexate), pyrimidine analogs (e.g., fluorouracil, floxuridine, cytarabine), purine analogs and related inhibitors (e.g., mercaptopurine, thioguanine, pentostatin and 2-chlorodeoxyadenosine {cladribine}), platinum coordination complexes (e.g., cisplatin, carboplatin), procarbazine, hydroxyurea, mitotane, aminoglutethimide, hormones (e.g., estrogen), anti-coagulants (e.g., heparin, synthetic heparin salts and other inhibitors of thrombin), fibrinolytic agents (e.g., tissue plasminogen activator, streptokinase and urokinase), aspirin, dipyridamole, ticlopidine, clopidogrel, abciximab, antimigratory, antisecretory (e.g., breveldin), anti-inflammatory: such as adrenocortical steroids (e.g., Cortisol, cortisone, fludrocortisone, prednisone, prednisolone, 6α-methylprednisolone, triamcinolone, betamethasone, and dexamethasone), non-steroidal agents (e.g., salicylic acid derivatives such as aspirin, para-aminophenol derivatives such as acetaminophen, indole and indene acetic acids (e.g., indomethacin, sulindac, etodalac), heteroaryl acetic acids (e.g., tolmetin, diclofenac, ketorolac), arylpropionic acids (e.g., ibuprofen and derivatives), anthranilic acids (e.g., mefenamic acid, meclofenamic acid), enolic acids (e.g., piroxicam, tenoxicam, phenylbutazone, oxyphenthatrazone), nabumetone, gold compounds (e.g., auranofin, aurothioglucose, gold sodium thiomalate), immunosuppressives (e.g., cyclosporine, tacrolimus (FK-506), sirolimus (e.g., rapamycin, azathioprine, mycophenolate mofetil), angiogenic agents such as vascular endothelial growth factor (VEGF), fibroblast growth factor (FGF), angiotensin receptor blockers, nitric oxide donors, anti-sense oligionucleotides and combinations thereof, cell cycle inhibitors, mTOR inhibitors, and growth factor receptor signal transduction kinase inhibitors, retenoids, cyclin/CDK inhibitors, HMG co-enzyme reductase inhibitors (statins) or protease inhibitors.

The biologically active agents may also include cancer inhibitors. Suitable examples of cancer inhibitors are (−)-Ci-Cdp1, (−)-Ci-Cdp2, (−)-epigallocatechin gallate, (+)-Cbi-Cdpi2, (+)-Ci-Cdp2, 10-Deacetylbaccatin Iii, 4-demethoxy daunorubicin, 5-azacytidine/5-aza-2'-deoxycytidine, 5-fluorouracil, 5-iminodoxorubicin hydrochloride, 6-mercaptopurine, aclarubicin, acodazole, actinomycin D, adenine phosphate, adenosine, aderbasib, adozelesin; U-73,975, afeletecan, alemtuzumab, alitreninoin, alosetron HCl, alphitolic acid, altretamine, alvespimycin, ambazone, ametantrone, amifostine, aminoglutethimide, amsacrine HCl, amsilarotene, amygdalin, anagrelide, anastrozole, anaxirone, ancitabine, annomontacin, annomuricin A, (C19/C20-Erythro), annomuricin B, (C10/C11, C19/C20-Erythro), annomuricin C, (All Threo) annomuricin E, annonacin, annonacin-10-One, annonacin-A-One, annonidin B, annonin VI, annosquamosin A, annosquamosin B, antramycin, apaziquone, argimesna, aristoforin, arsenic trioxide, artemisinin, ascomycin, asparaginase, atosiban, atrimustine, axitinib, azasetron HCl, azatepa, azathioprine, azotomycin, bafetinib, balamapimod, banoxantrone, batabulin, batimastat, Bbr-34384, becatecarin, belotecan, benaxibine, bendamustine, benzodepa, berubicin, betulin, betulinic acid, betulinic aldehyde, bevacizumab, bexarotene, bicalutamide, bietaserpine, biricodar, bisantrene, bistramid A; bistratene A, bizelesin, bleomycin, bleomycin A2 [Sulfate], bleomycin A5, bleomycin Sulfate, bortezomib, bosentan, bosutinib, brequinar sodium, brequinar, bropirimine, brostallicin, budotitane, bullatacin, buserelin, busulfan, cabazitaxel, calcium folinate, calcium levofolinate, calusterone, camptothecin, canertinib, canfosfamide, cantharidin, capecitabine, caracemide, carbetimer, carboplatin, carboprost, carboprost (carboprost tromethamine), carboquone, carfilzomib, carglumic acid, carmofur, carmustine, carzelesin, cedefingol, cemadotin, cetuximab, cevipabulin, chlorambucil, chlormethine (mechlorethamine), chlorotamoxifen, chlorotrianisene, cioteronel, cisplatin, cladribine, clanfenur, clofarabine, clofazimine, clomifene citrate, cordycepin, corosolic acid, crisnatol, curcumin, cyclocytidine, cyclophosphamide, cytarabine, cytidine, D-aminolevulinic acid, dacarbazine, damsin, daniquidone, danusertib, daporinad, darinaparsin, dasatinib, daunoblastin, daunorubicin/daunomycin, decitabine, deferasirox, deforolimus, demecolcine, denibulin, detorubicin, dexniguldipine, dexormaplatin, dezaguanine, dianhydrodulcitolum, dibrospidium chloride, dienogest, diflomotecan, dinalin, disermolide, docetaxel, dofequidar, dolasetron mesylate, dovitinib, doxifluridine, doxorubicin, dromostanolone, duazomycin, duocarmycin, dynemicin, ecomustine, edatrexate, edotecarin, edotreotide, eflornithine, elacridar, eacytarabine, elesclomol, elinafide, elomotecan, elsamitrucin, emitefur, enloplatin, enocitabine, enpromate, entecavir, entinostat, entricitabine, enzastaurin, epirubicin, eptaloprost, eribulin, erlotinib, Esorubicin, estramustine, etalocib, etanidazole, etoglucid, etoposide, exatecan, exemestane, exisulind, fadrozole, fazarabine, fiacitabine, floxuridine, fludarabine, fluoxymesterone, fluorocitabine, flutamide, formestane, forodesine, fosfluridine tidoxil, fosquidone, fostriecin, fotemustine, fotretamine, fulvestrant, fumagillin, galarubicin, galocitabine, gefitinib, gemcitabine, gemtuzumab ozogamicin, geroquinol, gigantetronenin, gigantetroneninone, gimatecan, gimeracil, gloxazone, glufosfamide, goniothalamicin, goniothalamicinone, goserelin, granisetron HCl, gusperimus, hexarelin, homoharringtonine, hydrocamptothecine, hydroxy carbamide, hydroxyurea, hypericin, ibandronate sodium, ibandronic acid, idarubicin HCl, idronoxil, ifosfamide, ilmofosine, imatinib, imatinib mesylate, imexon, improsulfan, incadronate, indibulin, indisulam, inolitazone, inproquone, intiquinatine, intoplicine, iobenguane, irinotecan hydrochloride, irofulven, irsogladine, ispinesib, ixabepilone, ketotrexate, L-alanosine, laniquidar, lapatinib ditosylate, laromustine, larotaxel, ledoxantrone, lenalidomide, lentinan, lestaurtinib, letrozole, leuprolide acetate, leuprorelin, lexacalcitol, liarozole, lobaplatin, lomustine, lonafarnib, lonidamine, losoxantrone, Ly-83583, lysipressin, mafosfamide, mannomustine, mannosulfan, marimastat, marinomycin A, masitinib, maslinic acid, masoprocol, mechlorethamine, medorubicin, megestrol, mepitiostane, mercaptopurine, mesna, methotrexate, methyl aminolevulinate, metomidate, metoprine, meturedepa, miboplatin, midostaurin, mifamurtide, milataxel, miproxifene, miriplatin, misonidazole, mitindomide, mitoflaxone, mitoguazone, mitomycin, mitonafide, mitoquidone, mitotane, mitoxantrone, mitozolomide, mivobulin, mizoribine, mofarotene, mopidamol, motesanib, motexafin, mubritinib, muricapentocin, muricatacin, mustine HCl, mycophenolate mofetil, mycophenolic acid, nedaplatin, nelzarabine, nemorubicin, neocuproine, neptamustine, neratinib, nigericin, nilotinib, nilutamide, nimustine, ninopterin, nitracrine, nogalamycin, nolatrexed, norcantharidine, nor-dihydroguaiaretic acid, nortopixantrone, novembichin, obatoclax, octreotide, olaparib, oleanolic aldehyde, omacetaxine mepesuccinate, ombrabulin, omtripolide, ondansetron HCl, ortataxel, oteracil, oteracil potassium, oxaliplatin, oxisuran, oxophenarsine, paclitaxel ceribate, palifosfamide, palonosetron, pamidronate disodium, pamidronic acid, panitumumab, panobinostat, patubilone, pazelliptine, pazopanib, pegaspargase, peldesine, pelitinib, pelitrexol, pemetrexed disodium, pentostatin, peplomycin, peretinoin, perfosfamide, perifosine, pibrozelesin hydrobromide, picoplatin, pinafide, piposulfan, pirarubicin, pirfenidone, piritrexim, piroxantrone, pixantrone, plevitrexed, plicamycin, plitidepsin, plomestane, podophyllotoxin, pomalidomide, porfimer sodium, pralatrexate, prinomastat, procarbazine HCl, propamidine, prospidium chloride, pumitepa, puromycin, pyrazofurin, ouarfloxin, raltegravir, raltitrexed, ramosetron HCl, ranimustine, retaspimycin, retelliptine, riboprine, ritrosulfan, rituximab, roflumilast, romidepsin, ropidoxuridine, roquinimex, rosabulin, rubitecan, sabarubicin, safingol, salirasib, sapacitabine, saracatinib, sardomozide, satraplatin, sebriplatin, seliciclib, semaxanib; SU-5416, semustine, sermorelin, simotaxel, simtrazene, sitagliptin, sizofuran, soblitodin, sobuzoxane, sodium phenylbutyrate, sorafenib, sparfosic acid, sparsomycin, spiroplatin, squalamine, squamocin, streptonigrin, streptovarycin, streptozocin, sufosfamide, sulofenur, sunitinib, swainsonine, tacedinaline, tafluposide, talabostat, talisomycin, tallimustine, talotrexin, taltobulin, tamoxifen citrate, tandutinib, tanespimycin, tariquidar, tasidotin, tasisulam, tauromustine, tegafur, tegafur-uracil, telantinib, teloxantrone, temozolomide, teniposide, tenuazonic acid, terameprocol, teriparatide, tesetaxel, testolactone, tezacitabine, thiamiprine, thioguanine, thiotepa, thymopoietin, tiazofurine, tilomisole, tilorone, timcodar, timonacic, tioguanine, tirapazamine, tocladesine, tomudex, topotecan hydrochloride, toremifene citrate, tosedostat, tositumomab, toxipantrone, trastuzumab, trenimon, tretinoin, triciribine, trilostane, trimetrexate, triplatin tetranitrate, triptolide, triptorelin, trofosfamide, tropisetron HCl, tubulozole, tylophorin, U-67786, U-68415, U-71184, U-76074, U-78057, ubenimex, uramustine, uredepa, urethane, uridine, ursolic acid, ursolic aldehyde, vadimezan, valrubicin, valspodar, vandetanib, vapreotide, vatalanib; PTK-787, verteporfin, vildagliptin, vinblastine sulfate, vincristine, vindesine, vinepidine, vinflunine, vinformide, vinfosiltine, vinleucinol, vinleurosine, vinorelbine [Base], vinorelbine tartrate, vintriptol, vinzolidine, voriconazole, vorinostat, vorozole, wilforlide A, xanthomycin A, zalcitabine, zeniplatin, zilascorb, zinostatin, zoledronic acid, zorubicin, zosuquidar, or the like, or a combination comprising at least one of the foregoing cancer inhibitors.

A more complete list of compounds, most of which are pharmaceutical or veterinary, which can be utilized in the present invention includes, but is not limited to: abacavir, abamectin, abanoquil, abaperidone, abarelix, abecamil, abiraterone, abitesartan, ablukast, abunidazole, acadesine, acamprosate, acaprazine, acebrochol, acebutolol, acecainide, acecarbromal, aceclidine, aceclofenac, acedapsone, acediasulfone, acedoben, acefluranol, acefurtiamine, acefylline clofibrol, acefylline piperazine, aceglatone, aceglutaminde, acemetacin, aceneuramicacid, acenocoumarol, acepeprone, acepromazine, aceprometazine, acequinoline, acesulfame, acetaminosalol, acetanilide, acetarsone, acetaminophen, acetazolamide, acetiamine, acetiromate, acetohexamide, acetophenazone, acetophenetidin, acetorphine, acetosulfone, acetriozoic acid, acetylcysteine, acetyldigitoxin, acetylleucine, acetyltributyl citrate, acetyltriethyl citrate, aceveltrate, acexamin acid, acifran, acipimox, acitazanolast, acitemate, acitretin, acivicin, alcantate, aclarubicin, aclatonium napadisilate, acolbifene, aconiazide, aconitine, acotiamide, acoxatrine, acreozast, acridorex, acriflavine, acrihellin, acrisorcin, acrivastine, acroinonide, acronine, actaplanin, actarit, actinoquinol, actisolide, actodigin, acyclovir, adafenoxate, adamexine, adapalene, adaprolol, adatanserin, adefovir, adekalant, adelmidrol, ademitrionine, adenosine, adibendal, adicillin, adimolol, adinazolam, adiphenine, aditeren, aditoprim, adosopine, adozelesin, adrafinil, adrenalone, adrogolide, afalanine, afeletecan, afloqualone, afovirsen, afurolol, aganodine, aglepristone, agomelatine, aklomide, alacepril, alafosfalin, alagebrium, alamecin, alamifovir, alanine, alanosine, alaproclate, alatrofloxacin, alazanine triclofenate, albaconazole, albendazole, albuterol, albutoin, alclofenac, alclometasone, alcloxa, alcuronium, aldioxa, aldosterone, alemcinal, alendronic acid, alentemol, alepride, alestramustine, aletamine, alexidine, alexitol, alexomycin, alfacalcidol, alfadex, alfidalone, alfaprostol, alfatradiol, aldaxalone, alfentranil, alfluzosin, algeldrate, algestone, alibendol, aliconazole, alifedrine, alifurane, alilusem, alimadol, alinastine, alinidine, alipaminde, aliskiren, alitame, alitretinoin, alizapride, alletorphine, allobarbitol, allocamide, allocupreide, allomethadione, allopurinol, allylestrenol, allylprodine, almecillin, almestrone, alminoprofen, almitrine, almokalant, almotriptan, almoxatone, almurtide, alnespirone, alniditan, alonacic acid, alonimid, aloracetam, alosetron, alovudine, aloxidone, aloxiprin, aloxistatin, alozafone, alpertine, alphameprodine, alphamethadol, alphamethyldopa, alphaprodine, alpidem, alpiropride, alprafenone, alprazolam, alprenolol, alprenoxime, alprostadil, alrestatin, altanserin, altapizone, alteconazole, althiazide, altinicline, altoqualiine, altrenogast, altretamine, alvemeline, alverine, alvimopan, alvocidib, amadinone, amafalone, amanozine, amantadine, amantocillin, ambamustine, ambasilide, ambazone, ambenonium, ambenoxan, ambomycin, ambrisentan, ambroxol, ambruticin, ambucaine, ambucetamide, ambuphylline, ambuside, ambutonium, amcinafal, amcinafide, amcinonide, amdinocillin, amdoxovir, ambucort, amedalin, amelometasone, ameltolide, amelubant, amesergide, ametantrone, amethocaine, amezapine, amezinium, amfenac, amfepentorex, amfetaminil, amflutizole, amfonelic, amicarbalide, amicloral, amicycline, anidantel, amidapsone, amidephrine, amiflamine, amifloverine, amifloxacin, amifostine, amiglumide, amikacin, amikhelline, amiloride, amiloxate, aminacrine, amindocate, amineptine, aminoglutethimide, aminohippuric acid, aminolevulinic acid, aminometradine, aminopentamide, aminophenazone, aminophylline, aminopromazine, aminopterin, aminopyrine, aminoquinol, aminoquinuride, aminorex, aminosalicylic acid, aminothiazole, amiodarone, amiperone, amphenazole, amipizone, amiprolose, amiquinsin, amisometradine, amisulprode, amiterol, amithiozone, amitivir, amitraz, amitriptyline, amitriptyinoxide, amixetrine, amlexanox, amlintide, amlodipine, amocarzine, amodiaquine, amolanone, amonafide, amoproxan, amopyroquine, amorolfine, amoscanate, amosulatol, amotosalen, amotriphene, amoxapine, amoxecaine, amoxicillin, amoxydramine, amperozide, anphechloral, amphenidone, amphetamine, amphomycin, amphotalide, amphotericin, ampicillin, ampiroxicam, amprenavir, amprolium, ampyrimine, ampyzine, amquinate, amrubicin, amsacrine, amtolmetin, amustaline, amylobarbital, angestone, anagrelide, anakinra, anaritide, anastrozole, anatibant, anaxirone, anazocine, anazolene, ancarolol, ancitabine, andolast, androstenediol, androstenedione, andulafungin, anecortave, anetholtrithion, angiotensin amide, andidoxamine, anidulafungin, anilamate, anileridine, anilopam, anipamil, aniracetam, anirolate, anisacril, anisindione, anisopirol, anisotropine, anisperimus, anitrazafen, anpirtoline, ansoxetine, antafenite, antazoline, antazonite, anthelmycin, anthralin, anthramycin, antipyrine, antrafenine, apadoline, apafant, apalcillin, apaxafylline, apaziquone, apazone, apicycline, aplindore, apomorphine, apovincamine, apraclonidine, apramycin, aprepitant, aprakalim, aprindine, aprinocarsine, apofene, aprosulate, aptazapine, aptiganel, aptocaine, aranidipine, aranotin, arbaprosil, arbekacin, arbutamine, arclofenin, ardacin, ardeparin, arecoline, arfalasin, arfendazam, arformoterol, argatroban, argimesna, argipressin, argiprestocin, arlidone, arimoclomol, aripiprazole, armodafinil, arnolol, arofylline, artinolol, arprinocid, arpromidine, arsanilic acid, arteflene, artemether, artemisinin, artemotil, artenimol, artesunate, articaine, artilide, arundic acid, arzoxifene, ascorbic acid, arsenapine, aseripide, asimadoline, asobamast, asocainol, asoprisnil, aspartame, aspartocin, asperlin, aspirin, aspoxicillin, astemizole, astromicin, asulacrine, atamestane, ataprost, ataquimast, atavanavir, atenolol, atevirdine, atibeprone, atilmotin, atipamezole, atipromod, atiprosin, atizoram, atliprofen, atocalcitol, atolide, atomoxetine, atorvastatin, atosiban, atovaquone, atracurium, atrasentan, atraleuton, atrimustine, atrinositol, atromepane, atropine, atropine oxide, auranofin, aurothioglucose, avanafil, avasimibe, avicatonin, avalamycin, aviptadil, avitriptan, avizafone, avobenzone, azoparcin, avorelin, pyridine, axamozide, axitirome, axomadol, azabon, azabuperone, azacitadine, azacitidine, azaclorzine, azaconazole, azacosrterol, azacyclonol, azaftozine, azalanstat, azalomycin, azaloxan, azamethiphos, azamethonium, azamulin, azanator, azanidazole, azaperone, azapetine, azaquinzole, azaribine, azarole, azaserine, azasetron, azaspirium, azastene, azatadine, azathioprine, azelaic acid, azelastine, azelinnidipine, azepexole, azepindole, azetepa, azetirelin, azidamfenicol, azidocillin, azimexon, azimilide, azintamide, azipramide, azithromycin, azlocillin, azlocillin, azolimine, azosemide, aztomycin, aztreonam, azumolene, bacampicillin, bacitracin, baclofen, bacmecillinam, bakeprofen, balaglitazone, balazipone, balofloxacin, balsalazide, bamaluzole, bamaquimast, bambermycin, bambuterol, bamethan, bamifylline, bamipine, bamirastine, bamidazole, banoxantrone, baquiloprim, barbexaclone, barbital, barixibat, barmastine, barnidipine, barucamide, barusiban, basifungin, batalbulin, batanopride, batebulast, batelapine, batilol, batimastat, batoprozine, baxitoizine, bazedoxifene, bazinaprine, becanthone, becatecarin, beciparcil, beclamide, becliconazole, beclobrate, beclomethasone, beclotiamine, befetupitant, befiperide, befloxatone, befunolol, befuraline, bekanamycin, belaperidone, belarizine, belfosdil, belotecan, beloxamide, beloxepin, bemarinone, bemegride, bemesetron, bemetizide, beminafil, bemiparin, bemetradine, bemoradan, bemotrizinol, benactyzine, benafentrine, benapryzine, benaxibine, benazepril, bencianol, bencisteine, benclonidine, bencyclane, bendacalol, bendamustine, bendazac, bendazol, benderizine, bendroflumethazide, benethamine penicillin, benexate, benfluorex, benfosformin, benfotiamine, benfluorodil, benhepazone, benidipine, benmoxin, benolizime, benorilate, benorterone, benoxifos, benoxaprofen, benoxinate, benpenolisin, benperidol, benproperine, benrixate, bensalan, benserazide, bensuldazic acid, bentazepam, bentemazole, bentiamine, bentipimine, bentiromide, bentoquatam, benurestat, benzalkonium, benzarone, benzbromarone, benzestrol, benzethidine, benzethonium, benzetimide, benzilonium, benzindopyrine, benziodarone, benzmalecene, benznidazole, benzobarbital, benzocaine, benzoclidine, benzoctamine, benzodepa, benzododecinium, benzonatate, benzopyrronium, benzoquinonium, benzotript, benzoxiquine, benzoxonium, benzoylpas, benzphetamine, benzpiperylon, benzpyrinium, benzquercin, benzquinamide, benzthiazide, benztropine, benzydamine, benzylhydrochlorothiazide, benzylpenicillin, benzylsulfamide, bepafant, beperidium, bephenium, bepiastine, bepridil, beractant, beraprost, berberine, berefrine, bergenin, berlafenone, bermoprofen, bertosamil, berupipam, bervastatin, berythromycin, besigomsin, besipirdine, besonprodil, besulpamide, besunide, beta carotene, betacetylmethadol, betahistine, betaine, betameprodine, betamethadol, betamethasone, betamicin, betamipron, betaprodine, betaxolol, betazole, bethanacol, bethanidine, betiatide, betoxycaine, bevantolol, bevonium, bexarotene, bexlosteride, bezafibrate, beztiramide, bialamicol, biapenem, bibezonium, bibrocathol, bilcalutamide, bicifadine, bicoldil, biclofibrate, biclotymol, bicozamycin, bidimazium, bidisomide, bietamiverine, bietaserpine, bifemelane, bifepramide, bifeprofen, bifeprunox, bifluranol, bifonazole, bilastine, bimakalim, bimatoprost, bimoclomol, bimosiamose, bindarit, binedaline, binfioxacin, binfibrate, biniramycin, binizolast, binodenosine, binospirone, bioallethrin, botin, bipenamol, biperiden, biphenamine, biricodar, biriperone, bisacodyl, bisantrene, bisaramil, bisbendazole, bisbentiamine, bisbutiamine, bisdequilinium, bisfenazone, bisfentidine, bisnafide, bisorbin, bisoctriazole, bisoprolol, bisorcic, bisoxatin, bispyrithione, bithonol, bithionoloxide, butipazone, bitolterol, bitoscanate, bivalirudin, bizelesin, bleomycin, blonanserine, bluensomycin, bofumustine, bolandiol, bolasterone, bolazine, boldenone, bolenol, bolmantalate, bometolol, bopindolol, bornaprine, bornaprolol, borelone, borocaptane, bortezomib, bosentan, botiacrine, boxidine, brallobarbital, brasofensine, brazergoline, brefonalol, bremazocine, brequinar, bretazenil, bretylium, brifentanil, brimonidine, brinazaprone, brindoxime, brinzolamide, brivudine, brobactam, broclepride, brocrestine, brocrinat, brodimoprim, brofaromine, brofoxine, brolaconazole, brolamfetamine, bromadoline, bromamid, bromazepam, bromchlorenone, bromebric acid, bromerguride, brometenamine, bromfenac, bromhexene, bomindione, bromisovalum, bromociclen, bromocriptine, bromodiphenylhydramine, bromofenfos, bromofos, bromopride, bromoxanide, bromperidol, brompheniramine, broparestrol, broperamol, bropirimine, broquinaldol, brosotaminde, brostallicin, brosuximide, brotianide, brotizolam, brovanexine, brovincamine, broxaldine, broxaterol, broxitalamide, broxuridine, broxyquinoline, bucamide, bucetin, buciclovir, bucillamine, bucindolol, bucladesine, buclizine, buclosaminde, bucloxic acid, bucolme, bucricaine, bucromarone, bucumolol, budesonide, budipine, budotitane, budralazine, bufenadrine, bufeniode, bufetolol, bufexamac, bufezolac, bufromedil, bufogentin, buformin, bufrolin, bufuralol, bufylline, bulaquine, bumadizone, bumecaine, bumepidil, bumetanide, bumetriazole, bunaftine, bunamidine, bunamiodyl, bunaprolast, bunazosin, bunitrolol, bunolol, buparvaquone, bupicomide, bupivacaine, bupranolol, buprenorphine, bupropion, buquinerin, buquinolate, buquiterine, buramate, burodiline, buserelin, buspirone, busulfan, butobarbital, butacaine, butacetin, butaclamol, butadiazamide, butafosfan, butalamine, butalbital, butamben, butamirate, butamisole, butamoxane, butanilicaine, butanserin, butantrone, butaperazine, butaprost, butaverine, butedronate, bytenafine, buterizine, butenamate, buthiazide, butibufen, butifrine, butikacin, butilfenin, butinazocine, butinoline, butirosin, butixirate, butixocort, butobendine, butoconazole, butocrolol, butoctamide, butofiolol, butonate, butopamine, butopiprine, butoprozine, butopyrammonium, butorphanol, butoxamine, butoxylate, butriptyline, butropium, butylscopolamine, butynamine, buzepide, cabastine, cabergoline, cactinomycin, cadralazine, cadrofloxacin, cafaminol, cafedrine, caffeine, calcifediol, calciprotriene, calcitriol, calcobutrol, caldaret, caldiamine, caloxetic acid, calteridol, clausterone, camazepam, cambendazole, camaglibose, camiverine, camptothecin and its analogues such as 9-amino camptothecin, 10-hydroxy camptothecin, 7-ethyl-10-hydroxy camptothecin, 9-nitro camptothecin and all other camptothecin analogues with six, seven and eight membered lactone rings, camonagrel, camostat, camylofin, canbisol, candesartan, candicidin, candocuronium, candoxatril, candoxatrilat, canertinib, canfosfamide, cangrelor, cannabinol, canrenoate, canrenone, capectitabine, capobenate, capobenic acid, capravirine, capreomycin, capromorelin, caproxamine, capsaicin, captamine, captodiame, captopril, capuride, carabersat, caracemide, carafiban, caramiphen, carbachol, carbadox, carbamazepine, carbentel, carbasone, carbaspirin, carbazeran, carbazochrome, carbazocine, cabenicillin, carbenoxolone, carbenzide, carbetapentane, carbetocin, carbidopa, carbimazole, carbinoxamine, carbiphene, carbofenotion, carboplatin, carboprost, carboquone, carbubarb, carburazepam, carbutamide, carbuterol, carcainium, carebastine, carfentanil, carfimate, cargutocin, cariporide, carisoprodol, carmantadine, carmofur, carmoterol, carmustine, camidazole, carnitine, carocamide, caroverine, caroxazone, carperidine, carperitide, carperone, carphenazine, carpindolol, carpipramine, carprazidil, carprofen, capronium, carsalam, carsatrin, cartasteine, cartazolate, carteolol, carubicin, carumonam, carvedilol, carvotroline, carzelesin, carzenide, casanthranol, casokefaminde, caspofungin, cathine, cathinone, cebaracetam, cedefingol, cefaclor, cefadroxil, cefalonium, cefaloram, cefamandole, cefaparole, cefatriazine, cefazaflur, cefazedone, cefazolin, cefbuperazone, cefanel, cefcapene, cefclidin, cefdaloxime, cefdinir, cefditoren, cefedrolor, cefempidone, cefepime, cefetamet, cefetecol, cefetriaxole, cefivtril, cefixime, cefmatilen, cefmenoxine, cefmepidium, cefmetazole, ceminox, cefodizime, cefonicid, cefoperazone, ceforanide, cefoselis, cefotaxime, cefotetan, cefotiam, cefovecin, cefoxazole, cofoxitin, cefozopran, cefpimizole, cefpiramide, cefpodoxime, cefprozil, cefquinome, cefrotil, cefroxadine, cefsulodin, cefsumide, ceftazidime, cefteram, ceftezole, ceftibuten, ceftioflur, ceftiolene, ceftioxide, ceftioxime, ceftriaxone, cefuracetamime, cefuroxime, cefuzonam, celecoxib, celgosivir, celiprolol, cemadotin, cephacetrile, cephadrine, cephalexin, cephaloglycin. Cephaloridine, cephalothin, cephapirin, cepharanthine, cephradine, cericlamine, cerivastatin, ceronapril, ceruletide, cetaben, cetalkonium, cetamolol, cetefloxacin, cethexonium, cethromycin, cetiedil, cetilistat, cetirizine, cetocycline, cetopheincol, cetotiamine, cetoxime, cetraxate, cetrimonium, cetylpyridinium, cevimeline, chaulmosulfone, chenodiol, chinofon, chlofibrate, chlophendianol, chloracyzine, chloralose, chlorambusil, chloramines-T, chloramphenicol, chlorazanil, chlorbenoxamine, chlorbetamide, chlorcyclizine, chlordantoin, chlordiazepoxide, chlordimorine, chlorhexidine, chlorindanol, chlorisondamine, chloramadione, chlormerodrin, chlormezanone, chlormidazole, chlornaphazine, chloroazodin, chloroprednisone, chloroprocaine, chloropyramine, chloroquine, chloroserpidine, chlorothen, chlorothiazide, chlorotrianisene, chloroxine, chloroxylenol, chlorphenesin, chlorpheniramine, chlorphenoctium, chlorphenoxamine, chlorphentermine, chlorproethazine, chlorproguanil, chlorpromazine, chlorpropamide, chlorprothixene, chlorpyrifos, chlortetracycline, chlorthalidone, chlorthenoxazine, chlorzoxazone, cholecalciferol, cholesterol, choline alfoscerate, choline, chromic chloride, chromonar, ciadox, ciaftalan, ciamexon, cianergoline, cianidanol, cianopramine, ciapilome, ciaprost, cicarperone, ciclactate, ciclafrine, ciclazindol, ciclesonide, clcletanine, cicliomenol, ciclonicate, ciclonium, ciclopirox, ciclopramine, cicloprofen, cicloprolol, ciclosidomine, ciclotizolam, ciclotropium, cicloxilic acid, cicloxolone, cicortonide, cidofovir, cidoxepin, cifenline, cifostodine, ciglitazone, ciheptolane, ciladopa, cilansertron, cilastatin, cilazapril, cilengitide, cilexin, cilnidipine, cilobamine, cilobradine, cilofungin, cilomilast, cilostamide, cilostazol, ciluprevir, cilutazoline, cimaterol, cimemoxin, cimetidine, cimetropium, cimicoxib, cimoxatone, cinacalcet, cinalukast, cinametic acid, cinamolol, cinanserin, cinaproxen, cinchophen, cinecromen, cinepazet, cinepazide, cinfenine, cinfenoac, cinfiumide, cingestol, cinitapride, cinmetacin, cinnamaverine, cinnamedrine, cinnarizine, cinnofuradione, cinoctramide, cinodine, cinolazepam, cinoquidox, cinoxacin, cinoxate, cinoxolone, cinoxopazide, cinperene, cinprazole, cinpropazide, cinpromide, cintazone, cintriamide, cinuperone, cioteronel, cipamfylline, cipemastat, ciprafamide, cipralisant, ciprazafone, ciprefadol, ciprocinonide, ciprofibrate, ciprofloxacin, ciprokiren, cipropride, ciproquazone, ciprestene, ciramadol, cirazoline, cirolemycin, cisapride, cisatracurium, cinconazole, cismadinone, cisplatin, cistinexine, citalopram, citatepine, citenamide, citenazone, citicoline, citiolone, cizolirtine, cladribine, clamidoxic acid, clamikalant, clamoxyquin, clanfenur, clanobutin, clantifen, clarithromycin, clavulanate, clazolam, clazolimine, clazuril, clebopride, clefamide, clemastine, clemeprol, clemizole, clenbuterol, clenpirin, clentiazem, cletoquine, clevidipine, clevudine, clibucaine, clidafidine, clidanac, clindium, climazolam, climbazole, climiqualine, clinafloxacin, clindamycin, clinofibrate, clinolamide, clinprost, clioquinol, clioxanide, cliprofen, cliropamine, clobazam, clobenoside, clobenzepam, clobenorex, clobenztropine, clobetasol, clobetasone, clobutinol, clobuzarit, clocanfamide, clocapramine, clociguanil, clocinizine, clocortolone, clocoumarol, clodacaine, clodanolene, clodazon, clodoxopone, clodronate, clofarabine, clofazimine, clofenamic acid, clofeniclan, clofenetamine, clofenoxyde, clofevine, clofexamine, clofezone, clofibrate, clofibric acid, clofibride, clofilium, clofucarba, clofoctol, cloforex, clofurac, clogestone, cloguanamil, clomacrin, clomegestone, clometacin, clometherone, clomethiazole, clometocillin, clomifenoxide, clominorex, clomiphene, clomipramine, clomocycline, clomoxir, clonazepam, clonazoline, clonidine, clonitazine, clonixeril, clonixin, clopamide, clopenthixol, cloperastine, cloperidone, clopidogrel, clopidol, clopimozide, clopipazan, clopirac, cloponone, cloprendol, cloprostenol, cloprothiazole, cloquinate, cloquinozine, cloracetadol, cloranolol, clorazepate, clorazepic acid, clorethane, chlorexolone, clorfenvinos, clorgiline, cloricromen, cloridarol, clorindanic acid, clorindione, clormecaine, cloroperone, clorophene, cloroqualone, clorotepine, clorprenaline, clorsulon, clortermine, closantel, closiramine, clostebol, clothiapine, clothixamide, clotiazepam, cloticasone, clotioxone, clotixamide, clotrimazole, clovoxamine, cloxacepride, cloxacillin, cloxazolam, cloxestradiol, cloximate, cloxotestosterone, cloxypendyl, cloxyquin, clozapine, cobalamide, cocaine, codeine, codoxime, cofistatin, cogazocine, colchicines, colestolone, colfenamate, colforsin, colfosceril, colimecycline, colterol, coluracetam, conessine, congazone, conivaptan, conorphone, cormethasone, corticorelin, cortisone, cortisuzol, cortivazol, cortodoxone, cotinine, cotriptyline, coumaphos, coumazolin, coumermycin, coumetarol, creatinine, creatinolfosfate, cresotamide, cridanimod, crilvastin, crisnatol, crobenetine, croconazole, cromakalim, cromitrile, cromoglicate lisetil, cromolyn, crolom, cronidipine, cropropamide, crotamiton, crotetamide, crotoniazide, crotoxyfos, crufomate, cuprimyxin, cuproxoline, cyacetacide, cyamemazine, cyanocobalamine, cyclacillin, cyclamate, cyclamic acid, cyclandelate, cyclarbamate, cyclazocine, cyclazodone, cyclexanone, cyclindole, cycliramine, cyclizine, cyclobarbital, cyclobendazole, cyclobenzaprine, cyclobutoic acid, cyclobutyrol, cyclocumarol, cyclofenil, cycloguanil, cycloheximide, cyclomenol, cyclomethycaine, cyclopentamine, cyclopenthiazide, cyclopentolate, cyclophenazine, cyclophosphamide, cyclopregnol, cyclopyrronium, cycloserine, eyelothiazide, cyclovalone, cyclotiamine, cycrimine, cyfluthrin, cyhalothrin, cyheptamide, cyheptropine, cynarine, cypenamine, cypermethrin, cypothrin, cyprazepam, cyprenorphine, cyprodenate, cyproheptadine, cyprolidol, cyproquinate, cyproterone, cyproximide, cyromazine, cysteamine, cysteine, cystine, cytarabine, cythiolate, dabelotine, dabigatran, dabuzalgron, dacarbazine, dacemazine, dacinostat, dacisteine, dacopafant, dactinomycin, dacuronium, dagapamil, daglutril, dalbavancin, dalbraminol, dalcotidine, daledalin, dalfopristin, dalteparin, daltroban, dalvastatin, dametralast, damotepine, danazol, daniquidone, danittracen, danofloxacin, danosteine, danthron, dantrolene, dapiprazole, dapitant, dapivirine, dapoxetine, dapsone, daptomycin, darbufelone, darenzepine, darglitazone, darifenacin, darodipine, darunavir, darusentan, dasantafil, dateliptium, daunorubicin, daxalipram, dazadrol, dazepinil, dazidamine, dazmegrel, dazolicine, dazopride, dazoquinast, dazoxiben, deboxament, debrisoquin, decamethonium, decimemide, decitabine, decitropine, declenperone, declopramide, decloxizine, decominol, decoquinate, dectaflur, deditonium, deferasirox, deferiprone, deferoxamine, deflazacort, defosfamine, defoslimod, degarelix, dehydroacetic acid, dehydrocholic acid, dehydroemetine, delanterone, delapril, delavirdine, delquamine, deergotrile, delfantrine, delfaprazine, selmadinone, delmetacin, delmpinol, delorazepam, deloxolone, delprostenate, deluceminne, dembrexine, demecarium, demeclocycline, demecolcine, demecycline, demegestone, demelverine, demexiptiline, democonazole, demoxepam, demoxytocin, denatonium, denaverine, denbufylline, denipride, denofungin, denopamine, denotivir, denpidazone, denufosol, denzimol, depelestat, depramine, depreotide, deprodone, deprostil, deptropine, dequalinium, deracoxib, deramciclane, deriglidole, derpanicaine, dersalazine, desapidin, desciclovir, descinolone, deserpidine, desipramine, deeslanoside, desloratidine, deslorelin, desmeninol, desmethylmoramide, desmopressin, desocriptine, desogestrel, desmorphine, desonide, desoximetasone, desoxycorticosterone, desvenlafaxine, detajmium, detanosal, deterenol, detirelix, detiviciclovir, detromidine, detorubicin, detrothyronine, devapamil, devazepide, dexamethasone, dexamisole, dexbrompheniramine, dexbudesonide, dexchlorpheniramine, dexclamol, dexecadotril, dexefaroxan, dexetimide, dexetozoline, dexfenfluramine, dexfosfoserine, dexibuprofen, deximafen, dexindoprofen, dexivacaine, dexketoprofen, dexlofexidine, dexloxiglumide, dexmedetomidine, dexmethylphenidate, dexnafenodonee, dexniguldipine, dexnorgestrel, dexormaplatin, dexoxadrol, dexpanthenol, dexpemedolac, dexpropranolol, dexproxibutene, dexrazoxane, dexsecoverine, dexsotalol, dextilidine, dextiopronin, dextofisopam, dextroamphetamine, dextrofemine, dextromethorphan, dextromoramide, dextrorphan, dextrothyroxine, dexcerapimil, sezaguanine, dezinamide, dezocine, diacerein, diacetamate, diacetolol, diamfenetide, diamocaine, diampromide, diamthiazole, diapamide, diarbarone, diathymosulfone, diatrizoate, diaveridine, diazepam, diaziquone, diazoxide, dibekacin, dibemethine, dibenzepin, dibenzothiophene, dibrompropamidine, bibromsalan, dibrospidium, dibucaine, dibuprol, dibupyrone, dibusadol, dicarbine, dicarfen, dichloralphenazone, dichloramine, dichlorisone, dichlormezanone, dichlorophen, dichlorphenarsine, dichloroxylenol, dichlorphenamide, dichlovos, diciferron, dicirenone, diclazuril, diclofenac, diclofenamide, diclofensine, diclofutrime, diclometide, diclonixin, dicloralurea, dicloxacillin, diclolinium, dicummol, dicyclomine, didanosine, didrovaltrate, dieldrin, dienestrol, dienogest, diethadione, diethylphthalate, diethylcarbamazine, diethylpropion, diethylstilbestrol, dethylthambutene, dietyltoluamide, dietifen, difebarbamate, difemerine, difemetorex, difenamizole, difencloxazine, difenoximide, difenoxin, difetarsone, difeterol, diflomotecan, diflorasone, difloxacin, difluanine, diflucortolone, diflumidone, diflunisal, difluprednate, diftalone, digitalis, digitoxin, digoxin, dihexyverine, dihydralazine, dihydrocodeine, dihydroergotamine, dihydrostreptomycin, dihydrotachysterol, diisobutylaminobenzoyloxypropyl theophylline, diisopromine, diisopropanolamine, diisopropylamine, dilazep, dilevalol, dilmefone, diloxanide, diltiazem, dimabefylline, dimadectin, dimecamine, dimeclonium, dimecrotic acid, dimefadane, dimefline, dimelazine, dimenhydrinate, dimenoxadol, dimepheptanol, dimepranol, dimepregnen, dimepropion, dimeprozan, dimesna, dimesone, dimetacrine, dimetamfetamine, dimethadione, dimethazan, dimethisoquin, dimethisterone, dimetholizine, dimethothizine, dimethoxanate, dimethylaminoethyl reserpilinate, dimethylthambutene, dimethyltubocurarinium, dimetipirium, dimetofrine, dimetridazole, diminazene, dimiracetam, dimoxamine, dimoxaprost, dimoxyline, dimpylate, dinaline, dinazafone, diniprofylline, dinitolmide, dinoprost, dinoprostone, dinsed, diohippuric acid, diosmin, diotyrosine, dioxadrol, dioxamate, dioxaphetyl butyrate, dioxation, dioxethedrin, dioxifedrine, dioxybenazone, dioxyline, dipenine, diperodon, diphemanil, diphenadione, diphenan, diphenchloxazine, diphenhydramine, diphenidol, diphenoxylate, diphenylpiperidinomethyldioxolan, diphenylpyraline, diphenoxazide, dipipanone, dipiproverine, dipivefrin, diprafenone, diprenorphine, diprobutine, diprofene, diprogulic acid, diproleandomycin, diprofylline, diproqualone, diproteverine, diprotrizoate, diproxadol, dipyridamole, dipyrithione, dipyrocetyl, dipyrone, diquafosol, dirithomycin, dirlotapide, disermolide, disquonium, disobutamide, sidofenin, sdisogluside, disopyramide, disoxaril, distigmine, disufenton, disulergine, disulfamide, disulfuram, disuprazoole, ditazole, ditekiren, ditercalinium, dithiaanine, ditiocade, ditiocarb, ditiomustane, ditolamide, ditophal, divabuterol, divalproex, divaplon, dixanthogen, dizatrifone, dizcilpine, dobesilate, dobupride, dobutamide, dobutamine, docarpamine, docebenone, docetaxel, doconazole, doconexent, docosanol, docusate, dodeclonium, dodicin, dofamium, dofequidar, dofetilide, dolasetron, doliracetam, domazoline, domiodol, domiphen, domipizone, domitroban, domoprednate, domoxin, domperidone, donepezil, donetidine, donitriptan, dopamantine, dopamine, dopexamine, dopropidil, doqualast, dorampimod, doramectin, doranidazole, dorastine, soreptidei, doretinel, doripenem, dorzolamide. dosergoside, dosmalfate, dotarizine, dotefonium, dothiepin, doxacurium, doxapram, doxaprost, doxazosin, doxefazepam, doxenitoin, doxepine, doxergocalciferol, doxibetasol, doxifluridine, doxofylline, doxorubicin, doxpicomine, doxycycline, doxylamine, drafiazine, dramedilol, draquinolo, drazidox, dribendazolew, drimidene, drobuline, drocinonide, droclidinium, drofenine, droloxifene, drometrizole, dromostanolone, dronabinol, drinedarone, dropempine, droperidol, droprenilamine, dropropizine, drospirenone, drotaverine, drotebanol, droxacin, droxicamide, droxicam, droxidopa, droxinavir, droxypropine, duazomycin, dulofibrate, duloxetine, dulozafone, dumorelin, dumetacin, duoperone, dupracetam, dutasteride, dyclonine, dyhydrogestrone, dymanthine, dyphylline, ebalzotan, ebastine, eberconazole, ebiratide, ebrotidine, ebselen, ecabapide, ecabet, ecadotril, ecalcidene, ecamsule, ecastolol, ecenofloxacin, echothiophate, eciprami-dil, eclanamine, eclazolast, ecomustine, econazole, ecopipam, ecraprost, ectylurea, edaglitazone, edaravone, edatrexate, edelfosine, edetol, edifolone, edogestrone, edonentan, edotecarin, edotreotide, edoxudine, edratide, edronocaine, edrophonium, efaproxiral, efaroxan, efavirenz, efegatran, efepristin, efetozole, efletirizine, eflornithine, efloxate, eflucimibe, elfumast, efonidipine, efrotomycin, eganoprost, eglumetad, egtazic acid, equalen, elacridar, elantrine, elanzepine, elaarofiban, elbanizine, eldacimibe, eletriptan, elfazepam, elgotipine, elinafide, eliprodil, elisartan, ellagic acid, elliptinium, elmustine, elnadipine, elopiprazole, elsamitrucin, eltanolone, eltenac, eltoprazine, elucaine, elvucitabine, elzasonan, elziverine, emakalim, emapunil, embramine, embusartan, embutramide, emedastine, emepronium, emetine, emeglitate, emilium, emiteflur, emiverine, emodepside, emopamil, emorfazone, emtricitabine, emylcamate, enadoline, enalapril, enalaprilat, enalkiren, enazadrem, enbucrilate, encamide, enciprazine, enclomiphene, encyprate, endixaprine, endomide, endralazine, endrysone, enecadin, enefexine, enestebol, enfenamic acid, enfluvirtide, englitazone, eniclobrate, enilconazole, enilospirone, eniluracil, eniporide, enisoprost, enloplatin, enocitabine, enofelast, enolicam, enoxacin, enoxamast, enoxaparin, enoximone, enoxolone, enipiprazole, enpiroline, enprazepine, enprofylline, enpromate, enprostil, enramycin, enrasentan, enrofloxacin, ensacillin, ensulizole, entacapone, entecavir, entsulfon, enviomycin, enviradene, enviroxime, enzacamene, anzastaurin, epalrestat, epanolol, eperezolid, eperisone, epervudine, ephedrine, epicamide, epicillin, epicriptine, epiestriol, epimestrol, epinastine, epinephrine, epinepheryl, epipropidine, epirizole, apiroprim, epirubicin, epitetracycline, epithiazide, epitiostanol, eplerenone, elivanserin, epoprostenol, epostane, eprazinone, eprinomectin, episteride, eprobemide, eprosartan, eprovafen, eproxindine, eprozinol, epsipranel, epaloprost, eptapirone, eptaplatin, eptastigmine, eptazocin, eptifibatide, equillin, erbulozole, erdosteine, ergo calciferol, ergonovine, ergotamine, eritoran, erizepine, erlotinib, ercamide, ersentilide, ertapenem, ertiprotafib, erythrity tetrnitrate, erythromycin, esafloxacin, esaprazole, esatenolol, escitalopram, esculamine, eseridine, esflurbiprofen, esketamine, escarbazepine, esmolol, esomeprazole, esonarimod, esorubicin, esoxybutynin, espatropate, esproquin, estazolam, estradiol, estramustine, estrazinol, estriol, estrofurate, estrone, estropipaten esupone, eszopclone, etabenzarone, etacepride, etafedrine, etafenone, etalocib, etamestrol, etaminile, etamiphylline, etamocycline, etanidazole, etanterol, etaqualone, etarotene, etasuline, etazepine, etazolate, etebenecid, eterobarb, etersalate, ethacridine, ethacrynic acid, ehtambutol, ethamivan, ethamsylate, ethaverine, ethenzameide, ethiazide, ethinamate, ethinyl estradiol, ethionamide, ethisterone, ethoheptazine, ethomoxane, ethonam, ethopabate, ethopropazine, ethosuximide, ethotoin, ethoxazene, ethoxazorutoside, ethoxzolamide, ethybenztropine, ethyl biscoumacetate, ethyl carfluzepate, ethyl cartrizoate, ethyl dibunate, ethyl dirazepate, ethyl loflazepate, ethylestrenol, ethylhydrocupreine, ethylmethylthiambutene, ethylmorphine, ethylnorepinepherine, ethylstilbamine, ethylnerone, ethylnodil, ethypicone, etibendazole, eticlopride, eticyclidine, etidocaine, etidronate, etidronic acid, etifelmine, etifenin, etifoxine, etilamfetamine, etilefrine, etilevodopa, etinidine, etipirium, etiprendol, etiproston, etiracetam, etiroxate, etisazole, etisomicin, etisulergine, etizolam, etocarlide, etocrylene, etodolac, etodroxizine, etofamide, etofenamate, etofenprox, etofibrate, etofermin, etofuradine, etofylline, etoglucid, eorolex, etolotifen, etoloxamine, etomidate, etomidoline, etomoxir, etomitazene, etonogestrel, etoperidone, etoposide, etoprindole, etoprine, etoricoxib, etorphine, etosalamide, etoxadrol, etoxeridine, etozolin, etrabamine, etravirine, etretinate, etriciguat, etryptamine, etymemazine, eucaine, eucalyptol, eugenol, euprocin, evandamine, evernimicin, everolimus, evicromil, exalamide, exametazime, examorelin, exaprolol, exatecan, exemestane, exepanol, exifone, exiprofen, exisulind, ezetimibe, ezlopitant, fadolmidine, fadrozole, falecalcitriol, falintolol, falipamil, falnidamol, famciclovir, famirapinium, famotidine, famotine, fampridine, famprofazone, fampronil, fananserin, fanapanel, fandofloxacin, fandosentan, fanetizole, fantofarone, fantridone, farglitazar, fasidotril, fasiplon, fasoracetam, faudil, fazadinium, fazarabine, febantel, febarbamate, febuprol, febuverine, febuxostat, feclemine, feclobuzone, fedotozine, fedrilate, felbamate, felbinac, felipyrine, felodipine, feloprentan, felypressin, femoxetine, fenabutene, fenacetinol, fenaclon, fenadiazole, fenaftic acid, fenalamide, femalcomine, fenamifuril, fenamole, fenaperone, fenbendazole, fenbenicillin, fenbufen, fenbutreazate, fencamfamin, fencibutirol, fenclexonium, fleclofenac, fenclonine, fenclorac, fenclozic acid, fendiline, fendizoate, fendosal, feneritrol, fenestrel, fenethazine, fenethylline, fenetradil, fenfiumizole, fenfluramine, flenfluthrin, fengabine, fenharmane, fenimide, feniodium, fenipentol, fenirfibrate, fenisorex, fenitrothion, fenleuton, fenmetozole, fenmetramide, fenobam, fenocinol, fenocitimine, fenofibrate, fenoldopam, fenoprofen, fenoterol, fenoerine, fenoxazoline, fenoxedil, fenozolone, fenpentadiol, fenperate, fenprpalone, fenpipramide, fenpiprane, fenpiverinium, fenprinast, fenproporex, fenprostalene, fenquiaone, fenretinide, fenspiride, fentanyl, fenthion, fentiazac, fenticlor, fenticonazolem, fentonium, fenvalerate, fenyripol, fepentolic acid, fepitrizol, fepradinol, feprazone, fepromide, feprosidnine, ferpifosate, fesoterodine, fetoxylate, fexicaine, fexinidazole, fexofenadine, fezatione, fezolamine, fiacitabine, fialuridine, fibracillin, fidarestat, fidexaban, fiduxosin, figopitant, filaminast, filenadol, filipin, finafloxacin, finasteride, fingolimod, fipamezole, fipexide, fipronil, firocoxib, flavamine, flavodic acid, flavodilol, flavoxate, flazalone, flecamide, flerobuterol, fleroxacin, flesinoxan, flestolol, fletazepam, flezelastine, flibanserin, flindokalner, flocalcitriol, floctafenine, flomoxef, floptopione, florantyrone, flordipine, floredil, florfenicol, florifenine, flosatidil, flosequinan, flosulide, flotrenizine, floverine, floxacillin, floxacrine, floxuridine, flucizine, flualamine, fluanisone, fluazacort, fluazuron, flubanilate, flubendazole, flubepride, flucarbril, flucetorex, flucindole, flucinprazine, flucloronide, fluconazole, flucrylate, flucytosine, fludalanine, fludarabine, fludazonium, fludeoxyglucose, fludiazepam, fludorex, fludoxopone, fludrocortisone, flufenamic acid, flufenisal, flufosal, flufylline, flugestone, fluindarol, fluindione, flumazenil, flimecinol, flumedroxone, flumequine, flumeridone, flumethasone, flumethiazole, flumetramide, flumexadol, flumezapine, fluminorex, flumizole, flumoxonide, flunamine, flunarizine, flunidazole, flunisolide, flunitrazepam, flunixin, flunoprost, flunoxaprofen, fluocinolone, fluocinonide, fluocortin butyl, fluocortolone, fluorescein, fluoresone, fluorodopa, fluorometholone, fluorosalan, fluorouracil, fluotracen, fluoxetine, fluoxymesterone, fluparoxan, flupentixol, fluperamide, fluperlapine, fluperolone, flupheazine, flupimazine, flupirtine, flupranone, fluprazine, fluprednidene, fluprednisolone, fluprofen, fluprofylline, fluproquazone, fluprostenol, fluquazone, fluradoline, flurandrenolide, flurantel, flurazepam, flurbiprofen, fluretofen, flurithromycin, fluorocitabine, fluorofamide, fluorogestone, flusoxolol, fluspiperone, fluspirilene, flutamide, flutazolam, flutemazepam, flutiazin, fluticasone, flutizenol, flutomidate, flutonidine, flutoprazepam, flutrimazole, flutroline, flutropium, fluvastatin, fluvoxamine, fluzinamide, fluzoperine, fodipir, folic acid, fomepizole, fomidacillin, fominoben, fomiversen, fomocaine, fonazine, fondaparinux, fopirtoline, forasartan, forfenimex, formebolone, formestane, formetorex, forminitrazole, formocortal, formoterol, forodesine, foropafant, fosamprenavir, fosarilate, fosazepam, fosenazide, fosfluconazole, fosfocreatinine, fosfomycin, fosfonet, fosfosal, fosfructose, fosinopril, fosinoprilat, fosmenic acid, fosmidomycin, fosopamine, fosphenyloin, fospirate, fosquidone, fostedil, fosrtriecin, fosveset, fotemustine, fortrenamine, fozivudine, frabuprofen, fradafiban, frakefamide, framycetin, frentizole, freselestat, fronepidil, fropenem, frovatriptan, froxiprost, ftaxilide, ftivazide, ftormetazine, ftorpropazine, fubrogonium, fudosteine, fuladectin, fulvestrant, fumagillin, fumoxicillin, fungimycin, fuprazole, furacrinic acid, furafylline, furalazine, furaltadone, furaprofen, furazabol, furazolidone, furazolium, furbicillin, furcloprofen, furegrelate, furethidine, furfenorex, furidarone, furmethoxadone, furnidipine, furobufen, furodazole, furofenac, furomazine, furomine, furosemide, furostilbestrol, fursalan, fursultiamine, furtherene, furtrethonium, fusafungine, fusidate, fusidic acid, fuzlocillin, gabapentin, gabapexate, gaboxadol, gacyclidine, gadobenate, gadobutrol, gadocolectic acid, gadodiamide, gadofosveset, gadomelitol, gadopenamide, gadopentetate, gadoteric acid, gadoteridol, gadoversetamide, gadoxetate, gadoxeticaicid, galamustine, galntamine, galarubicin, galasomite, galdansetron, gallamine triethiodide, gallopamil, galocitabine, galosemide, galtifenin, gamfexine, gamolenic acid, gamaxolone, ganciclovir, ganefromycin, ganglefene, ganstigmine, gantacurium, gantofiban, gapicomine, gapromidine, garenoxacin, gatifloxacin, gavestinel, geclosporin, gedocarnil, gefarnate, gefitinib, gemazocine, gemcabene, gemcadiol, gemcitabine, gemeprost, genfibtrozil, gemifloxacin, gemopatrilat, gentamicin, gepefrine, gepirone, geroquinol, gestaclone, gestadienol, gestodene, gestonorone, gestrinone, gevotroline, gimatecan, gimeracil, giparmen, giracodazole, giractide, girisopam, gitaloxin, gitoformate, glafenine, glaspimod, glatiramer acetate, glemanserin, glenvastatin, gliamilide, glibotnuride, glibutimine, glicaramide, glicetanide, gliclazide, glicondamine, glidazamide, glifiumide, glimepiride, glipalamide, glipizide, gliquidone, glisamuride, glisentide, glisindamine, glisolamide, glisoxepide, gloxazone, gloximonam, glucametacin, glucosamine, gluronolactone, glucuronamide, glunicate, glyburide, glybuthiazole, glubuzole, gycopyrrolate, glycylamide, glyhexamide, glymidine, glyoctamide, glyparamide, glypinamide, glyprothiazole, glysobuzole, goralatide, goserelin, gramicidin, granisetron, grepafloxacin, griseofulvin, guabenxan, guacetisal, guafecainol, guaiactamine, guaiapate, guaietolin, guaifenesin, guaimesal, guaisteine, guaithylline, guanabenz, guanacline, guanadrel, guanazodine, guanclofine, guancydine, guanethidine, guanfacine, guanisoquin, guanoclor, guanoctine, guanoxabenz, guanoxan, guanoxyfen, gusperimus, halazepam, halazone, halcinonide, halethazole, halobetasol, halocortolone, halofantrine, halofenate, halofuginone, halometasone, halonamine, halopemide, halopenium, haloperidol, halopredone, haloprogesterone, haloprogin, haloxazolam, haloxon, haloqionol, hamycin, hedaquinium, heliomycin, hepronicate, heptabarbital, heptaverine, heptolamide, hepzidine, heroin, hetacillin, hetaflur, heteronium, hexachlorophene, hexacyclonate, hexacyprone, hexadiline, hexafluorenium, hexamethonium, hexaminolevulinate, hexapradol, hexaprofen, hexapropymate, hexasonium, hexazole, hexedine, hexestrol, hexetidine, hexobarbital, hexobendine, hexocyclium, hexoprenaline, hexopyrronium, heylcaine, histamine, histapyrrodine, histidine, homarylamine, homatropine, homidium, homochlorcyclizine, homofenazine, homopipramol, homosalate, homprenorphine, hopantenic acid, hoquizil, hycanthone, hydracarbazine, hydralazine, hydragaphen, hydrobentizide, hydrochlorothiazide, hydrocodone, hydrocortisone, hydroflumethiazide, hydromadinone, hydromorphinol, hydromorphone, hydroquinone, hydroxyindasate, hydroxyindasol, hydro xocobalamin, hydroxyamphetamine, hydroxychloroquin, hydroxydione, hydroxypethidine, hydroxyphenamate, hydroxyprocaine, hydroxyprogesterone, hydroxypyridine tartrate, hydroxystenozole, hydroxystilbamidine, hydroxytetracaine, hydroxyzine, hymecromone, hyoscyamine, ibafloxacin, ibandronate, ibazocine, ibopamine, ibrolipim, ibrotamide, ibudilast, ibufenac, ibuprofen, ibuproxam, ibutamoren, ibuterol, ibutilide, ibuverine, icaridin, icatibant, iclaprim, icazepam, icodulinium, icofungipen, ifometasone, icopezil, icosapent, icospiramide, icotidine, icrocaptide, idarubicin, idaverine, idazoxan, idebenone, idenast, idoxifene, idoxuridine, idralfidine, idramantone, idraparinux, idrapril, idremcinal, idrociliamide, idronoxil, idropranolol, iferanserin, ifetroban, ifosfamide, ifoxetine, iganidipine, igmesine, iguratimod, ilaprazole, ilatreotide, ilepcimide, iliparcil, ilmofosine, iloomastat, ilonidap, iloperidone, imafen, imanixil, imatinib, imazodan, imcarbofos, imiclopazine, imidafenacin, imidapril, imidaprilat, imidocarb, imidoline, imidurea, imiglitazar, imiloxan, iminophenimide, imipenem, imipramine, imipraminoxide, imiquimod, imirestat, imitrodast, imolamine, imoxiterol, impacarzine, implitapide, impromidine, improsulfan, imuracetam, inamirone, inaperisone, incadronic acid, indacaterol, indacrinone, indalpine, indanazoline, indanidine, indanorex, indapamide, indatraline, indecamide, indeloxazine, indenolol, indibulin, indigotindisulfonate, indinavir, indiplon, indisetron, indobufen, indocate, indocyanine green, indolapril, indolidan, indomethacin, indopanolol, indopine, indoprofen, indoramin, indorenate, indoxole, indriline, inecalcitol, ingliforib, inicarone, inocterone acetate, inogatran, inosine, inositol, improquoone, intoplicine, intrazole, intriptyline, inulin, iobenguane, iobenzamic acid, iobitridol, iobutoic acid, icanlidic acid, iocarmic acid, iocetamic acid, iodamine, iodipamide, iodixanol, iodoantipyrine, iodocholesterol, iodohippurate, iodoquinol, iodothiouracil, idoxamic acid, iofetamine, ioflupane, iofratol, ioglicic acid, ioglucol, ioglunide, ioglycamic acid, iogulaamide, iohexyl, iolidonic acid, iolixanic acid, iolopride, iomazenil, iomeglamic acid, iomeprol, iomethin, iometopane, iomorinic acid, iopamidol, iopanoic acid, iopentol, iophendylate, iophenoxic acid, iopromide, iopronic acid, iopydol, iopydone, iosarcol, isofenamic acid, ioseric acid, iosimenol, iosimide, iosulamide, iosumetic acid, iotasul, ioteric acid, iothalamate, iothalamic acid, iotranic acid, iotriside, iotrizoic acid, iotrolan, iotroxic acid, iotyrosine, iovesol, ioxabrolic acid, ioxaglic acid, ioxilan, ioxitalamic acid, ioxotrizoic acid, iozomic acid, ipamorelin, ipazilide, ipenoxazone, ipexidine, ipidacrine, ipodate, iprgratine, ipramidil, ipratropium, ipravacaine, iprazochrome, ipriflavone, iprindole, ipocinidine, iproclozide, iprocrodol, iprofenin, iproheptine, iproniazide, ipronidazole, iproplatin, iprotiazem, iproxamine, iprozilamine, ipsalazide, ipsapirone, iquindamine, iralukast, irampanel, irbesartan, irindalone, irinotecan, irloxacin, irofulven, irolapride, iroxanadine, irsogladine, irtemazole, isalidole, isalsteine, isamfazone, isamoltan, isamoxole, isatoribine, isaxonine, isbogrel, isbufylline, ispamicin, isoamilinile, isobromindione, isobucaine, isobutamben, isocarboxazid, isoconazole, isocromil, isoetharine, isofiupredone, isofluorophate, isomazole, isomerol, isometamidium, isomethadone, isometheptene, isomolpan, isoamylamine, isoniazid, isonixin, isoprazole, isoprednidene, isoprofen, isopropamide, isopropicillin, isoproterenol, isosrbide, isospaglumic acid, isosulfan blue, isosulpride, isothipendyl, isotiquimide, isotretinoin, isoxaprolol, isoxepac, isoxicam, isoxsuprine, isradipine, israpafant, istrdefylline, itameline, itanoxone, itasetron, itazigrel, itopride, itraconazole, itriglumide, itrocamide, itrocinonide, iturelix, ivbradine, ivarimod, ivermectin, ivoqualine, ixabepilone, izonsteride, josamycin, kainic acid, kalafungin, kanamycin, kebuzone, keracyanin, ketamine, ketanserin, ketazocine, ketazolam, kethoxal, ketipramine, ketobemidone, ketocaine, ketocainol, ketoconazole, ketoprofen, ketorfanol, ketorolac, ketotifen, ketotrexate, khellin, khelloside, kitasamycin, labetalol, labradimil, lachesine, lacidipine, lacosamide, lactalfate, lactilol, lactulose, ladirubicin, ladostigil, laflunimus, lafutiine, laidlomycin propionate, lamifiban, lamivudine, lamotrigine, lamitidine, lanatoside, landiolol, lanepitant, lanicemine, laniquidar, lanoconazole, lanperisone, lanproston, lanreotide, lansoprazole, lapatinib, lapisteride, laprafylline, lapyrium, laquinimod, lasalocid, lasinavir, lasofoxifene, latanoprost, laudexium, laurcetium, laurocapram, lauroguadine, laurolinium, lauryl isoquinolinium, lavoltidine, lazabemide, lecimibide, ledazerol, ledoxantrone, lefetamine, leflunomide, lefradafiban, leiopyrrole, lemidosul, lemidipine, leminoprazole, lemoxinol, lemuteporfin, lanalidomide, lenampicillin, lenapenem, leniquisin, leuperone, leptacline, lercanidipine, lergotrile, lerisetron, lesoptiron, lestaurtinib, leteprinim, leteprinim, letimide, letosteine, letrazuril, letrozole, leucinocaine, leucocianidol, leucovorin, leurubicin, levalbuterol, levallorphan, levamfetamine, levamisole, levcromakalim, levcycloserine, levdobutamine, levemoamil, levetiracetam, levisoprenaline, levlofexidine, levmetamfetamine, levobetaxolol, levobunolol, levobupiacaine, levocabastine, levocamitine, levodopa, levodropropizine, levofacetoperane, levofenfluramine, levofloxacin, levofluraltadone, levoleucovorin, levomenol, levomepromazine, levomethadone, levomethadyl acetate, levomethorphan, levometiomeprazine, levomoprolol, levomoramide, levonantradol, levonordefrin, levonorgestrel, levophenacylmorphan, levopropoxyphene, levopropylcilline, levopropuylhexedrine, levoprotiline, levorin, levormeloxifene, levorphanol, levosalbutamol, levosemotiadil, levosimendan, levosulpiride, levothyroxine, levotofisopam, levoxadrol, lexipafant, lexithromycin, lexofenac, liarozole, libecillide, libenzapril, licarbazepine, licofelone, licostinel, lidadronic acid, lidamine, lidanserin, lidocaine, lidoferin, lidorestat, lifariaine, lifibrate, lifibrol, lilopristone, limaprost, limazocic acid, linarotene, lincomycin, lindane, linetastine, linezolid, linogliride, linopirdine, linotroban, lisinidomine, lintitript, lintopride, liothyronine, lipoic acid, liraglutide, liranaftate, lirequinil, lirexapride, lirimilast, liroldine, lisadimate, lisinopril, lisofylline, lisuride, litomeglovir, litoxetine, litracen, lividomycin, lixazinone, lixivaptan, lobapolatin, lobeline, lobendazole, lobenzarit, lobucavir, lobuprofen, locicortolone, lodaxaprine, lodazecar, lodelaben, lodenosine, Iodinixil, lodiperone, lodoxamide, lofemizole, lofendazam, lofentanil, lofepramine, lofexidine, loflucarban, lombazole, lomefloxacin, lomeguarib, lomerizine, lometraline, lometrexol, lomevactone, lomifylline, lomofungin, lomustine, lonafarnib, lonapalene, lonaprofen, lonazolac, lonidamine, loperamide, lopinavir, lopirazepam, lopobutan, loprazolam, loracarbef, lorajmine, lorapride, lorazepam, lorbamate, lorcamide, lorcinadol, loreclezole, lorglumide, lormetazepam, lornoxicam, lopiprazole, lortalamine, lorzafone, losartan, losigamone, losindole, losmiprofen, losoxantrone, losulazine, loteprednol, lotrafiban, lotrifen, lotucaine, lovastatin, loviride, loxanast, loxapine, loxiglumide, loxoprofen, loxoribine, lozilurea, lubazodone, lubeluzole, lubiprostone, lucanthone, lucartamide, lucimycin, lufenuron, lufironil, lufuradom, luliconazole, lumiracoxib, lupitidine, luprostiol, lurasidone, lurosetron, lurototecan, lusaperidone, luxabendazole, lydimycin, lymecycline, lynestrenol, lypressin, mabuprofen, mabuterol, maduramicin, mafenide, mafoprazine, mafosfamide, malathion, maleylsulfathiazole, malotilate, mangafodipir, manidipine, manifaxine, mannomustine, manozodil, mantabegron, mapinastine, maprotiline, maraviroc, marbofloxacin, maribavir, maridomycin, marimastat, mariptiline, maropitant, maroxepin, masoprocol, maxacalcitol, maytansine, mazapertine, mazaticol, mazindol, mazipredone, mazokalim, mebanazine, mebendazole, menbenoside, mebeverine, mebezonium, mebhydrolin, mebiquine, mebolazine, mebrofenin, mebutamate, mebutizide, mecamylamine, mecarbinate, mecetronium, meciadanil, mecinarone, meclinertant, meclizine, meclocycline, meclofenamaic acid, meclofenoxate, meclonazepam, mecloqualone, meclorisone dibutyrate, mecloxamine, mecobalamin, medazepam, medazomide, medetomidine, medibazine, medifoxamine, medorinone, medorubicin, medrogestrone, medronic acid, medroxalol, medroxyprogesterone acetate, medrylamine, medrysone, mefeclorazine, mefenamic acid, mefenidil, mefenidramium, mefenorex, mefeserpine, mefexamide, mefloquine, mefruside, megalomyciin, megestrol, megace, meglitinide, meglucycline, meglumine, meglutol, meladrizine, melagatran, melarsomine, melarsonyl, melarsoprol, meldonium, melengestrol acetate, meletimide, melevodopa, melinamide, melitracen, melizame, meloxicam, melperone, melphalan, melquinast, meluadrine, mamantine, memotine, menabitan, menadiol, menadione, menadoxime, menatetrenone, menbutone, menfegol, menglytate, menitrazepam, menoctone, menogaril, menobentine, mepazine, mepenzolate, meperidine, mephenesin, mephenoxalone, mephentermine, mephenyloin, mephobarbital, mebaral, mepindolol, mepiperphenidol, mepiprazole, mepiroxol, mepitiostane, mepivacaine, mepixanox, mepramidil, meprednisone, meprobamate, meprochol, meproscillarin, meprotixol, meprylcaine, meptazinol, mequidox, mequinol, mequitamium, mequitazine, meradimqate, menthyl anthranilate, merafloxacin, meralein, meralluride, merbaphen, merbromin, mercaptomerin, mercaptopurine, mercuderamide, mercufenol, mercumatilin, mergocriptine, meribendan, merimepodib, meropenem, mersalyl, mertialide, mesabolone, mesalamine, meseclazone, mesocarb, mesoridazine, mesipiperone, mespirenone, mestanolone, mesterolone, mestranol, mesudipine, mesulergine, mesulfamide, mesulfen, mesuprine, metabromsalan, metbutethamine, metabutoxycaine, metacetamol, metaclazepam, metacresol, metaglycodol, metahexamide, metalkonium, metalol, metamelfalan, metamfazone, metamfenpramone, metampicillin, metanixin, metapramine, metaproterenol, metaraminol, metaxalone, metazamide, metazide, matazocine, metbufen, meteneprost, metergoline, metergotamine, metescufylline, metesculetol, metesind, metethoheptazine, metformin, methacholine, methacycline, methadone, methadyl acetate, methallenestril, methallibure, methalthiazide, methamphetamine, methandriol, methandrostenolone, methaniazide, methantheline, methaphenilene, methapyrilene, methaqualone, metharbital, methastyridone, methazolamide, methdilazine, methenamine, methenolone, meheptazine, methestrol, methetoin, methikcillin, methimazole, methiodal, methiomeprazine, methionine, methisazone, methitural, methixene, methocarbamol, methocidin, methohexital, methopholone, methoprene, methoserpidine, methotrexate, methotrimeprazine, methoxamine, methoxsalen, methoxyphedrine, methoxyphenamine, methoxypromazine, methscopolamine, methsuximide, methyclothiazide, methyl aminolevulinate, methyl palmoxirate, methyl salicylate, methylatropine, methylbenactyzium, methylbenzethonium, methylcromone, methyldesorphine, methyldihydromorphine, methyldopa, methylene blie, methylephedrine, methylergometrine, methylergonovine, methylparaben, methylphenidate, methylprednisolone, methyltestosterone, methylthiouracil, methynodiol, methyprylon, methysergide, metiamide, metiapine, metiazinic acid, metibride, meticrane, metildigoxin, metindizate, metioprim, metioxate, metipirox, metiprenaline, metitepine, metizoline, metkephamid, metochalcone, metocinium, metoclopramide, metocurine, metofenazate, metogest, metolazone, metomidate, metopimazine, metopon, metoprine, metoprolol, metoquizine, metoserpate, metostilenol, metoxepin, metrafazoline, metralindole, metrazifone, metrenperone, metribolone, metrifonate, metrifudil, metrizamide, metrizoate, metronidazole, meturedepa, metyrapone, metyrosine, mevastatin, mexafylline, mexazolam, mexenone, mexiletine, mexiprosil, mexoprofen, mexrenoate, mezacopride, mezepine, mezilamine, mezlocillin, miaanserin, mibefradil, mibolerone, miboplatin, micafungin, miconazole, micronomicin, midaflur, midafotel, midaglizole, midamaline, midaxifylline, midazogrel, midazolam, midecamycin, midestein, midodrine, midostaurin, mifentidine, mifepristone, mifobate, miglitol, miglustat, mikamycin, milacamide, milacemide, milameline, milataxel, milenperone, milfasartan, milipertine, miloxacin, milrinone, miltefosine, milverine, mimbane, minalrestat, minamestane, minaprine, minaxolone, mindodilol, mindoperone, minepentate, minocromil, minocycline, minodronic acid, minopafant, minoxidil, mioflaazine, mipitroban, mipragoside, miproxifene, mirfentanil, mirincamycin, miripirium, miriplatin, mirisetron, miristalkonium, miroprofen, mirosamicin, mirostipen, mirtazapine, misonidazole, misoprostol, mitemcinal, mitiglinide, mitindomine, mitobronitol, mitocarcin, mitoclomine, mitocromin, mitoflaxone, mitogillin, mitoguazone, mitolactol, mitomalcin, mitomycin, mitonafide, mitopodozide, mitoquidone, mitosper, mitolane, mitotenamine, mitoxantrone, mitozolomide, mitradipide, mivacurium, mivobulin, mivotilate, mixidine, mizolastine, mizoribine, mobecarb, mobenzoxamine, mocimycin, mociprazine, moclonemide, moctamide, modafinil, modaline, modecamide, modipafant, moexipril, moexiprilat, mofarotene, mofebtazone, mofegiline, mofezolac, mofloverine, mofoxine, mofuisteine, molfarnate, molinazone, molindone, molracetam, molsidomine, mometasone, monalazone, monatepil, monesin, monobenzone, monoctanoin, monometacrine, monophosphothiamine, monoxerutin, montelukast, monterelin, moperone, mopidamol, mopidralazine, moprolol, moquizone, morantel, morazone, morclofone, morforex, moricizine, morinamide, morniflumate, morocromen, moroxydine, morpheridine, morphine, morsuximide, mosapramine, mosapride, motapizone, motexafin, motrazepam, motrtinide, moveltipril, moxadolen, moxalactam, moxaprindine, moxastine, moxaverine, moxazocine, moxestrol, moxicoumone, moxidectin, moxifloxacin, moxilubant, moxipraquine, moxirapine, moxisylate, moxnidazole, moxonidine, mozavaptan, mozenavir, mubritnib, mupirocin, murabutide, muraglitazar, mureletecan, murocamide, muzolimine, mycophenolic acid, myfadol, myrophine, myrtecaine, nabazenil, nabilone, nabitan, naboctate, nabumetone, nacartocin, nadide, nadiofloxacin, nadolol, nadoxolol, nafagrel, nafamostat, nafarelin, nafazatrom, nafcaproic acid, nafcillin, nafenodone, nafenopin, nafetolol, nafimidone, nafiverine, naflocort, nafomine, nafoxadol, nafoxidine, nafronyl, naftalofos, naftazone, naftifine, naftopidil, naftoxate, naftypamide, naglivan, nalbuphine, nalfurafine, nalidixic acid, nalmefene, nalmexone, nalorphine, naloxone, naltrexone, naminidil, naminterol, namirotene, namoxyrate, nanafrocin, nandrolone, nanterinone, nantradol, napactadine, napamezole, naphazaoline, naphthonone, napirimus, napitane, naproxime, naproxen, naproxol, napsagatran, naranol, narasin, naratriptan, nardeteterol, naroparcil, natamycin, nateglinide, navuridine, naxagolide, naxaprosteine, naxifylline, nealbarbital, nebantan, nebidrazine, nebivolol, neboglamine, nebracetam, nebramycin, necopidem, nedaplatin, nedocromil, nefazodone, nefiracetam, neflumozide, nefopam, nelarabine, neldazosin, nelezaprine, nelfinavir, neltenexine, nelzarabine, nemadectin, nemazoline, nemifitide, nemonapride, nemorubicin, neocinchophen, neomycin, neostigmine, nepadutant, nepafenac, nepaprazole, nepicastat, nepinalone, nequinate, neramexane, neraminol, nerbacadol, neridronic acid, nerisopam, nesapidil, nesiritide, nesosteine, nestifylline, neticonazole, netilmicin, netivudine, netobimin, netoglitazone, netupitant, neutramycin, neviparine, nexeridine, nexopamil, niacin, niacinamide, nialamide, niaprazine, nibroxane, nicafenine, nicainoprol, nicametane, nicanartine, nicaraven, nicarbazin, nicardipine, nicergoline, niceritol, niceverine, niclofolan, niclosamide, nicoboxil, nicoclonate, nicocodine, nicocortonide, nicocidodine, nicoduozide, nicofibrate, nicofuranose, nifurate, nicogrelate, nicomol, nicomorphine, nicopholine, nicoracetam, nicorandil, nicothiazone, nicotredole, nicoxamat, nictiazem, nictindole, nidroxyzone, nifedipine, nifekalant, nifenalol, nifenazone, niflumic acid, nifungin, nifiradene, nifuraldezone, nifuralide, nifuratel, nifuratrone, nifurdazil, nifurethazone, nifurfoline, nifurimide, nifurizone, nifurmazole, nifurmerone, nifuroquine, nifuroxazide, nifuroxime, nifurpipone, nifurpirinol, nifirprazine, nifurquinazol, nifursemizone, nifursol, nifurthiazole, nifurtimox, nifurtoinol, nifurvidine, nifurzide, nigludipine, nihydrazone, nikethamide, nileprost, nilprazole, niludipine, nilutamide, nilvadipine, nimazone, nimesulide, nimetazepam, nimidane, nimodipine, nimorazole, nimustane, neometacin, niperotidine, nipradilol, niprofazone, nitavoline, nirdazole, nisbuterol, nisobamate, nisoldipine, nisoxetine, nisterime, nitarsone, nitazoxanide, nitecapone, nithiamide, nitisinone, nitracrine, nitrafudan, nitralamine, nitramisole, nitraquazone, nitrazepam, nitrefazole, nitrendipine, nitrocefin, nitroclofene, nitrocycline, nitrodan, nitrofurantoin, nitrofurazone, nitromersol, nitromide, nitromifene, nitroscanate, nitrovin, nitroxinil, nitroxoline, nivazol, nivimedone, nizatidine, nizofenone, noberastine, nocloprost, nocodazole, nofecamide, nogalamycin, nolatrexed, nolinium, nolomirole, nolpitantium, nomegestrol, nomelidine, nomifensine, nonabine, nonaperone, nonapyrimine, nonathymulin, nonivamide, noracymethadol, norbolethone, norbudroine, norcholestenol, norclostebol, norcodeine, nordazepam, nordefrin, nordinone, norelgestromin, norepinepherine, norethandrolone, noethindrone, norethynodrel, noreximide, norfenefrine, norfloxacin, norgesterone, norgestimate, norgestomet, norgestrel, norgestrieneone, norletimol, norlevorphenol, normethadone, normorphine, norpipanone, nortetrazepam, nortopixantrone, nortriptyline, norvinisterone, nosantine, noscapine, nosiheptide, novobiocin, noxiptiline, noxytiolin, nuclomedone, nuclotixene, nufenoxole, nupafant, nuvenzepine, nylestriol, nylidrin, nystatin, obidoxime, ocaperidone, ocfentanil, ociltide, ocinaplon, octacaine, octafonium, octamoxin, octapinol, octatine, octaverine, octazamide, octenidine, octicizer, octimibate, octinoxate, octisalate, octocrylene, octodrine, octopamine, octotiamine, octreotide, octriptyline, octriazole, odalprofen, odapipam, odiparcil, ofloxacin, ofomine, oftasceine, oglufanide, olaflur, olamufloxacin, olanexidine, olanzapine, olaquindox, olcegepant, oleandomycin, oletimol, olmesartan, olopatadine, olpadronic acid, olpimedone, olprinone, olradipine, olsalazine, oltipraz, olvanil, omaciclovir, omapartrilat, omeprazole, omidoline, omigapil, omiloxetine, omoconazole, omonasteine, onapristone, ondansetron, ontazolast, ontianil, opanixil, opaviraline, opiniazide, opipramol, opratonium, orazamide, orazipone, orbofiban, orbutopril, orconazole, orientiparcin, oritavancin, orlistat, ormaplatin, ormeloxifene, ormetoprin, ornidazole, ornipreessin, ornithine, ornoprostil, orotic acid, orotirelin, orpanoxin, orphenadrine, ortataxel, orteteamine, osanetant, osaterone, oseltamivir, osemozotan, osmadizone, ospemifene, ostreogrycin, osutidine, otamixaban, otenzepad, oteracil, otilonium, otimerate, ouabain, oxabolon, oxabrexine, oxaceprol, oxacillin, oxadimedine, oxaflozane, oxaflumazine, oxagrelate, oxalinast, oxaliplatin, oxamarin, oxametacin, oxamisole, oxaminiquinem oxanamide, oxandrolone, oxantel, oxapadol, oxapium, oxaprazine, oxaprotiline, oxaprozin, oxcarbazole, oxatomide, oxazafone, oxazepam, oxazidone, oxazolam, oxazorone, oxcarbazepine, oxdralazine, oxeclosporin, oxedrine, oxeglitazar, oxeladin, oxendolone, oxepinac, oxetacillin, oxethazine, oxetorone, oxfendazole, oxfenicine, oxibendazole, oxibetaine, oxiconizole, oxidapamine, oxidronic acid, oxfentorex, oxifungin, oxigluttione, oxilofrine, oxilorphan, oximonam, oxindanac, oxiniacic acid, oxperomide, oxiracetam, oxiramide, oxisopred, oxisuran, oxitefonium, oxitriptan, oxitriptyline, oxtriponium, oxmetidine, oxodipine, oxogestone, oxolamine, oxolinic acid, oxomermazine, oxonazine, oxophenarsine, oxoprosto;l, oxpheneridine, oxprenoate, oxprenolol, oxtriphylline, oxbenzone, oxybutynin, oxychlorosene, oxycinchophen, oxyclipine, oxyclozanide, oxycodone, oxydipentonium, oxyfedrine, oxymesterone, oxymetazoline, oxymethalone, oxymorphone, oxypendyl, oxypertine, oxyphenbutazone, oxyphencyclimine, oxyphenisatin, oxyphenonium, oxypurinol, oxypurronium, oxyquinoline, oxyridazine, oxysonium, oxytetracycline, oxytocin, ozagrel, ozagamicin, ozolindone, paclitaxel, pacrindolol, pactimibe, padimate A, padimate Q, pafenolol, pagoclone, paldimycin, palinavir, paliperidone, palmidrol, palmoxirate, palonidipine, palonosertron, palosuran, pamabron, pamaqueside, pamaquin, pamicogrel, pamidronic acid, panadiplon, panamesine, pancopride, pancuronium, panipenem, panomifene, pantenicate, pantethine, panthenol, pantoprazole, panuramine, papverine, papveroline, parachlorphenol, parafiutizide, paramethadione, paramethasone acetate, paranitrosulfathiazole, paranyline, parapenzolate, parapropamol, pararosaniline, paraxazone, parbendazole, parcetasal, parconazole, parecoxib, pareptide, parethoxycaine, pargeverine, pargolol, pargyline, paricalcitol, paridocaine, parodilol, paromomycin, paroxetine, paroxypropione, parsalmide, particin, parvaquone, pasiniazid, pasireotide, patamostat, patupilone, paulomycin, paxamate, pazelliptine, pazinaclone, pazoxide, pazufloxacin, pecilocin, pecocycline, pefloxacin, pelanserin, peldesine, peliomycin, pelitinib, pelitrexol, pelretin, pelrinone, pelubiprofen, pemedolac, pemerid, pemetrexed, pemirolast, pemoline, penamecillin, penbutolol, penciclovir, pendecamine, pendetide, penfluridol, penflutizide, pengitoxin, penicillamine, penicillin G, penicillin V, penimepicycline, penimocycline, penirolol, penmesterol, penoctonium, penprostene, pentabamate, pentacynium, pentfluranol, pentagastrin, pentagestrone, pentalamide, pentamethonium, pentamidine, pentamorphone, pentamoxane, pentamustine, pentapiperide, pentapiperium, pentaquine, pentazocine, pentetic acid, pentreotide, penthienate, penthrichloral, pentiapine, pentifylline, pentigetide, pentisomicin, pentisomeide, pentizidone, pentobarbital, pentolinium, pentolonium, pentomone, pentopril, pentorex, pentosalen, pentostatin, pentoxifylline, pentoxyverine, pentrinitrol, pentylenetetrazol, peplomycin, pepstatin, peraclopone, peradoxime, perafensine, peralopride, peramivir, peraquisin, perastine, peratizole, perazine, perbufylline, perfomedil, perfosfamide, pegolide, perhexyline, periciazine, perifosine, perimetazine, perindopril, perindoprilat, perisoxal, perlapine, permethrin, perospirone, perphenazine, persilic acid, perzinfotel, petrichloral, pexantel, phanquone, phenacaine, phenacemide, phenacetin, phenactropinium, phenadoxone, phenaglycodol, phenamazoline, phenampromide, phenaphthazine, phenarsone, phenazocine, phenazopyridine, phenbutazone, phencarbamide, phencyclidine, phendimetrazine, phenelzine, phenerridine, phenethicillin, pheneturide, phenylglutarimide, phenicarbazide, phenindamine, phenindione, pheniprazine, pheniramine, phenisonone, phenmetrazine, phenobarbital, phenobutiodil, phenomorphan, phenothiazine, phenothrin, phenoxybenzamine, phenoxypropazine, phenprobamate, phenprocoumon, phenpromethamine, phensuximide, phentermine, phentolamine, phenyl aminosalicylic acid, phenylalanine, phenylbutazone, phenylephrine, phenylpropanolamine, phenylthiolone, phenyltoloxamine, phenyracillin, phenyramidol, phenyloin, pnetharbital, pholcodine, pholedrine, phoxim, phthalofyne, phthylsulfacetamide, phthalylsulfamethiazole, phthalylsulfathiazole, physostigmine. Phytic acid, phytonadione, pibaxizine, pibecarb, piberaline, piboserod, pibrozelesin, pibutidien, picafibrate, picartamide, picenadol, picilorex, piclamilast, piclonidine, piclopastine, picloxydine, picobenzide, picodralazine, picolamine, piconol, picoperine, picoplatin, picoprazole, picotamide, picotrin, picumast, picumeterol, pidobenzone, pidolacetamol, pidolicaicd, pidotimod, pifamine, pifinate, pifexole, piflutixol, piketoprofen, pildralazine, pilocarpine, pilsicamide, pimagedine, pimeclone, pimecrolimus, pimethylline, pimelautide, pimetacin, pimethixene, pimetine, imetremide, pimilprost, piminodine, pimobendan, pimonidazole, pimozide, pinacidil, pinadoline, pinafide, pinaverium, pinazepam, pincamide, pindolol, pinokalant, pinolcaine, pinoxepine, pioglitazone, pipacycline, pipamazine, pipamperone, pipazethate, pipebuzone, pipecuronium, pipemidicacid, pipendoxifene, pipenzolate, pipequaline, piperacetazine, piperacillin, piperamide, piperidolate, piperilate, piperocaine, piperonyl butoxide, piperoxan, piperphenidol, piperylone, pipobroman, pipoctanone, pipofezine, piposulfan, pipotiazine, pipoxizine, pipoxolan, pipradimadol, pipradrol, pipramadol, pipratecol, piprinhydrinate, pipocurarium, piprofurol, piprozolin, piquindone, piquizil, piracetam, pirandamine, pirarubicin, piraxelate, pirzmonam, pirazolac, pirbenicillin, pirbuterol, pirdonium, pirenoxine, pirenperone, pirezepine, pirepolol, piretanide, pirfenidone, pirbendil, piridicillin, piridocaine, piridoxilate, piridronic acid, pirifibrate, pirimiphos-ethyl, pirindazole, pirinixic acid, pirinixil, piriprost, piriqualone, pirisudanol, piritramide, piritrexin, pirlimycin, pirlindole, pirmagrel, pirmenol, pirnabine, piroctone, pirodavir, priodomast, pirogliride, piroheptine, pirolate, pirolazamide, piromidic acid, piroxantrone, piroxicam, piroxicillin, piroximone, pirozadil, pirprofen, pirquinozol, pirralkonium, pirsidomine, pirtenidine, pitenodil, pitofenone, pituxate, pivagabine, pivampicillin, pivenfrine, pivopril, pivoxazepam, pixantrone, pizotyline, plafbride, plaunotol, plauracin, pleconaril, pleuromulin, plevitrexed, plicamuycin, plomestane, pobilukast, podilfen, podofilox, poldine, polymixin, polythiazide, pomisartan, ponalrestat, ponazuril, ponfibrate, porfiromycin, posaconazole, posatirelin, posizolid, poskine, practolol, pradolfoxacin, prajmalium, pralatrexate, pralidoxime, pralmorelin, pralnacasan, pramipexole, pramiracetam, pramoxine, prampine, pranazepide, pranidipine, prankulast, pranolium, pranoprofen, pranosal, prasterone, prasugrel, pratosartan, pravadoline, pravastatin, praxadine, prazarelix, prazepam, prazepine, praziquantel, prazitone, prazocillin, prazosin, preclamol, prednazate, prednazoline, prednicarbate, prednimustine, prednisolamate, prednisolone, prednisone, prednival, prednylidene, pregabalin, pregnadiol, pregnenolone, premafloxacin, premazepam, prenalterol, prenisteine, prenoverine, prenoxdiazine, prenylamine, pretamazium, pretiadoil, prezatide, pribecaine, pridefine, prideperone, pridinol, prifelone, prifinium, prifuroline, pilocalne, primaperone, primaquine, primidolol, primidone, primycin, prinomastat, prinomide, prinoxodan, pristinol, pristinamycin, prizidilol, proadifen, probarbital, probenecid, probicromil, probucol, procainamide, procaine, procarbazine, procaterol, prochlorperazine, procinolol, procinonide, proclonol, procromil, procyclidine, procymate, prodeconium, prodilidine, prodipine, prodolic acid, profadol, profexalone, proflavine, proflazepam, progabide, progesterone, proglumetacin, proglumide, proheptazine, proligestone, praline, prolintane, prolonium, promazine, promegestone, promestriene, promethazine, promo late, promoxo lane, prontalol, propacetamol, propafenone, propagermanium, propamidine, propanidid, propanocaine, propantheline, proparacaine, propatyl nitrate, propazolamide, propenidazole, proprntofylline, propenzolate, properidine, propetamide, propetamfos, propetandrol, propicillin, propikacin, propinetidine, propiomazine, propiocaine, propiram, propisergide, propiverine, propizepine, propofol, propoxate, propoxur, propoxycaine, propoxyphene, propranolol, propyl docetrizoate, propyl gallate, propylhexedrine, propyliodone, propylthiouracil, propyperone, propyphenazone, propyromazine, proquazone, proquinolate, prorenoate, proroxan, prscillardin, prospidium, prostalene, prosulpride, prosultiamine, proterguride, protheobromine, prothipendyl, prothixene, protiofate, protionamide, protirelin, protizinic acid, protokylol, protoporphyrin, protriptyline, proxzole, proxibarbal, proxibutene, proxicromil, proxifezone, proxorphan, proxymetacaine, proxyphylline, prozapine, prucalopride, prulifloxacin, pruvanserin, pseudoephedrine, pumafentrine, pumaprazole, pumitepa, pumosetrag, puromycin, pyrabrom, pyrantel, pyrathiazine, pyrazinamide, pyrazofurin, pyricarbate, pyridarone, pyridinol, pyridofylline, pyridostigmine, pyridoxal, pyridoxamine, pyridoxine, pyrilamine, pyrimethamine, pyrimate, pyrinoline, pyrithione, pyrithyldione, pyritidium, pyritinol, pyrophenindane, pyrovalerone, pyroxamine, pyrrobutamine, pyrrocaine, pyrrolifene, pyrroliphene, pyrrolnitrin, pyroxane, pyrvinium, pytamine, quadazocine, quadrosilan, quatacaine, quazepam, quazinone, quazodine, quazolast, quetiapine, quifenadine, quiflapon, quillifoline, quilostigmine, quinacainol, quinacillin, quinacrine, quinagolide, quinaldine blue, quinapril, quinaprilat, quinazosin, quibolone, quincarbate, quindecamine, quindonium, quindoxin, quinelorane, quinestradol, quinestrol, quinethazone, quinetolate, quinezamide, quinfamide, quingestanol acetate, quingestrone, quinidine, quinine, quinotolast, quinpirole, quinterenol, quitiofos, quinuclium, quinupramine, quinupristin, quipazine, quisultazine, rabeprazole, raclopride, ractopamine, radafaxine, rafoxanide, ragaglitazar, ralitoline, raloxifene, raltitrexed, raluridine, ramatroban, ramciclane, ramelteon, ramifenazone, ramipril, ramiprilat, ramixotidine, ramnodigin, ramnoplanin, ramorelix, ramosetron, ranelic acid, ranimustine, ranimycin, ranirestat, ranitidine, ranolaine, rapacuronium, rasagiline, rasburicase, rathyronine, ravuconazole, razaxaban, razinodil, razobazam, razoxane, rebimastat, reboxetine, recainam, reclazepam, regadenoson, reglitazar, relcovaptan, relomycin, remacemide, remifentanil, remikiren, remiprostol, remoxipride, renanolone, rentiapril, renzapride, repaglinide, reparixin, repinotan, repirinast, repromicin, reproterol, rescimetol, rescinnamine, resequinil, reserpine, resiquimod, resocortol butyrate, resorantel, resorcinol, retapamulin, retelliptine, retigabine, retinol, revaprazan, revatropate, revenast, reviparin, revizinone, revospirone, ribavirin, riboflavin, riboprine, ribostamuycin, ricasetron, ridazolol, ridogrel, rifabutin, rifalazil, rifametane, rifamexil, rifamide, rifampin, rifapentine, rifaximin, rilapine, rilmakalim, rilmazafone, rilmenidine, rilopirox, rilozarone, rilpovorine, riluzole, rimantadine, rimazolium, rimcazole, rimexolone, rimiterol, rimonabant, rimoprogin, riodipine, rioprostil, ripazepam, ripisartan, risarestat, risedronicacid, risocaine, risotilide, rispenzepine, risperidone, ristianol, ristocetin, ritanserin, ritometan, ritipenem, ritobegron, ritodrine, ritolukast, ritonavir, ritropirronium, ritrosulfan, rivaroxaban, rivastigmine, rivoglitazone, rizatriptan, robalzotan, robenidine, rocastine, rocepafant, rociclovir, rocuronium, rodocaine, rodorubicin, rofecoxib, rofelodine, rofleponide, roflumilast, rogletimide, rokitamycin, rolafagrel, roletamide, rolgamidine, rolicyclidine, rolicyprine, rolipram, rolitetracycline, rolodine, rolziracetam, romazarit, romergoline, romifenone, romifidine, romurtide, ronactolol, ronidazole, ronifibrate, ronipamil, runnel, ropinirole, ropitoin, ropivacaine, ropizine, roquinimex, rosaprostol, rosaramicin, rose bengal, rosiglitazone, rosoxacin, rostafuroxin, rostaporfin, rosterolone, rosuvastatin, rotamicillin, rotigotine, rotoxamine, rotaxate, roxadimate, roxarsone, roxatidine acetate, roxibolone, roxifiban, roxindole, roxithromycin, roxolonium, roxoperone, rubitecan, ruboxistaurin, rufinamide, rufloxacin, rupatadine, rupintrivir, rutamycin, ruvazone, ruzadolane, sabarubicin, sabcomeline, sabeluzole, sabiporide, saccharin, safingol, safirinol, sagandipine, salacetamide, salafibrate, salantel, salazodine, salazosulfadimidine, salazosulfamide, salazosulfathiazole, salcaprozoic acid, salcolex, salethamide, salflucerine, salicyl alcohol, salicylamide, salicylic acid, salinazid, salinomycin, salmefamol, salmeterol, salmisteine, salnacedin, salprotoside, salsalate, sameridine, samixogrel, sampatrilat, sampirtine, sancycline, sanfetrinem, sanguinarium, saperconazole, saprisartan, sapropterin, saquinavir, sarafloxacin, sarakalim, saralasin, sarcolysin, sardomozide, saredutant, saripedem, sarizotan, sarmazenil, samoxicillin, sarpicillin, sarpogrelate, saterinone, satigrel, satranidazole, satraplatin, saviprazole, savoxepin, scopafungin, scopinast, scopolamine, secalciferol, seclazone, secnidazole, secobarbital, securinine, sedecamycin, sedoxantrone, seganserin, segesterone, seglitide, selamectin, selgiline, selfotel, soldenoson, selprazine, sampimod, sematilide, semaxanib, semduramicin, semorphone, semotiadil, semustine, senazodan, seocalcitol, sepazonium, seperidol, sepimostat, seprilose, seproxetine, sequifenadine, seratrodast, serazapine, serfibrate, sergolexole, sermetacin, sertindole, sertraline, setastine, setzindol, setipafant, setiptiline, setoperone, sevitropium, sevopramide, sezalamide, sagoside, sibenadet. Sibopirdine, sibrafiban, sibutramine, siccanin, sifrprazine, siguazodan, silandrone, sildenafil, silibinin, silcristin, sildianin, silodosin, silodrate, silperisone, siltenzepine, simendan, simetride, simfibrate, simtrazene, simvastatin, sincalide, sinefungin, sinitrodil, sintropium, sipatrigine, siramesine, siratiazem, sirolimus, sisomicin, sitafloxacin, sitalidone, sitamaquine, sitaxentan, sitofibrate, sitoglusoide, sivelestat, soblidotin, sobuzoxane, solabegron, solifenasin, solimastat, solpecainol, solypertine, somatadine, soneclosan, sonepiprazole, sopitazine, sopromidine, soquinolol, sorafenib, soraprazan, sorbinicate, sorbinil, sorivudine, sornidipine, sotalol, soterenol, spaglumic acid, sparfloxacin, sparfosate, sparsomycin, sparteine, spectinomycin, spiclamine, spiperone, spiradoline, spiramide, spiramycin, spirapril, spiraprilat, spirendolol, spirgetine, spirilene, spiriprostil, spirofylline, spirogermanium, spiroglumide, spiromustine, spironolactone, spiroplatin, spirorenone, spirotriazine, spiroxasone, spiroxatrine, spiroxepin, spizofurone, sprodiamine, squalamine, squalane, stacofylline, stllimycin, stannsoprfin, stanolone, stanoaolol, stavudine, stearylsufamide, steffimycin, stenbolone, strpronin, stercuronium, stevaladil, stibamine, stibophen, stilbamidine, stilbazium, stilonium, strimazole, stiripentol, stirocamide, stirofos, streptomycin, streptonicozid, streptonigrin, streptozocin, styramine, subathiazone, subendazole, succinylcholine, succinylsulfathiazole, succisulfone, suclofenide, sucralfate, sucralose, sucrose octaacetate, sucrosufate, sudexanox, sudoxicam, sufenatil, sufotidine, sufugolix, sugammadex, sulamserod, sulazepam, sulazuril, sulbactam, sulbenicillin, sulbenox, sulbentine, sulbutiamine, sulclamine, sulconazole, sulfabenz, sulfabenzamide, sulfabromomethazine, sulfacarbamide, sulfacecole, sulfacetamide, sulfachlorpyridazine, sulfachrysoidine, sulfaclomide, sulfaclorazole, sulfaclozine, sulfacytine, sulfadiazine, sulfadimethoxine, sulfadoxine, sulfaethidole, sulfaguanidine, sulfaguanole, sulfalene, sulfaloxic acid, sulfamazone, sulfamerazine, sulfameter, sulfamethaziine, sulfamethizole, sulfamethoxazole, sulfamethoxypyridazine, sulfametmidine, sulfametrole, sulfamonomethoxine, sulfamoxole, sulfanilamide, sulfanilate, sulfaanitran, sulfaperin, sulfaphenazole, sulfaproxyline, sulfapyridine, sulfaquinoxaline, sulfarsphenamine, sulfasalazine, sulfasomizole, sulfasuccinamide, sulfasymazine, sulfathiazole, sulfathiourea, sulfatolamide, sulfatroxazole, sulfatrozole, sulfazamet, sulfinaolol, sulfinpyrazone, sulfuram, sulfisomidine, sulfisoxazole, sulfobromophthalein, sulfonterol, sulforidazine, sulfosalicylic acid, sulfoxone, sulcrinat, sulindac, sulisatin, sulisobenzone, sulmarin, sulmazole, sulmepride, sulnidazole, sulocarbilate, suloctidil, sulodexide, sulofenur, sulopenem, sulosemide, sulotroban, suloxifen, sulpiride, sulprosal, sulprostone, sultamicillin, sultiame, sultopride, sultosilic acid, sultroponium, sulukast, sulverapride, sumacetamol, sumanirole, sumarotene, sumatriptan, sumetizide, sunagrel, suncillin, sunepitron, supidimide, supalast, suproclone, suprofen, suramin, suricamide, suriclone, suritozole, suronacrine, susalimod, suxemerid, suxethonium, suxibuzone, symclosene, synetine, tabilautide, tabimorelin, tacalcitol, tacapenem, tacedinaline, taclamine, tacrine, tacrolimus, tadalafil, tafluposide, taglutamine, tagorizine, talampanel, talampicillin, talaporfin, talastine, talbutal, taleranol, talibegron, talinolol, talipexole, talisomycin, tallimustine, talmetacin, talmetoprim, talnetant, talniflumate, talopram, talsalate, toloximine, talsaclidine, talsupram, taltirelin, taltobulin, taltrimide, taludipine, talviraline, tameridone, tameticillin, tametraline, tamibarotene, tamitinol, tanolarizine, tamoxifen, tampramine, tamsulosin, tanaproget, tandamine, tandospirone, tandutinib, taniplon, tanomastat, tapentadol, taprizosin, taprostene, tarazepide, tariquindar, tasosartan, tasuldine, taurolidine, tauromustine, tauroselcholic acid, taurosteine, tazadolene, tazanolast, tazarotene, tazasubrate, tazeprofen, tazifylline, taziprinone, tazobactam, tazofelone, tazolol, tazometine, tebanicline, tebatizole, tebipenem, tebufelone, tebuquine, tecadenoson, tecalcet, tecastemizole, teclthiazide, teclozan, tedisamil, tefazoline, tefenperate, teflufazine, tefiutixol, tegafur, tegaserod, teglicar, teicopanin, telavancin, telbivudine, telenzepine, telinavir, telithromycin, telmesteine, telmisartan, teloxantrone, teludipine, temafloxacin, temarotene, tematropium, temazepam, temefos, temelastine, temiverine, temocapril, temocaprilat, temocillin, temodox, temoporfin, temozolomide, temisirolimus, temurtide, tenamfetamine, tenatoprazole, tendamistat, tenidap, tenilapine, teniloxazine, tenilsetam, teniposide, tenivastatin, tenocyclidine, tenofovir, tenofovir disoproxil, tenonitrozole, tenosal, tenosiprol, tenoxicam, tenylidone, teoprantil, teoprolol, tepirindole, tepoxalin, teprenone, teprotide, terazosin, terbequinil, terbinafine, terbogrel, terbucromil, terbufirol, terbuficin, terbuprol, terbutaline, terciprazine, terconazole, terdecamycin, teerestigmine, terfeadine, terfiavoxate, terfuranol, terguride, teriflunomide, terikalant, terizidone, terlakiren, terlipressin, ternidazole, terodiline, terofenamate, teroxalene, teroxirone, tertatolol, tesaglitazar, tesicam, tesimide, tesimilifene, tesofensine, testolactone, testosterone, tetomilst, tetrabarbital, tetrabenazine, tetracaine, tetracycline, tetrahydrozoline, tetramethrin, tetramisole, tetraxetan, tetrazepam, tetrazolast, tetriprofen, tetrofosmin, tetronasin, tetroquinone, tetroxoprin, tetrydamine, teverelix, texacromil, tezacitabine, tezosentan, thalidomide, thebacon, thenalidine, thenium, thenyldiamine, theobromine, theodrenaline, theofibrate, theophylline, thiabendazole, thiacetarsamide, thialbarbital, thiamazole, thiamine, thiamiprine, thiamphenicol, thamylal, thiazesim, thiazinamium, thiazolsulfone, thiethyperazine, thihexinol ethylbromide, thimerfonate, thimerosal, thiocolchicoside, thioctic acid, thiofuradene, thioguanine, thiohexamide, thioinosine, thiopental, thiophanate, thiopropazate, thioproperazine, thioridazine, thiosalan, thiostrpton, thiotepa, thiotetrabarbital, thiothixene, thiphenamil, thiphencillin, thiram, thonzonium, thonzylamine, thozalinone, threonine, thymocartin, thymoctonan, thymol, thymopentin, thymotrinan, thyromedan, thyropropic acid, thyroxin, tiacrilast, tiadenol, tiafibrate, tiagabine, tiamenidine, tiametomnium, tiamulin, tianafac, tianeptine, tiapamil, tiapirinol, tiapride, tiaprofenic acid, tiaprost, tiaramide, tiazofurin, tiazuril, tiabalosin, tibeglisene, tibenelast, tibenzate, tibezonium, tibolone, tibric acid, tibrofan, ticabesine, ticalopride, ticarbodine, ticarcillin, ticlatone, ticlopidine, ticolubant, ticrynafen, tidembersat, tidiacic acid, tiemonium, tienocarbine, tienopramine, tienoxolol, tifemoxone, tifenazoxide, tiflamizole, tiflorex, tifluadom, tiflucarbine, tiformin, tifurac, tigecycline, tigemonam, tigestol, tigloidine, tilargenine, tiletamine, tilidine, tiliquinol, tilisolol, tilmacoxib, tilmicosin, tilnoprofen, tilomisole, tilorone, tilozepine, tilsuprost, tiludonic acid, timcodar, timefurone, timegadine, timelotem, timepidium, timiperone, timirdine, timobesone acetate, timofibrate, timolol, timonacic, timoprazole, tinabinol, tinazoline, timidazole, tinisulpride, tinofedrine, tinoridine, tiocarlide, tioclomarol, tioconazole, tioctilate, tiodazosin, tiodonium, tiomergine, tiomesterone, tioperidone, tiopinate, tiopronin, tiopropamine, tiospirone, tiotidine, tiotropium, tioxacin, tioxamast, tioxaprofen, tioxidazole, tioxolone, tipentosin, tipepidine, tipetropium, tipifarnib, tipindole, tipranavir, tipredane, tiprenolol, tiprinast, tiprodil, tiprostanide, tiportimod, tiqueside, tiquinamide, tiquizium, tiracizine, tirapazamine, tiratricol, tirilazad, tirofiban, tiropramine, tisartan, tisocalcitate, tisocromide, tisopurine, tisoquone, tivanidazole, tiviciclovir, tivirapine, tixadil, tixanox, tixocortol, tizabrin, tizanidine, tizolemide, tizoprolic acid, tobicillin, toborinone, tobramycin, tocamide, tocamphyl, tocladesine, tocofenoxate, tocofibrate, tocophersolan, todralazine, tofenacin, tofetridine, tofimilast, tofisoline, tofisppam, tolafentrine, tolamolol, tolazamide, tolboxane, tolbutamide, tolvapone, tolciclate, toldimfos, tolfamide, tolfenamic acid, tolgabide, tolimidone, tolindate, toliodium, toliprolol, tolmesoxide, tometin, tolnaftate, tolnapersine, tolnidamine, toloconium, tolonidine, tolonium, toloxatone, toloxychlorinol, tolpadol, tolpentamide, tolperisone, tolpiprazole, tolpronine, tolpropamide, tolpyrramide, tolquinzole, tolrestat, tolterodine, toltrazuril, tolufazepam, tolvaptan, tolycaine, tomeglovir, tomelukast, tomoglumide, tomoxiprole, tonabersat, tonazocine, topilutamide, topiramate, topixantrone, topotecan, toprilidine, topterone, toquizine, torbafylline, torcetrapib, torcitabine, toremifene, toripristone, torsemide, tosagestin, tosifen, tosufloxacin, tosulur, trabectedin, traboxopine, tracazolate, tradecamide, tralonide, tramadol, tramazoline, trandolapril, trandolaprilat, tranexamic acid, tranilast, transcamide, trantelinium, tranycypromine, trapencaine, trapidil, travoprost, traxanox, traxoprodil, trazitiline, trazium, trazodone, trazolopride, trebenzomine, trecadrine, trecetilide, trefentanil, trelnarizine, treloxinate, trenbolone, trengestone, trenizine, treosulfan, trepibutone, trepipam, trepirium, treprostinil, treptilamine, terquisin, tresperimus, trestolone, trethinium, trethocanoic acid, tretinoin, tretinoin tocoferil, tretoquinol, triacetin, triafungin, triamcinolone, triamcinolone acetonide, triamcinolone benetonide, triamcinolone furetonide, triampyzine, triamternem triaziquone, triazolam, tribendilol, tribenoside, tribromsalan, tribuzone, tricaprilin, tricetamide, trichlorfon, trichlormethiazide, trichlomethine, triciribine, triclabendazole, triclacetamol, triclazate, triclobisonium, triclocarban, triclodazol, triclofenol, triclofos, triclofyllin, triclonide, triclosan, tricyclamol, tridihexethyl, tridolgosir, trientine, triethylenemelamine, trifenagrel, trifezolac, triflocin, triflubazam, triflumidate, triflomeprazine, trifluperazine, trifluperidol, triflupromazine, trifluidine, triflusal, trifosmin, trigevolol, trihexylpheidyl, triletide, trilostane, trimazosin, trimebutine, trimecain, trimedoxime, trimegestone, trimeperidine, trimeprazine, trimetazidine, trimethadone, trimethamide, trimethaphan, trimethidinium, trimethobenzamide, trimethoprim, trimetozine, trimetrexate, trimexiline, trimipramine, trimoprostil, trimoxamine, trioxifene, trioxsalen, tripalmitin, tripamide, triparanol, tripelennamine, triplatin, triprolidine, triptorelin, tritoqualine, trixolane, trizoxime, trocimine, troclosene, trodusquemine, trofosfamide, troglitazone, troleandomycin, tromanttadine, tropabazate, tropanserin, tropapride, tropatepine, tropenziline, tropicamide, tropigline, tropirine, tropisetron, tropodifene, troquidazole, trospectomycin, trospium, trovafloxacin, trovirdine, troxacitabine, troxerutin, troxipide, troxolamide, troxonium, troxypyrrolium, truxicurium, truxipicurium, tryparsamide, tubocurarine, tubulozole, tucaresol, tuclazepam, tulathromycin, tulobuterol, tulopafant, turosteride, tuvatidine, tybamate, tylosin, tymazolin, tyropanoate, tyrosine, tyrothricin, ubenimex, ubidecarenone, ubisindine, ufenamate, ufiprazole, uldazepam, ulifloxacin, uliprisnil, umespirone, undecylenic acid, unoprostone, upenazime, upidosin, uracil, uracil mustard, urapidil, uredepa, uredofos, urefibrate, ursodiol, urulcholic acid, utibapril, utibaprilat, vadocaine, valaciclovir, valconazole, valdecoxib, valdetamide, valdipromide, valethamate, vlaganiciclovir, valine, valnemulin, vlanoctamide, valofane, valomaciclovir, valperinol, valproate, vlaproicacid, valpromide, valrocemide, valrubicin, valsartan, valorcitabine, valtrate, vamicamide, vancomycin, vandetanib, vaneprim, vanitiolide, vanoxerine, vanyldisulfamide, vapiprost, vapreotide, vardenfanil, varenicline, varespladib, vatalanib, vatanidipine, vebufloxacin, vecuronium, vedaclidine, vedaprofen, velaresol, velnacrine, venlafaxine, venritidine, verodoline, veralipride, verapamil, verazide, verilopam, verlukast, verofylline, versetamide, verteporfin, vesnarinone, vestipitant, vetrabutine, vidarabine, vigabatrin, vilazodone, vildaglipin, viloxazine, vinbarbital, vinblastine, vinburnine, vincamine, vincanol, vincofos, vinconate, vincristine, vindeburnol, vindesine, vinpidine, vinflunine, vinformide, vinfosiltine, vinglycinate, vinleucinol, vinleurosine, vinmegallate, vinorelbine, vinpocetine, vinpoline, vinrosidine, vintiamol, vintoperol, vintriptol, vinylbital, vinzolidine, viomycin, viprostol, viqualine, viquidil, virginiamycin, viridofulvin, viroxime, visnadine, visnafylline, vofopitant, voglibose, volazocine, volpristin, voriconazole, vorozole, voxergolide, xaliproden, xamoterol, xanomeline, xanoxic acid, xanthinol, xantifibrate, xantocillin, xantofyl palmitate, xemilofiban, xenalipin, xenazoic acid, xenbucin, xenipentone, xenothiorate, xenygloxal, xenylhexenicacid, xenylropium, xibenolol, xibornol, xidecaflur, xilobam, ximelagatran, ximoprofen, ximidamine, xinomiline, sipamide, xipranolol, xorphanol, xylamidine, xylazine, xylocoumarol, xylometazoline, xyloxemine, yohimbic acid, zabicipril, zabiciprilat, zacopride, zafirlukast, zafuleptine, zalcitabine, zalderide, zaleplon, zalospirone, zalitidine, zaltoprofen, zamifenacin, zanamivir, zanapezil, zankiren, zanoterone, zapizolam, zaprinast, zardaverine, zatebradine, zatosetron, zelandopam, zenarestat, zenazocine, zeniplatin, zepastine, zeranol, zetidoline, zidapamide, zidometacin, zidovudine, zifrostilone, zilantel, zilascorb, zileuton, zilpaterol, zimeldine, zimiidoben, zindotrine, zindoxifene, zinconazole, zinostatin, zinterol, zinviroxime, zipeprol, ziprsidone, zocainone, zofenopril, zofenoprilat, zoficonazole, zolamine, zolasartan, zolazepam, zolendronic acid, zolenzepine, zolertine, zolimidine, zoliprofen, zolmitriptan, zoloperone, Zolpidem, zomebazam, zomepirac, zometapine, zonampanel, zoniclezole, zoniporide, zonisamide, zopiclone, zopolrestat, zorbamycin, zorubicin, zosuquidar, zotepine, zoticasone, zoxazolamine, zucapsaicin, zuclomiphene, zuclopenthixol, zylofuramine, or the like, or a combination comprising at least one of the foregoing pharmaceutical or veterinary compounds.

Algaecides may also be disposed upon the pattern or blended in with the material used to form the pattern. Examples of suitable algaecides are 2,2-dibromo-3-nitrilopropionamide (DNP), methylene bis-thiocyanate (MBT), 5-chloro-2-methyl-4-isothiazolin-3-one/2-methyl-4-isothiazol in-3-one (CMI), tetrahydro-3,5-dimethyl-2H, 1,3,5-thiadiazine-2-thione (TDD), sodium dimethyldithiocarbamate/sodium ethylene bis dithiocarbamate (SDT), alkyl dimethylbenzyl amonium chloride family, poly[oxyethylene (dimethyliminio)ethylene (dimethyliminio)ethylene dichloride, copper sulfate, or the like, or a combination comprising at least one of the foregoing algaecides.

In one embodiment, the biologically active agents may be encapsulated in microballoons and incorporated into the pattern as part of the drug coating. In another embodiment, the biologically active agents may be encapsulated in microballoons and incorporated on the surface of the pattern or incorporated into the channels that form the tortuous pathway. The microballoons may serve to release the drugs gradually over a period of time. In other words the pattern can serve as a time-release coating for the drugs. In one embodiment, the pattern can release drugs after being subjected to a stress.

The inorganic materials used in the spaced features and/or the surface can comprise ceramics and/or metals. The inorganic materials can comprise inorganic oxides, inorganic carbides, inorganic nitrides, inorganic hydroxides, inorganic oxides having hydroxide coatings, inorganic carbonitrides, inorganic oxynitrides, inorganic borides, inorganic borocarbides, or the like, or a combination comprising at least one of the foregoing inorganic materials. Examples of suitable inorganic materials are metal oxides, metal carbides, metal nitrides, metal hydroxides, metal oxides having hydroxide coatings, metal carbonitrides, metal oxynitrides, metal borides, metal borocarbides, or the like, or a combination comprising at least one of the foregoing inorganic materials.

Examples of suitable inorganic oxides include silica ($SiO_2$), alumina ($Al_2O_3$), titania ($TiO_2$), zirconia ($ZrC_2$), ceria ($CeO_2$), manganese oxide ($MnO_2$), zinc oxide (ZnO), iron oxides (e.g., FeO, $\gamma$-$Fe_2O_3$, $Fe_3O_4$, or the like), calcium oxide (CaO), manganese dioxide ($MnO_2$ and $Mn_3O_4$), or combinations comprising at least one of the foregoing inorganic oxides. Examples of inorganic carbides include silicon carbide (SiC), titanium carbide (TiC), tantalum carbide (TaC), tungsten carbide (WC), hafnium carbide (HfC), or the like, or a combination comprising at least one of the foregoing carbides. Examples of suitable nitrides include silicon nitrides ($Si_3N_4$), titanium nitride (TiN), or the like, or a combination comprising at least one of the foregoing. Examples of suitable borides are lanthanum boride ($LaB_6$), chromium borides (CrB and $CrB_2$), molybdenum borides ($MoB_2$, $Mo_2B_5$ and MoB), tungsten boride ($W_2B_5$), or the like, or combinations comprising at least one of the foregoing borides. Exemplary inorganic substrates are those that comprise naturally occurring or synthetically prepared silica and/or alumina. Metals used in the spaced features and/or the surface can be transition metals, alkali metals, alkaline earth metals, rare earth metals, or the like, or a combination comprising at least one of the foregoing metals. Examples of metals are iron, copper, aluminum, tin, tungsten, chromium, gold, silver, titanium, or a combination comprising at least one of the foregoing metals.

The pattern can be aligned such that linear channels between respective features in a pattern can be arranged to be perpendicular and/or parallel to an average direction of fluid flow, when the pattern is disposed on a surface that contacts a flowing fluid. In one embodiment, the pattern may be disposed on the substrate so that the linear channels between respective features in a pattern can be arranged to occupy an angle of 1 to about 360 degrees, specifically about 5 to about 270 degrees, and more specifically about 10 to about 200 degrees, and more specifically about 20 to about 200 degrees with respect to the average direction of fluid flow.

In one embodiment, the pattern can be dynamically modified during use. In other words, the surface can comprise a material such as, for example, a shape memory alloy, a shape memory polymer, a magnetorheological fluid, an electrorheological fluid, and the like, that can be activated when desired to either inhibit or to facilitate bioadhesion.

In an exemplary embodiment, when the pattern comprises an organic polymer, the organic polymer can be filled with an electrically conducting filler thereby making the surface electrically conductive. By passing an electrical signal to the surface, the pattern can be heated and consequently the dimensions of the features and those of the patterns can be changed during use.

Although not required to practice the present invention, Applicants not seeking to be bound by the mechanism believed to be operable to explain the efficacy of the present invention, provide the following. The efficacy of surfaces according to the invention is likely to be due to physically interfering with the settlement and adhesion of microorganisms, such as algae, bacteria and barnacles. Properly spaced features (such as "ribs") formed on or formed in the surface can be effective for organisms from small bacteria (<1 µm, such as 200 to 500 nm), to large tube worms (>200 µm, such as 200 to 500 µm), provided the feature spacing scales with the organism size. Specifically, bioadhesion is retarded when the specific width of closely packed, yet dissimilar features (e.g. ribs) in the pattern is too narrow to support settlement on top, yet the ribs are too closely packed to allow settlement in between. However, a feature spacing too small is believed to make the surface look flat to the settling organism, i.e. like the base surface, and thus ineffective. Accordingly, a feature spacing that scales with 25 to 75% of the settling organism's smallest physical dimension has been found to be generally effective to resist bioadhesion. Various different surface topographies can be combined into a hierarchical multi-level surface structure to provide a plurality of spacing dimensions to deter the settlement and adhesion of multiple organisms having multiple and wide ranging sizes simultaneously, such as algae, spores and barnacles.

Topographies according to the invention can generally be applied to a wide variety of surfaces for a wide variety of desired applications. Applications for inhibiting bioadhesion using the invention described in more detail below include base articles used in marine environments or biomedical or other applications which may be exposed to contamination by biological organisms, such as roofs on buildings, water inlet pipes in power plants, catheters, cosmetic implants, and heart valves. As described below, surfaces according to the invention can be formed on a variety of devices and over large areas, if required by the application.

Barnacles are known to be generally elliptically shaped have a nominal length of about 100 µm, and a nominal width of about 30 µm. Algae are also generally elliptically shaped and have a nominal length of about 7 µm, and a nominal width of about 2 µm, while spores are generally elliptically shaped have a nominal length of about 5 µm, and a nominal width of about 1.5 µm. Features according to the invention are generally raised surfaces (volumes) which emerge from a base level to provide a first feature spacing, or in the case of hierarchical multi-level surface structures according to the invention also include the a second feature spacing being the spacing distance between neighboring plateaus, which themselves preferably include raised features thereon or features projected into the base article.

As noted above, if the feature spacing is smaller than the smaller dimension of the organism or cell, it has been found that the growth is generally retarded, such between 0.25 and 0.75 of the smaller dimension of the cell or organism. A feature spacing of about ½ the smaller dimension of a given organism to be repelled has been found to be near optimum. For example, for an algae spore 2 to 5 µm in width, to retard adhesion, a feature spacing of from about 0.5 to 3.75 µm, preferably 0.75 to 2 µm is used. For example, to repel barnacles 20 to 50 µm in width, a feature spacing of between 5 and 200 µm, preferably 10 to 100 µm, has been found to be effective. For repelling both barnacles and spores, a hierarchical multi-level surface structure according to the invention can include a raised surfaces (volumes) which emerge from or are projected into a base level having a feature spacing of about 2 µm, and a plurality of striped plateau regions spaced 20 µm apart, the plateau regions also including raised surfaces (volumes) which emerge from or are projected into the plateau having a spacing of about 2 µm. One or more additional plateau regions can be used to repel additional organisms having other sizes. The additional plateau regions can be aligned (parallel) with the first plateau, or oriented at various other angles.

Although generally described for deterring bioadhesion, the invention can also be used to encourage bioadhesion, such as for bone growth. Feature dimensions of at least equal to about the size of the larger dimension of bioorganism or cells to be attached have been found to be effective for this purpose.

Although the surface is generally described herein as being an entirely polymeric, the coating can include non-polymeric elements that contribute to the viscoelastic and topographical properties. A "feature" as used herein is defined a volume (L, W and H) that projects out the base plane of the base material or an indented volume (L, W and H) which projects into the base material. The claimed architecture is not limited to any specific length. For example, two ridges of an infinite length parallel to one another would define a channel in between. In contrast, by reducing the overall lengths of the ridges one can form individual pillars. Although the surface is generally described as a coating, which is generally a different material as compared to the base article, as noted above, the invention includes embodiments where the coating and base layer are formed from the same material, such as provided by a monolithic design, which can be obtainable by micromolding.

In the case of a surface coating, the coating can comprise a non-electrically conductive material, defined as having an electrical conductivity of less than $1\times10^{-6}$ S/cm at room temperature. The coating layer can comprise elastomers, rubbers, polyurethanes and polysulfones. The elastic modulus of the coating layer can be between 10 kPa and 10 MPa. In the case of 10 to 100 kPa materials, the coating can comprise hydrogels such as polyacrylic acid and thermo sensitive hydrogels such as poly isopropylacrylamide. The coating layer can be various thicknesses, such as 1 µm to 10 mm, preferably being between 100 µm to 1 mm.

Each of the features have at least one microscale dimension. In some embodiments, the top surface of the features are generally substantially planar. Although feature spacing has been found to be the most important design parameter, feature dimensions can also be significant. In a preferred embodiment of the invention, each of the features includes at least one neighboring feature having a "substantially different geometry". "Substantially different geometry" refers to at least one dimension being at least 10%, more preferably 50% and most preferably at least 100% larger than the smaller comparative dimension. The feature length or width is generally used to provide the substantial difference.

The feature spacing in a given pattern should generally be consistent. Studies by the present Inventors have indicated that small variations in micrometer scale spacing of the ribs that compose the surface features have demonstrated that less than 1 µm changes (10% or less than the nominal spacing) can significantly degrade coating performance. For example, the consistency of a 2 µm nominal spacing should be within ±0.2 µm for best retardation of *Ulva* settlement.

The composition of the patterned coating layer may also provide surface elastic properties, which also can provide some bioadhesion control. In a preferred embodiment when bioadhesion is desired to be minimized, the coated surface distributes stress to several surrounding features when stress is applied to one of the features by an organism to be repelled from the surface.

The roughness factor (R) is a measure of surface roughness. R is defined herein as the ratio of actual surface area ($R_{act}$) to the geometric surface area ($R_{geo}$); $R=R_{act}/R_{geo}$. An example is provided for a 1 cm² piece of material. If the sample is completely flat, the actual surface area and geometric surface area would both be 1 cm². However if the flat surface was roughened by patterning, such as using photolithography and selective etching, the resulting actual surface area becomes much greater that the original geometric surface area due to the additional surface area provided by the sidewalls of the features generated. For example, if by roughening the exposed surface area becomes twice the surface area of the original flat surface, the R value would thus be 2.

The typography generally provides a roughness factor (R) of at least 2. It is believed that the effectiveness of a patterned coating according to the invention will improve with increasing pattern roughness above an R value of about 2, and then likely level off upon reaching some higher value of R. In a preferred embodiment, the roughness factor (R) is at least 4, such as 5, 6, 7, 8, 9, 10 11, 12, 13, 14, 15, 16, 17, 18, 19, 20, 25 or 30. Assuming deeper and more closely spaced features can be provided, R values can be higher than 30.

FIG. 1(a) is a scanned SEM image of an exemplary "Sharklet" topography according to an embodiment of the invention sized to resist algae adhesion and growth. The Sharklet topography is based on the topography of a shark's skin. Shark skin is a prominent example of a low friction surface in water. Unlike real shark skin which has fixed topographical feature dimensions based on the species, the Sharklet topography is scalable to any topographical feature dimension including feature width, feature height, feature geometry, and spacing between features. The composition of real shark skin is limited to the natural composition of the skin. The Sharklet topography according to the invention can be produced in a variety of material including synthetic polymers, ceramics, and metals, as well as composites.

The Sharklet and related topographies according to the invention can be described quantitatively using two sinusoidal functions. This description is provided below.

Figure 13:
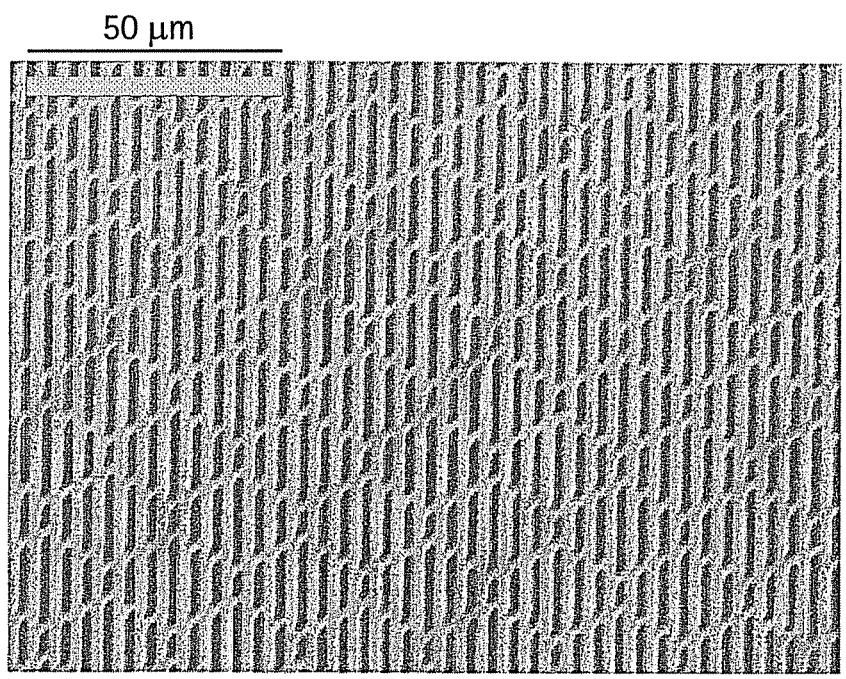
FIG. 13 is a photograph showing a pattern having nanometer sized features.

Surface layer comprises a plurality of features 111 which are attached to and project out from base surface 130. Base surface 130 can be a roofing material, the inner surface of a water inlet pipe for a power or water treatment plant, an implantable medical device or material, such as a breast implant, a catheter or a heart valve. Each of the features 111 have at least one microscale dimension, with a width of about 3 μm, lengths of from about 3 to about 16 μm, and a feature spacing of about 1.5 μm. The thickness (height) of features 111 comprising coating layer is about three (3) microns. The first feature spacing can be less than or equal to about 200 nanometers as can be seen in the FIG. 13.

Features adjacent to a given feature 111 generally provide substantially different dimensions, in the arrangement shown in FIG. 1(a), feature lengths. The top surface of the features is shown as being planar. The patterned coating layer generally resists algae as compared to a generally planar base surface as described in the Examples and shown in FIGS. 8(a)-(c).

FIG. 1(b) is a scanned optical profilometry image of a pattern having a plurality of features 161 projecting into a base surface 180, according to another embodiment of the invention. Features 161 comprise indented void volumes into base surface 180. Although not shown, a surface can include regions having raised features 111 shown in FIG. 1(a) together with regions having indented features 161 shown in FIG. 1(b).

The composition of the patterned surface shown in FIGS. 1(a) and 1(b) is generally a polymer such as polymethylsiloxane (PDMS) elastomer SILASIC T2® provided by Dow Corning Corp, which is an elastomer of a relative low elastic modulus. The features 111 need not be formed from a single polymer. Features can be formed from copolymers and polymer composites. In another embodiment, the surface or coating comprises of a material such as, steel or aluminum, or a ceramic. The coating layer is also typically hydrophobic, but can also be neutral or hydrophilic.

As noted above, the patterned surface layer may also provide surface elastic properties which can influence the degree of bioadhesion directly, an in some cases, also modulate surface chemistry of the surface layer. It is believed that a low elastic modulus of the patterned coating layer tends to retard bioadhesion, while a high elastic modulus tends to promote bioadhesion. A low elastic modulus is generally from about 10 kPa and 10 MPa, while a high elastic modulus is generally at least 1 GPa.

The patterned surface can be formed or applied using a number of techniques, which generally depend on the area to be covered. For small area polymer layer applications, such as on the order of square millimeters, or less, techniques such as conventional photolithography, wet and dry etching, and ink-jet printing can be used to form a desired polymer pattern. When larger area layers are required, such as on the order of square centimeters, or more, spray, dipcoat, hand paint or a variant of the well known "applique" method be used. These larger area techniques would effectively join a plurality of smaller regions configured as described above to provide a polymer pattern over a large area region, such as the region near and beneath the waterline of a ship.

A paper by Xia et al entitled "Soft Lithography" discloses a variety of techniques that may be suitable for forming comparatively large area surfaces according to the invention. Xia et al. is incorporated by reference into the present application. These techniques include microcontact printing, replica molding, microtransfer molding, micromolding in capillaries, and solvent-assisted micromolding, which can all generally be used to apply or form topographies according to the invention to surfaces. This surface topography according to the invention can thus be applied to devices as either a printed patterned, adhesive coating containing the topography, or applied directly to the surface of the device through micromolding.

Another tool that can be used is the Anvik HexScan® 1010 SDE micro lithography system which is a commercially available system manufactured by Anvik Corporation, Hawthorne, N.Y. 10532. Such a tool could be used to produce surface topographies according to the invention over a large area very quickly. It has a 1 micron resolution which can produce our smallest pattern at a speed of approximately 90 panels (10" by 14") per hour.

FIGS. 2(a)-(d) illustrate some exemplary architectural patterns (unit cells) that can be used with the invention. FIG. 2(a) shows a riblet pattern fabricated from PDMS elastomer having features spaced about 2 μm apart on a silicon wafer. The features were formed using conventional photolithographic processing. FIG. 2(b) shows a star/clover pattern, FIG. 2(c) a gradient pattern, while FIG. 2(d) shows a triangle/circle pattern.

FIG. 3 provides a table of exemplary feature depths, feature spacings, feature widths and the resulting roughness factor (R) based on the patterns shown in FIGS. 2(a)-(d). Regarding the riblet pattern shown in FIG. 2(a) for the depth, spacing and widths shown, the resulting pattern roughness factor (R) ranged from 5.0 to 8.9. Similar data for the star/clover pattern (FIG. 2(b)), gradient pattern (FIG. 2(c)), and triangle/circle (FIG. 2(d)) are also shown in FIG. 3. Regarding the triangle/circle arrangement (FIG. 2(d)), for a feature depth of 10 μm, feature spacing of 1 μm, and feature width of 1 μm (circles) and 5 μm (triangles), a roughness factor (R) of 13.9 is obtained.

Figure 4A:
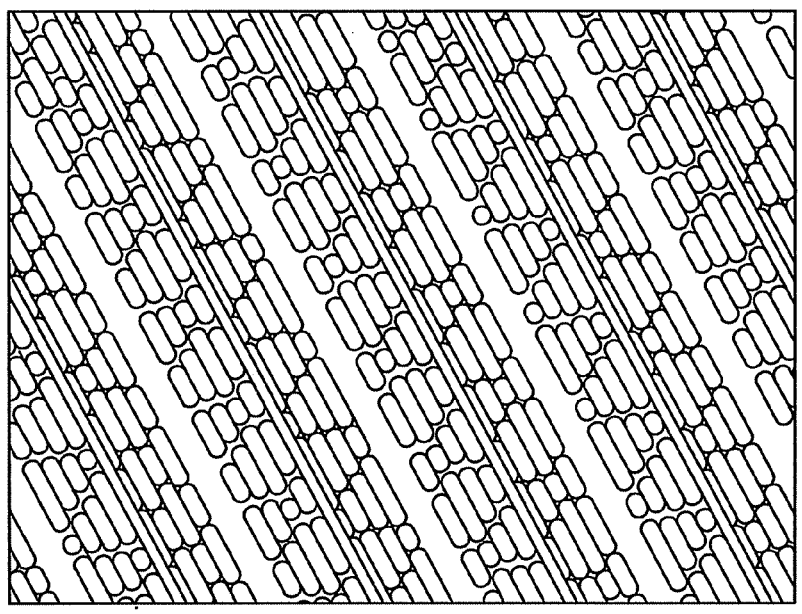
FIG. 4(a) is a is a scanned SEM image of an exemplary hierarchical surface topography according to an embodiment of the invention.

FIG. 4(a) is a scanned SEM image of an exemplary hierarchical (multi-layer) surface architecture according to an embodiment of the invention. The first feature spacing distance of about 2 μm between features 412 and its neighboring features including feature 411 is for deterring a first organism, or organism in a size range of about 5 μm, or less. For example, as noted above, an algae spore is nominally 5 μm wide. A patterned second layer comprising a plurality of striped plateau regions 420 is disposed on the first layer. A spacing distance between elements of the plateau layer provides a second feature spacing, which is substantially different as compared to the first feature spacing. As used herein, a "substantially different spacing distance" is at least 50% larger, and is preferably at least 100% larger than the smaller first feature spacing distance. In FIG. 4, the architecture shown provides a spacing distance between the second pattern strips of about 20 μm, or about 900% greater than the first spacing distance. The 20 μm spacing is approximate ½ the width (smallest dimension) of a nominal barnacle thus repelling barnacles. Thus, hierarchical (multi-layer) surface architectures according to the invention can simultaneously repel multiple organisms covering a significant range of sizes.

Figure 4B:
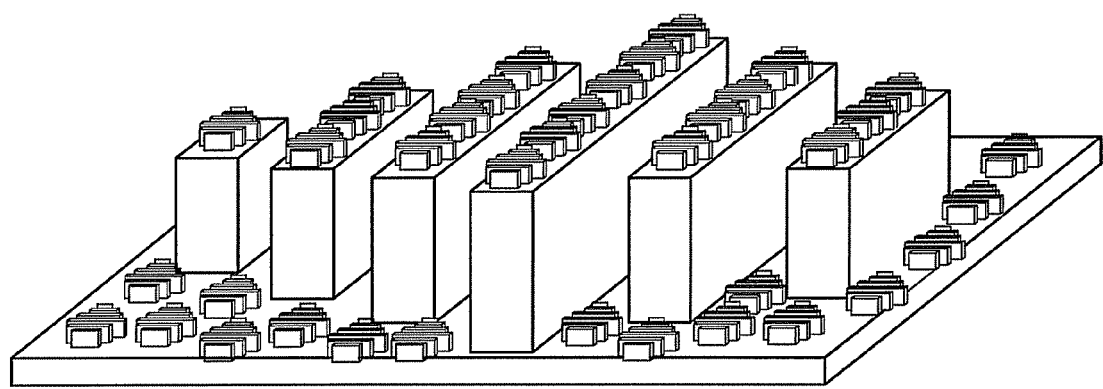
FIG. 4(b) is a depiction of another exemplary hierarchical surface topography according to an embodiment of the invention comprising a first plurality of spaced features upon which are disposed a second plurality of spaced features.

In one embodiment, the hierarchical surface architecture comprises a first plurality of spaced features upon which are disposed a second plurality of spaced features. FIG. 4(b) depicts a hierarchical surface architecture comprising a first plurality of spaced features upon which are disposed a second plurality of spaced features. The spaced features of the first plurality of spaced features arranged in a plurality of groupings. The groupings of the first plurality of spaced features comprise repeat units. The spaced features within a grouping being spaced apart at an average distance of about 1 nanometer to about 500 micrometers. Each feature may have a surface that is substantially parallel to a surface on a neighboring feature. In one embodiment, each feature may have a surface that is not parallel to a surface on a neighboring feature. Each feature is separated from the neighboring features. The groupings of features are arranged with respect to one another so as to define a tortuous pathway; the plurality of spaced features provide the article with an engineered roughness index of about 5 to about 30.

The second plurality of spaced features are disposed upon the first plurality of spaced features. The spaced features of the second plurality of spaced features are arranged in a plurality of groupings. The groupings of features of the second plurality of spaced features comprise repeat units. The spaced features within a grouping being spaced apart at an average distance of about 1 nanometer to about 50 micrometers; specifically at an average distance of about 10 nanometer to about 30 micrometers; and more specifically at an average distance of about 20 nanometer to about 10 micrometers. The groupings of features in the second plurality of spaced features are arranged with respect to one another so as to define a tortuous pathway; the plurality of spaced features providing the article with an engineered roughness index of about 5 to about 30. The second plurality of spaced features may have disposed thereon a third plurality of spaced features, and so on.

In one embodiment of the invention, the surface topography is a topography that can be numerically represented using at least one sinusoidal function. In the paragraphs below, a sinusoidal description of Sharklet and related topographies is provided. The Sharklet and related topographies can be numerically representing using two (2) sinusoidal waves. A general equation is provided which the only topographical restriction is that two elements with at least a one dimensional length discrepancy must be selected and periodic throughout the structure. The smallest feature of the two being related to the size of the smallest dimension (the width) of the organism of interest. All the elements and features in-between and/or around the two periodic features become irrelevant. Examples of each of these instances are presented and the generalized equation is then developed. In one embodiment, with reference to FIG. 1(a), it may be seen that the adjacent groupings of features are spaced apart from each other to define an intermediate sinusoidal pathway. It may further be seen by reference to FIG. 1(a) that neighboring sinusoidal paths converge toward and diverge from each other in a substantially mirror symmetry.

The Sharklet shown in FIG. 1(a) will be used for this example. The dimensions are not relevant as this point. The Sharklet shown in FIG. 1(a) is a 4-C element (repeating) structure.

FIG. 5(a) shows a sinusoidal wave beginning at the centroid of the smallest of the four Sharklet features. By inspection of the periodicity of the Sharklet features, a sine wave of the form y=A sin(wx) can be used to describe this periodicity as shown in FIG. 5(a). It can be noticed that the repeating structure above the section described by the sine wave is out of phase from that structure by 90 degrees or n/2 radians, which happens to be a cosine wave. That periodicity and packing can be represented using a cosine wave in the form y=B+A cos(wx) (as shown in FIG. 5(b)).

The entire surface area of the topography can be numerically represented by a numerical summation of both sinusoidal waves in the form:

$$y = cN + A\sin(wx)$$

$$y = cN + B + A\cos(wx) \text{ where } N = 0, 1, 2, 3 \ldots n$$

The area of coverage of the topography is thus described by the limits of n and x.

The Sharklet and related topographies can thus be defined by the following limitations:

(i) Two geometric features of at least one dimensional discrepancy must be periodic throughout the structure.

(ii) The smallest of the two geometric features is related to the smallest dimension of the fouling organism or cell of interest.

(iii) In a standard Cartesian coordinate system represented by x and y, with the origin positioned at start of each sin and cosine wave, the smaller of the two features is periodic where the waves cross y=0. The waves pass through the area centroid of the feature @ y=0.

(iv) In a standard Cartesian coordinate system represented by x and y with the origin positioned at start of each sine and cosine wave, the larger of the two features is periodic where the waves cross reaches it's maximum amplitude. The wave intersects the center of the tallest part of the feature @ y=max and the x-moment of inertia of the feature @ y=0.

General Form of Sinusoids $$y = cN + A\sin(wx)$$

$$y = cN + B + A\cos(wx)$$

where N=0, 1, 2, 3 ... n

The following equations define the values for the variables A, B, c and w:

$$A = (\tfrac{1}{2}) * (L_D)$$

$L_D$=y-dimension of larger of two elements $$B = (\tfrac{1}{2}) * (S_D) + (P_S) + (\tfrac{1}{2}) * (L_D)$$

$S_D$ y-dimension of smaller of two elements
$P_S$=y-spacing between the two elements after packing
$c = L_D + 2*(P_S) + S_D$
$w = 2\pi f = (2\pi)/(T) \rightarrow w$: angular frequency (rad), f: frequency (Hz), T: wave period $$T = 2 * X_D$$

Figure 6A:
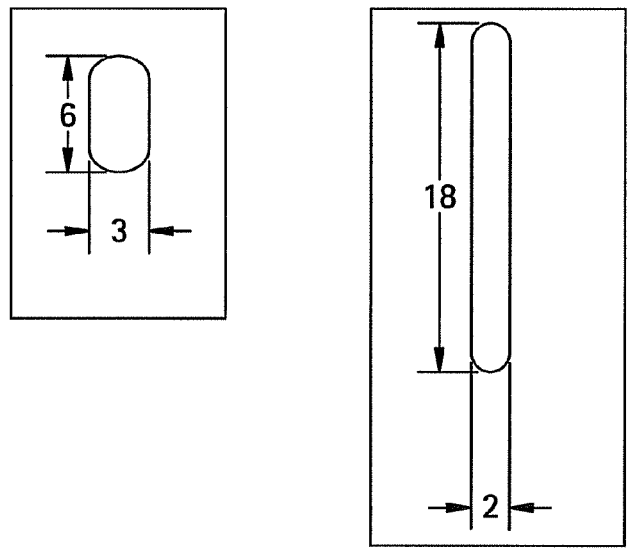
FIG. 6(a) shows two (of four) exemplary Sharklet elements, element 1 and element 2; the element 1 and element 2 have different lengths and widths.
Figure 6B:
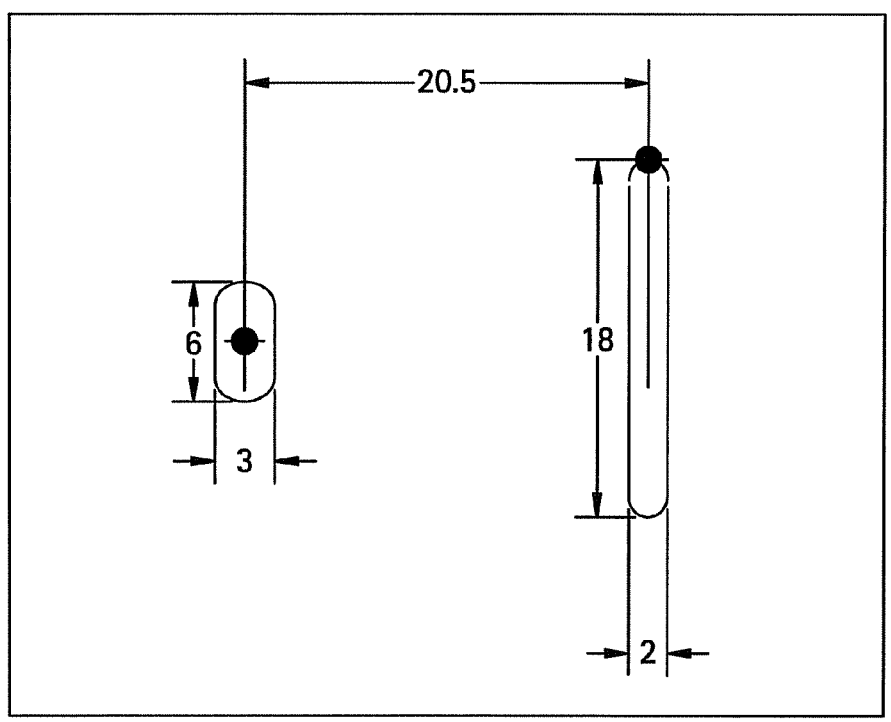
FIG. 6(b) shows the resulting layout after following limitations 3 & 4 (described below) and defining $X_D$, $P_S$ (y-spacing between smaller element and larger element after packing).

$X_D$=x-dimensions from centroid of smaller feature to the center of the tallest point on the larger feature Example Units=microns FIG. 6(a) shows element 1 and element 2. FIG. 6(a) shows that the two elements can have different sizes. In the FIG. 6(a), the element 1 has a shorter length and a greater width than the element 2. FIG. 6(b) shows the resulting layout after following limitations 3 & 4 and defining $X_D$. The FIG. 6(b) depicts that the spacing between elements can be varied.

Variables are then calculated:

$$A=(\frac{1}{2})*(18)=9$$

$$B=(\frac{1}{2})*(6)+(3)+(\frac{1}{2})*(18)=15$$

$$c=18+(2)*(3)+9=33 \quad w=(2\pi)/(2*20.5)=\pi/20.5$$

Sinusoids are then defined.

$$y=33N+9 \sin((\pi/20.5)x) \quad (1)$$

$$y=33N+15+9 \cos((\pi/20.5)x) \quad (2)$$

N=0, 1, 2, 3 ... n

Figure 7A:
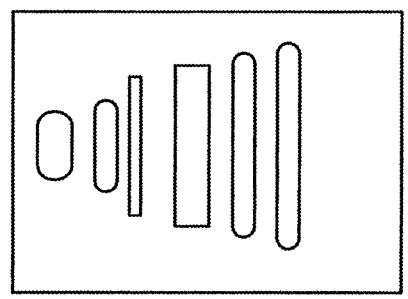
FIG. 7(a) shows a space filled with elements that have a different periodicity.
Figure 7B:
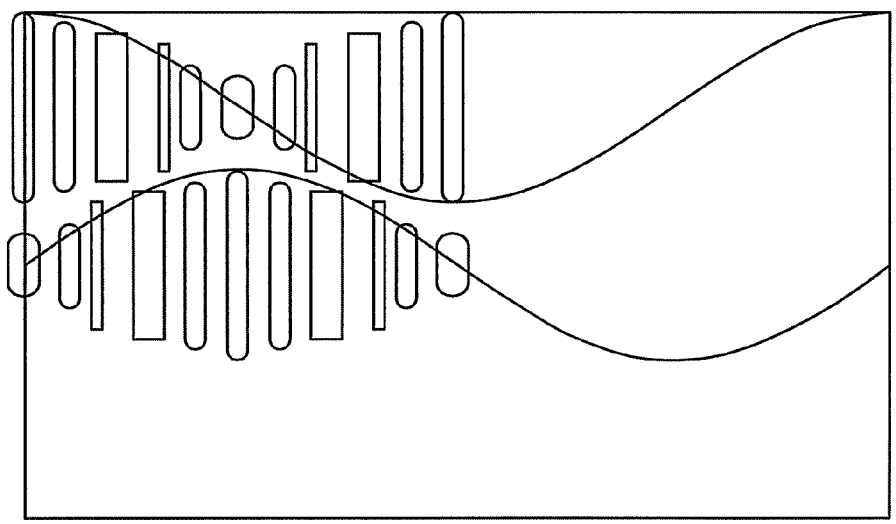
Figure 7C:
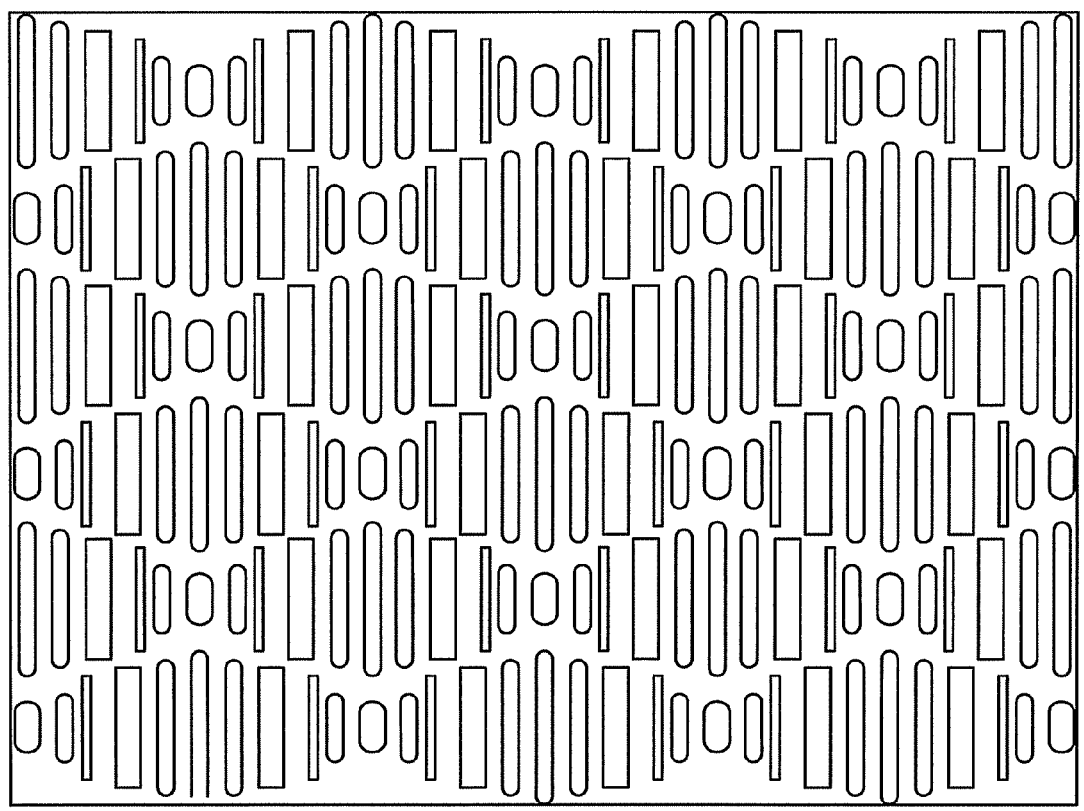
FIG. 7(c) shows the resulting topographical structure over the full area of the desired surface.

The space is then filled with elements between defined elements as shown in FIG. 7(a). Sinusoidal waves are then applied to define periodic repeat definitions as shown in FIG. 7(b) to create the desired topographical structure over the desired surface area shown in FIG. 7(c).

Another method for describing surface topographies according to the invention involves a newly devised engineered roughness index (ERI), first conceived of and used by the present Inventors. The ERI can characterize the roughness of an engineered surface topography. The ERI was developed to provide a more comprehensive quantitative description of engineered surface topography that expands on Wenzel's roughness factor (Wenzel R N. 1936, Resistance to solid surfaces to wetting by water. Ind Eng Chem 28:988-944). It has been found that Wenzel's description alone does not adequately capture the tortuosity of the engineered topographies studied. ERI is expressed as follows in the Equation (3):

$$ERI=(r*df)/f_D \quad (3)$$

wherein the ERI encompasses three variables associated with the size, geometry, and spatial arrangement of the topographical features: Wenzel's roughness factor (r), depressed surface fraction ($f_D$), and degree of freedom for movement ($d_f$).

Wenzel's roughness factor refers to the ratio of the actual surface area to the projected planar surface area. The actual surface area includes areas associated with feature tops, feature walls, and depressed areas between features. The projected planar surface area includes just the feature tops and depressions.

The depressed surface fraction ($f_D$) is the ratio of the recessed surface area between protruded features and the projected planar surface area. This depressed surface fraction term is equivalent to both 1-$\phi_S$ and 1-$f_1$ where $\phi_S$ is the surface solid fraction as described by Quéré and colleagues (Bico J, Thiele U, Quéré D. 2002. Wetting of textured surfaces. Colloids Surf A: Physicochem Eng Aspects 206:41-46; Quéré D. 2002. Rough ideas on wetting. Physica A: Stat Theoret Phys 313:32-46) and $f_1$ is the solid-liquid interface term of the Cassie-Baxter relationship for wetting (Cassie A B D, Baxter S. 1944. Wettability of porous surfaces, Trans Faraday Soc 40:546-551).

Figure 14A:
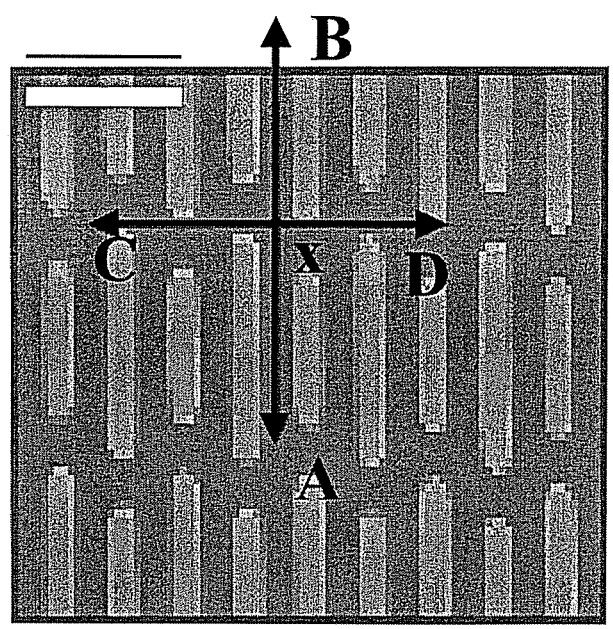
FIG. 14(A) shows a pattern that results in two degrees of freedom for an organism traveling along a channel.
Figure 14B:
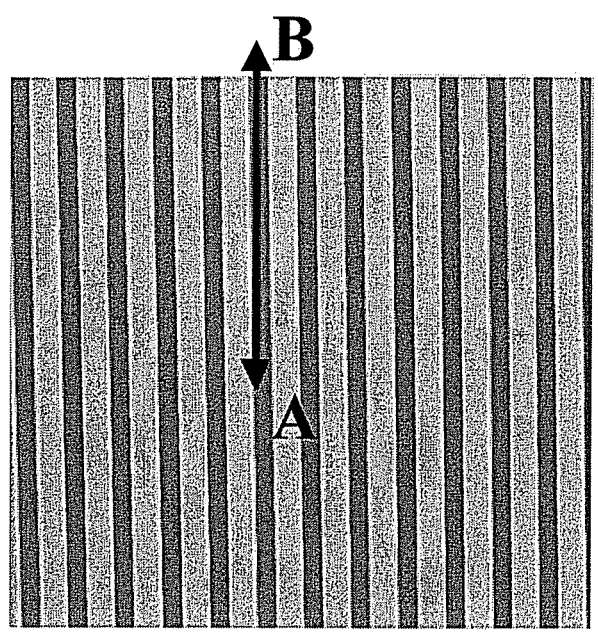
FIG. 14(B) shows a pattern that results in one degree of freedom for an organism traveling along a channel.

The degree of freedom for movement relates to the tortuosity of the surface and refers to the ability of an organism (e.g. Ulva spore or barnacle) to follow recesses (i.e., grooves) between features within the topographical surface. If the recesses form a continuous and intersecting grid, movement in both the x and y coordinates on a plane surface is permitted and the degree of freedom will be 2. Alternatively, if the grooves are individually isolated (e.g. as in channel topographies) then movement is only allowed in one coordinate direction, the degree of freedom will be 1. The calculation of degrees of freedom can be seen in the FIG. 14. FIG. 14A contains a pattern where an organism traveling in a channel between two raised features can, upon arriving at the point X migrate in either the direction A-B or the direction C-D. It therefore has two degrees of freedom available to it. In the FIG. 14B, an organism travelling can only travel in the direction A-B along the channel. The organism therefore has only one degree of freedom.

In addition to being able to control bioadhesion, it is desirable for the surface to function as a non-wetting surface to any fluid. This is accomplished by minimizing the value of $f_D$ in the Equation (3) above. In minimizing the ERI value, the value of $r/f_D$ is increased, thereby increasing the ERI value.

Figure 9:
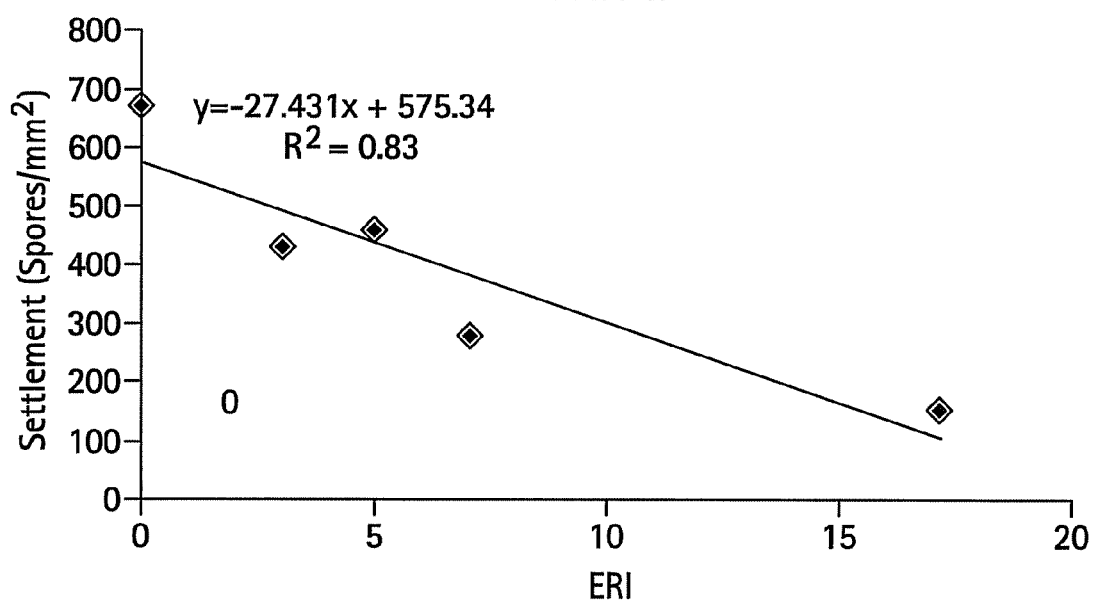
FIG. 9 shows a correlation between *Ulva* Spore settlement density and the corresponding Engineered Roughness Index (ERI) for several topographical patterns according to the invention (shown in A-D above the correlation data).

As such, as shown in FIG. 9 described in detail below, larger ERI values correlate with reduced settlement. It is generally desirable to have ERI values of about 5 to about 40, specifically about 7 to about 30, and more specifically about 9 to about 20. In a preferred embodiment, the ERI is at least 5, preferably 8 or more, preferably 10 or more, preferably 15 or more.

A related surface description according to another embodiment of the invention comprises a polymer layer having a surface. The polymer layer is an elastomer containing a plurality of dissimilar neighboring protruding non-planar surface features where for repelling algae, the features are spaced between 0.5 and 5.0 microns. The features are such that the stress required to bend the feature is 10% greater than the stress required to strain a cell wall and where the features have a greater than 10% bending modulus difference in the bending modulus between two neighboring features, or in the case of three or more neighboring features, their vector equivalence difference of greater than 10%. Preferably, the surface features exist on the surface at a features per area concentration of greater than 0.1 square microns.

The invention provides numerous benefits to a variety of applications since surface properties can be customized for specific applications. The invention can provide reduced energy and cost required to clean surfaces of biofouling by reducing biofouling in the first place. As a result, there can be longer times between maintenance/cleaning of surfaces. As explained below, the invention can also provide non-capsule formation due to foreign body response in the case of coated implanted articles. The invention can also be configured to provide enhanced adhesion to surfaces.

The present invention is thus expected to have broad application for a variety of products. Exemplary products that can benefit from the bioadhesion resistance provided by coating architectures according to the invention include, but are not limited to, the following:

a. biomedical implants, such as breast plant shells or other fluid filled implant shells;
b. biomedical instruments, such as heart valves;
c. Hospital surfaces, e.g., consider film (electrostatic) applications to surfaces that can be readily replaced between surgeries;
d. Clothing/protective personal wear;
e. Biomedical packaging;
f. Clean room surfaces, such as for the semiconductor or biomedical industry;
g. Food industry, including for packaging, food preparation surfaces;
h. Marine industry-including exterior surfaces of marine vessels including ships and associated bilge tanks and gray water tanks and water inlet/outlet pipes;

i. Water treatment plants including pumping stations;
j. Power plants;
k. Airline industry;
l. Furniture industry, such as for children's cribs;
m. Transportation industry, such as for ambulances, buses, public transit, and
n. Swimming pools The articles may find utility in biomedical implants, such as breast plant shells or other fluid filled implant shells; biomedical instruments, such as heart valves; hospital surfaces (e.g., consider film (electrostatic) applications to surfaces that can be readily replaced between surgeries); clothing/protective personal wear; biomedical packaging, such as, for example, the outside surface of sterilized packaging; clean room surfaces, such as, for example, the semiconductor or biomedical industry; food industry, such as, for example, food packaging, food preparation surfaces; marine industry, such as, for example, exterior surfaces of marine vessels including ships and associated bilge tanks, gray water tanks and water inlet/outlet pipes; water treatment plants, such as, for example, pumping stations; power plants; airline industry; furniture industry, such as, for examples, for children's cribs, handles on exercise equipment, and exercise equipment; in the transportation industry, such as, for example, in ambulances, buses, public transit; swimming pools and other structures that are used in aquatic environments; and the like. Additional details of the types of articles and surfaces upon which the pattern can be disposed are provided below.

The pattern may be used in articles that include medical devices, medical implants, medical instruments that are used internal or external to the body of living beings. The term "living beings" can include warm blooded animals, cold blooded animals, trees, plants, mammals, fishes, reptiles, amphibians, crustaceans, and the like. The medical devices, medical implants and medical instruments may be temporarily or permanently inserted into the body of the living being. Examples of medical devices, medical implants and medical instruments are endotracheal tubes; stents; shells used to encapsulate implants such as, for example, breast implant shells; breast implants; ear tubes; heart valves; surfaces of bone implants; surfaces of grafted tissues; surfaces of contact lens; components and surfaces of dialysis management devices such as, for example, a dialysis line; components and surfaces of urinary management devices such as, for example, a urinary catheter; components and surfaces of central venous devices such as, for example, a urinary catheter; surfaces of implanted devices such as, for example, pacemakers, artificial pancreas, and the like; ports on catheters such as, for example, feeding tube ports, implanted venous access ports. It is to be noted that the patterns can be varied to permit bioadhesion or to resist bioadhesion. These variations include geometrical variations, dimensional variations, variations in surface chemistry, or the like. These variations may be static or dynamic variations.

As noted above, the pattern can be disposed on the surfaces of bone implants, such as, for example, an orthopedic implant or other implant in a hip joint replacement or repair, knee replacement or repair, shoulder replacement or repair, elbow replacement or repair, and an ankle replacement or repair. The pattern can also be used as a surface in implantable medical devices where the goal is to cause cells (e.g., progenitor and/or stem cells) to differentiate themselves; the topography of the patterned surface causing this differentiation to occur. As noted above, these medical devices may be implanted permanently or temporarily.

The pattern can be used on outer and inner surfaces of devices, instruments, furniture, and the like used in hospitals, healthcare centers, dental offices, dispensaries, gymnasiums, rehabilitation facilities, bathrooms, waiting rooms, and the like. As listed below, the pattern can be used in hospitals, healthcare centers, dental offices, dispensaries, gymnasiums, rehabilitation facilities, bathrooms, waiting rooms, and the like. The patterns can be used on the surfaces of an electrostatic film applied to operating room surfaces between surgeries; on the surfaces of surgical drapes used to cover patients and/or shield doctors from fluids; on the surfaces of waiting room chairs and waiting room furniture; on the surfaces of operating room instruments; on the surfaces of operating room instrument trays; on high tough surfaces in hospital rooms; on bedside table surfaces; on bedrail switch panel (e.g., control panels) surfaces; on cover surfaces (polymer covers of various thicknesses and dimensions) such as bed sheets and on other surfaces where keeping the surface clean is important. The surfaces of the aforementioned devices, instruments and furniture may be textured, or alternatively a film having a textured surface can be attached to the device, instrument and furniture using permanent or temporary means of attachment such as adhesives, static electricity, mechanical interlocking devices such as nails, screws, nuts, clips, bevel joints, dove tail joints, and the like.

The pattern can also be used to protect the surfaces of all touch screens such as, for example, a computer screen cover—especially a touch screen cover—where keeping the surface clean is desirable. The film used to protect the touch screen can contact the screen or its frame using the permanent or temporary means of attachment discussed above.

The pattern can also be disposed on the inner and outer surfaces of medical packaging such as the surfaces of a sterile package. It can also be disposed for example, on all bed rail coverings in hospitals, medical facilities and nursing stations. The pattern can also be disposed on all bathroom, locker room and waiting room surfaces, especially on all bathroom and waiting room surfaces in hospitals, office buildings, schools, colleges, stadiums, and other places where mass gatherings of people take place and where there is an increased probability of disease transmission.

For example, in bathroom, locker room and waiting room surfaces, it can be disposed on the surfaces of toilets, sinks, hand washing areas, hand drying areas, mirrors, doors, door handles, door locks, push plates located on door surfaces, supporting rails in the bathrooms, surfaces of sources of illumination (e.g., the overhead lighting in a dentists office), and the like. The pattern can also be used as a filter for filtering particles in the nanometer and micrometer ranges. In one embodiment, the pattern can be used for filtering hydrocarbons and polymers.

The pattern can also be disposed on all surfaces of an ambulance. For example, it can be disposed on all work surfaces that are contacted by the health care provider (e.g., emergency medical technicians, doctors, nurses, laboratory technicians) or by the patient. In another embodiment, the pattern can also be disposed on all surface of Class I medical devices such as, for example, thermometer tips, pens and other stationary, doctor/nurse gowns and clothing used by health care providers.

In one embodiment, the pattern can be disposed on the surface of ploughs that are used to collect and shovel snow (e.g., snow ploughs). The snow plough can be rendered self-cleaning. Ice that normally adheres to the snow plough will be easily removed, providing for a clean ploughed surface.

The pattern can also be disposed upon viewing surfaces such as window panes, wind shields, eye glasses, and the like. Since the features of the pattern can be smaller than the wavelength of visible light, the viewing surface will not scatter light. In addition, the presence of the texture will render the surface self cleaning.

In one embodiment, the pattern can be disposed on the surfaces of laboratory culture dishes where the attachment of organisms to any surface inside the dish is not desired (e.g., the pattern causes lesser attachment rate than would otherwise be the case). In another embodiment, the pattern can be disposed on a laboratory culture dish where the attachment of an organism to any surface inside the dish is desired (e.g., the pattern causes greater attachment rate than would otherwise be the case).

In one embodiment, the pattern can be disposed on a surface of devices that can be used to carry or to transport medical equipment or medical components (e.g., a contact lens carrying case, packaging for catheters, packaging for guidewires, packaging for needles, packaging for syringes, and the like).

In another embodiment, the pattern can be disposed on surfaces that are contacted by living beings both inside and outside of hospital or health care facilities. The surfaces can be metallic or non-metallic. For example, it can be disposed on the surfaces of bathroom fixtures such as toilet seats, shower tiles, towel racks, shower curtains, and the like. It can also be disposed on the surfaces of kitchens and dining halls (e.g., kitchens in restaurants, homes, hospitals, and the like) and instruments used in kitchens such as, for example, countertops, sinks, refrigerator surfaces, microwave surfaces, oven surfaces, stove top surfaces, food trays (e.g., those used in airlines, ships and on buses), the surfaces of knives, forks, spoons, ventilators, and the like.

The pattern can also be disposed on instruments and/or surfaces used in an office, gymnasium or laboratory environment such as, for example, work table surfaces (e.g., metallic or non-metallic), chair surfaces, handles of chairs, computer surfaces, keyboards, surfaces of a mouse, surfaces of memory sticks, clean room surfaces, exercise equipment surfaces, surfaces of public buses and trains (e.g., grab rails or other surfaces such as push bars on doors that are contacted by living beings), and the like.

The pattern can also be disposed on surfaces used in the transportation of food-stuffs such as plastics, textiles, textile nets, serrated plastics, and the like. The pattern can also be disposed on food packaging, packaging for fruits and vegetables (e.g., carrots, tomatoes, potatoes, corn, apples, grapes, mangoes, cauliflower, oranges, peaches, tangerines, nectarines, lettuce, cabbage, eggplant, okra, onions, nuts, dates, figs, lemons, lime, grapefruit, walnuts, cashew, pecans, and the like).

The pattern can also be disposed on surfaces used in water filtration used in fresh and saline water treatment facilities. For example, it can be used on the inner and outer surfaces of pipes and hoses used to transfer water or other fluids, filters, nozzles, valves, heaters, granular particles, and the like.

It can also be used in devices that are used to transform fluids from a first state to a second state. For example, it can be used on surfaces of devices that are used to transform liquids to gases, gases to solids, solids to liquids and gases to liquids. It can also be used on the surfaces of devices that contact flowing fluids. It can be used on the surfaces of ice makers, vaporizers, humidifiers, air conditioners, fans, propellers, airfoils (e.g., the leading edge and trailing edges of airplane wings), wind tunnels, exterior body panels of automobiles, ships, airplanes, solar panels, wind turbines, turbine blades, siding (e.g., metallic siding such as aluminum, steel, wooden siding and plastic siding) used on the exterior and interior surfaces of buildings, ducts that transport air inside buildings, and the like. The pattern can be used on packaging for thermal insulation used in the interior of structures (e.g., buildings, airplanes, ships, and the like), construction surfaces (e.g., the surface of wooden beams, metal beams, plastic beams, bricks, dry wall, and the like), and the like, to prevent the buildup of spores and mold when such surfaces contact moisture over extended periods of time.

The pattern can also be used on the internal and external surfaces of electronic devices used for entertainment; communications; signal transmission; capturing images; capturing and transmitting auditory signals; and the like. Examples of entertainment devices are solid-state musical devices (e.g., iPODS®), solid-state gaming devices and electronic toys (e.g., NINTENDO DS®, LEAPSTER®), and the like. Examples of communication devices are cell phones (e.g., Motorola i870, iPhone, and the like), personnel digital assistant (PDA) phones (e.g., Blackberry), laptops, iBooks, and the like. Examples of image capturing devices are optical lenses, digital cameras, infrared cameras, infrared scopes, night vision goggles, and the like. Examples of devices for capturing auditory signals are blue tooth headsets, earphones, and the like.

The pattern can also be disposed on surfaces that contact the mucous membranes of living beings. For example, it can be used on all surfaces that are contacted by the human mouth especially those surfaces that contact the mouths of toddlers. Examples of surfaces that are contacted by the mouths of toddlers are high chair trays, pacifiers, diaper changing pads, crib frames and rails, reusable and disposable water bottles, cups and mugs, coffee thermos, toys, blocks, coins, and the like.

The pattern can also be disposed on the surface of a variety of miscellaneous items such as, for example, clothing and accessories, sunglass lenses, frames of sunglasses, eye glass lenses, surfaces and frames of aquariums, outdoor clothing, water resistant jackets, coats, sports clothing, swimsuits, wetsuits, surfboards, outdoor equipment, tents, lanterns, lamps, tickets (e.g., to sporting events, airline tickets, train and ship tickets), shirt and dress collars, textile surfaces that contact armpits and other private parts of the body, and the like. Such surfaces can be marketed as being antimicrobial surfaces.

The pattern can also be disposed on the surfaces of camping equipment (e.g., tents, poles, lamps, and the like), camping gear, sports equipment (e.g., parachutes, parachute rigs, parachute bags, insides and outsides of shoes, insoles, and the like), and the like. Such equipment can be marketed as water resistant equipment that deters microorganism aggregation. It can also be marketed as deterring the buildup of odor in shoes and underwear.

The pattern can also be disposed on the surfaces of marine vessels and other devices that contact water. For example, it can be used on boat hulls, intake and outlet pipes for industrial and power plants, drilling rig for underwater surfaces, fish tanks and aquariums, boat surfaces (above the hull), bilge tanks, water treatment plants and pumping station surfaces—any surface inside such a water treatment plant and pumping station where organism growth and colonization is an issue. The pattern can be disposed on the surfaces of bags used to grow algae, for example, it can be used on the surface of a bag used to grow any microorganism but prevent attachment of the microorganism onto the surface of bag (medical or marine—e.g., blood bags where it is desirable to deter organism attachment to bag). Alternatively, by varying the surface texture or the size of the texture dimensions, it can be used on the surface of a bag used to grow any microorganism and encourage attachment of the microorganism to surface of the bag (e.g., a stem cell culture where it is desirable to encourage growth and attachment to surface).

The pattern can also be disposed on a variety of other items: bags, handbags, garbage bags, bags that are used for carrying tissue, fluids from living beings, waste and other byproducts from living beings, and the like. Examples of tissue, fluids, waste from living beings are urine, blood, saline, glucose, feces, fluids from the mucous membranes, and the like.

The pattern can also be used on the surfaces of body parts that are used in surgeries such as, for example, in a colostomy, and the like. It can also be used in replacement joints, plates, tendon and ligament ends for enhanced tissue adaptation, vascular implants, grafts, shunts, access, and the like. The pattern may also be used on the inner and outer surfaces of periodontal dressings; intravenous catheters and ports; foley catheters; surfaces in contact with tissues such as, for example, plates; adhesive tapes, patches, bandages, and the like; electronic leads; dental implants; orthodontia devices; iols (intraocular lenses); hydrogel films for tissue enhancement, skin grafting, isolation of bacteria from tissues; heart-lung machine surfaces to reduce infection, clotting/thrombosis, enhance flow; tissue constructs for organ/tissue genesis; dialysis machine components, tubing and control panels; cochlear/otolaryngology implants and electronic devices; pace maker leads and body; fibrillator leads and body; heart valve flow surfaces and fixation surfaces; spinal implants; cranial/facial implants; biomedical instruments such as, for example, heart valves; scalpels; tongs; forceps; saws; reamers; grippers; spreaders; pliers; hammers; drills; laryngoscopes; bronchoscopes; oesophagoscopes; stethoscopes, mirrors, oral/ear speculum, xray plates/frames, x-ray device surfaces, magnetic resonance imaging (MRI) surfaces, echo cardiogram surfaces, cat-scan surfaces, scales, clipboards, and the like.

The pattern can be disposed on hospital surfaces. For example, it can be used as a film to be applied to surfaces that can be readily replaced between surgeries. For example, it can be applied to such surfaces as listed below using electrostatic adhesion, mechanical interlocking or adhesives. The film can be used on table tops, MRI/CAT scan surfaces, X-ray surfaces, scales, operating tables, door push panels, devices or articles that are contacted by human beings such as, for example, light switches, control panels, beds, incubators, monitors, remote controls, call buttons, door push bars, preparation surfaces, instrument trays, pharmacy surfaces, pathology tables, outside surfaces of bed pans, identification surfaces on walls, clothing/protective personal wear, gloves, cling films to attach temporary in public rest rooms/areas, baby changing cling films, films for attaching to bottoms of purses/bags/suitcases, biomedical packaging, such as the outside surface of sterilized packaging; vacuum formed trays/films, cling films for short and long term use, clean room surfaces, such as, for example, those used for the semiconductor or biomedical industry, table tops, push bars, door panels, control panels, instruments, entrance/exit points, food industry, including for packaging, food preparation surfaces, counter tops, cutting boards, trays, entrance/exit points, switches, control panels, scales, packaging equipment operator contact points, marine industry, exterior surfaces of marine vessels including ships, bilge tanks, gray water tanks, water inlet/outlet pipes, power drive systems, propellers, jet ports, water treatment plants including pumping stations, inlet/outlet pipes, control panel surfaces, laboratory surfaces, power plants, inlet/outlet pipes, control surfaces, airline industry, trays on seatbacks, entry/exit push surfaces, bathroom doors, service carts, arm rests, furniture industry, children's cribs, handles on exercise equipment, exercise equipment contact surfaces, changing tables, high chairs, table tops, food prep surfaces, transportation industry, ambulances, buses, public transit, swimming pools.

EXAMPLES

It should be understood that the Examples described below are provided for illustrative purposes only and do not in any way define the scope of the invention.

Figure 8A:
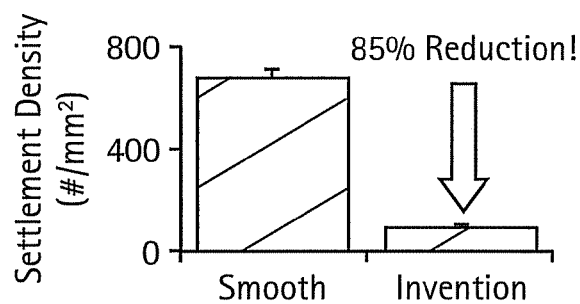
FIG. 8(a) shows settlement density data for algae spores on a smooth control sample as compared to the settlement density on the Sharklet surface architecture according to the invention shown in FIG. 1(a)
Figure 8B:
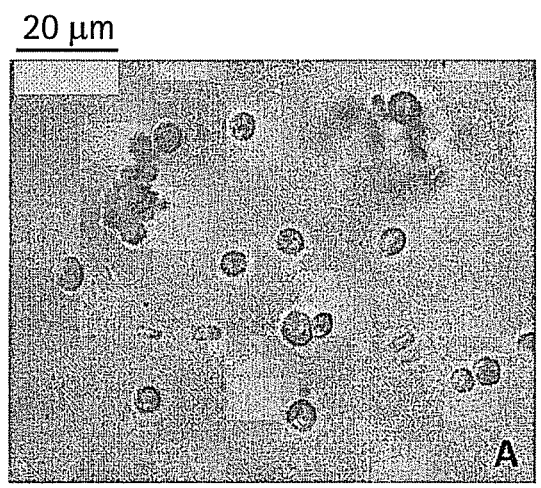
Figure 8C:
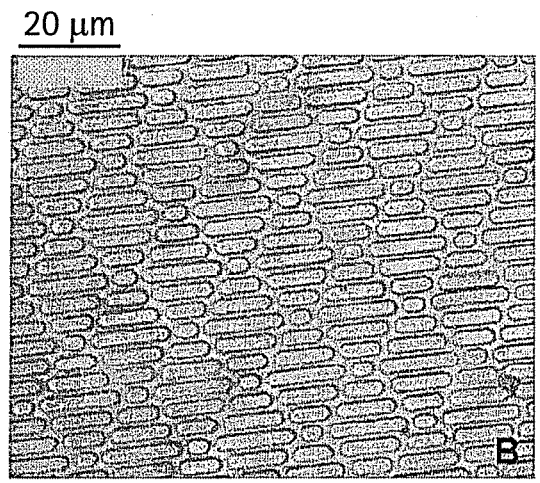
FIG. 8(c) is a scanned light micrograph image showing a dramatic reduction in algae spores on the surface of the surface architecture according to the invention shown in FIG. 1(a).

An experiment was performed to compare the performance of an exemplary surface architecture according to the invention having features formed from a PDMS elastomer as compared to a planar uncoated control surface (the same PDMS elastomer) against bioadhesion of algae spores. The inventive surface topography was the Sharklet shown in FIG. 1(a). Following 45 minutes of exposure, as shown in FIG. 8(a), the settlement density of algae spores on the smooth control sample was about 720/mm$^2$, while the settlement density for the surface architecture according to the invention was only about 100/mm$^2$, or only about 15% of the settlement density of the control. FIG. 8(b) is a scanned light micrograph image of the surface of the control, while FIG. 8(c) is a scanned light micrograph image of the surface of the surface architecture according to the invention.

A further set of *Ulva* spore settlement assays were conducted to evaluate the impact of ERI. All pattern designs tested were transferred to photoresist-coated silicon wafers using previously described photolithographic techniques. Patterned silicon wafers were reactive ion etched, utilizing the Bosch process, to a depth of approximately 3 μm creating a topographical negative. Wafers were then stripped of photoresist and cleaned with an $O_2$ plasma etch. Hexamethyldisilazane was vapor deposited on the processed silicon wafers to methylate the surfaces in order to prevent adhesion.

Topographical surfaces were transferred to PDMSe from replication of the patterned silicon wafers. The resultant topographies contain features projecting from the surface at a height of approximately 3 μm. Pattern fidelity was evaluated with light and scanning electron microscopy.

*Ulva* spore settlement assays were conducted with 76 mm×25 mm glass microscope slides coated with smooth and topographically modified PDMSe surfaces. Glass slides coated with PDMSe topographies were fabricated using a two-step curing process as previously described (Carman et al. 2006). The resultant slide (~1 mm thickness) contained an adhered PDMSe film with a 25 mm×25 mm area containing topography bordered on both sides by 25 mm×25 mm smooth (no topography) areas.

Three replicates of each topographically-modified PDMSe sample, permanently adhered to glass microscope slides, were evaluated for settlement of *Ulva* spores. Topographies included the Sharklet (inset A; upper left), 2 μm diameter circular pillars (inset C; lower left), 2 μm wide ridges (inset D; lower right), and a multi-feature topography containing 10 μm equilateral triangles and 2 μm diameter circular pillars (inset B; upper right). A uniformly smooth PDMSe sample was included in the assay and served as a control for direct comparison.

Regarding the Sharklet, 2 μm ribs of various lengths were combined centered and in parallel at a feature spacing of 2 μm. The features were aligned in the following order as indicated by feature length (μm): 4, 8, 12, 16, 12, 8, and 4. This combination of features formed a diamond and was the repeat unit for the arrayed pattern. The spacing between each diamond unit was 2 μm. Similar to that of the skin of a shark in terms of feature arrangement, this pattern was designed such that no single feature is neighbored by a feature similar to itself.

Regarding the 2 μm diameter circular pillars shown in inset C, patterns of 2 μm pillars and 2 μm ridges were designed at an analogous feature spacing of 2 μm. The pillars were hexagonally packed so that the distance between any two pillars was 2 μm. Regarding the 2 μm wide ridges shown in inset D, the ridges were continuous in length and spaced by 2 μm channels (D).

Regarding the multi-feature pattern shown in inset B, the pattern was designed by combining 10 μm triangles and 2 μm pillars. Pillars were arranged in the same hexagonal packing order as in the uniform structure. At periodic intervals, a 10 μm equilateral triangle replaced a set of six 2 μm pillars forming the outline of a 10 μm triangle. Thus, this design maintained a 2 μm feature spacing between each edge of the triangle and pillars.

Fertile plants of *Ulva linza* were collected from Wembury beach, UK (latitude 50°18'N; 4°02'W). *Ulva* zoospores were released and prepared for attachment experiments as documented previously (Callow et al. 1997).

Topographical samples were pre-soaked in nanopure water for several days prior to the assay in order for the surfaces to fully wet. Samples were transferred to artificial seawater (TROPIC MARIN®) for 1 hour prior to experimentation without exposure to air. Samples were then rapidly transferred to assay dishes to minimize any dewetting of the topographical areas. Ten ml of spore suspension (adjusted to $2\times10^6$ spores per ml) were added to each dish and placed in darkness for 60 minutes. The slides were then rinsed and fixed with 2% glutaraldehyde in artificial seawater as described in Callow et al. (1997).

Spore counts were quantified using a Zeiss epifluorescence microscope attached to a Zeiss Kontron 3000 image analysis system (Callow et al. 2002). Thirty images and counts were obtained from each of three replicates at 1 mm intervals along both the vertical (15) and horizontal (15) axes of the slide.

Spore density was reported as the mean number of settled spores per mm$^2$ from 30 counts on each of three replicate slides ±standard error (n=3). Statistical differences between surfaces were evaluated using a nested analysis of variance (ANOVA) followed the SNK (Student-Newman-Kuels) test for multiple comparisons. Replicate slides (3) of each surface (5) were treated as a nested variable within each surface.

The mean spore density measured for each of the studied PDMSe surfaces was plotted against the calculated engineered roughness index (ERI) to determine if any correlations existed. It must be noted that these ERI values are for a fixed feature spacing of 2 μm and depth of 3 μm.

Spores were calculated to settle at a mean density of 671±66 spores/mm$^2$ on the smooth PDMSe surface. All topographies showed a statistically significant reduction in spore density relative to this smooth surface as evaluated by ANOVA analysis followed by the SNK multiple comparison test. A lower mean spore density was measured on the triangles/pillars (279±66) compared to both the pillars (430±81) and ridges (460±54). The Sharklet topography had the lowest spore density (152±32) compared to all other surfaces.

For the 2 μm wide ridges, the majority of the settled spores were bridged between the top edges of neighboring ridges. A few smaller spores were found squeezed within the 2 μm wide channels between ridges.

Spores remained atop the hexagonal packed 2 μm diameter pillars. No settled spores were observed on flat areas between pillars. For the multi-feature topography containing both 10 μm triangles and 2 μm pillars, spores completely avoided settling on the flat top surface of the triangle. Most spores appeared to have settled on top of a pillar while leaning against the edge of the triangle feature. The table below provides the calculated ERI values for the studied topographical patterns.

TABLE

| | Feature Geometry | | | Engineered Roughness Index | | | |
|---|---|---|---|---|---|---|---|
| | depth | spacing (μm) | width | r | df | $f_D$ | ERI (r*df)/$f_D$ |
| Ridges | 3 | 2 | 2 | 2.5 | 1 | 0.50 | 5 |
| Pillars | 3 | 2 | 2 | 2.36 | 2 | 0.77 | 6.1 |
| Triangles/Pillars | 3 | 2 | 2, 10 | 2.23 | 2 | 0.51 | 8.7 |
| Sharklet | 3 | 2 | 2 | 2.5 | 2 | 0.53 | 9.5 |
| Smooth | n/a | n/a | n/a | 1 | 2 | 1 | 2 |

Calculated engineered roughness index (ERI) values for the studied topographical surfaces.

The mean spore density measured on each tested PDMSe surface was plotted against the calculated engineered roughness index (ERI) as shown in FIG. 9. A correlation was observed and a linear regression model was fit to the data. A fairly strong (R2=0.69, p<0.001) inverse linear relationship existed between mean spore density and ERI by the following equation:

$$\text{Spore Density(spores/mm}^2) = 796 - 63.5 * (\text{ERI}) \quad (2)$$

The Sharklet had highest ERI (9.5) and lowest mean spore density. Following the trend, the triangles/pillars topography had the second highest ERI (8.7) and the second lowest mean spore density. Both the uniform ridges and pillars topographies had lower ERI values (5.0 and 6.1 respectively) and higher mean spore densities than both the Sharklet and triangles/pillars. There were no statistical differences in the mean spore densities of uniform ridges and pillars topographies.

Since feature width and spacing were the same for all these topographies, differences in ERI values were associated only with differences in feature geometry and tortuosity. This indicated that the geometric shape and arrangement of the individual features of Sharklet was likely critical because it enhanced anti-settlement effectiveness over topographies of equivalent dimensions.

Not all topographically modified or roughened surfaces have anti-settlement properties for *Ulva* spores. Spore settlement results on topographies presented here and previously have indicated that a critical interaction must be achieved between individual topographical features and the spore for the entire surface to be an effective inhibitory surface. Although trends with ERI values and spore settlement have been ascertained, it was only after topographic surfaces were designed at a feature spacing of 2 μm. This indicated that there exists an interaction between roughness measures and feature spacing that must be considered when designing topographic surfaces.

Figure 10:
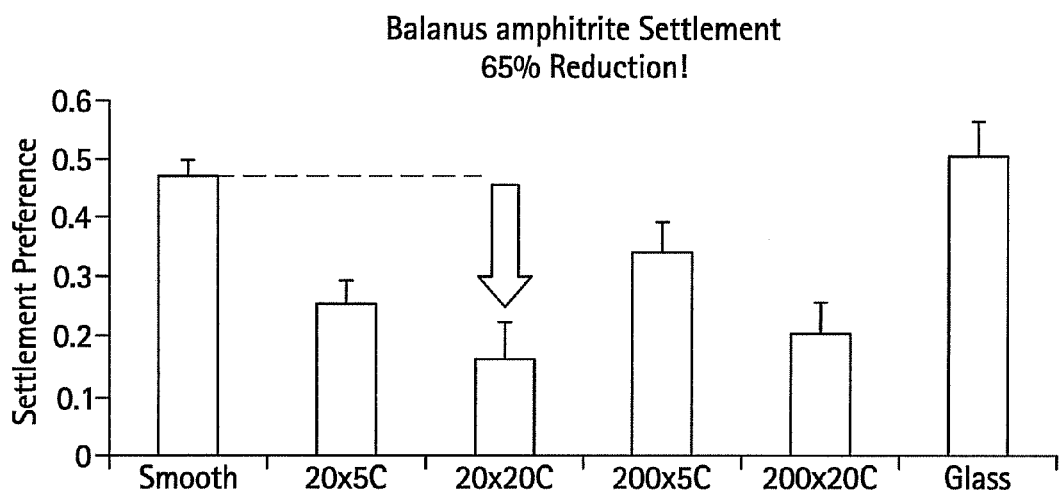
FIG. 10 shows settlement data from *B. amphitrite* on various (PDMS elastomer (PDMSe) channel topographies. Mean values±1 standard error are shown.

In another round of testing, sharklet surfaces according to the invention were prepared and tested for efficacy against barnacle adhesion. In the study, a surface comprising 20 μm×5 μm, 20 μm×20 μm, 200 μm×5 μm and 200 μm×20 μm PDMSe channels were evaluated for *B. amphitrite* (barnacle) settlement and release. The convention used herein is W×D, where W represents both the width and spacing between features and D represents the depth (height) of features. Although equal in this particular example, the invention is in no way limited to the width equaling the spacing. Incubation time was approximately 48 hours. All four topographies reduced settlement relative to a surface of smooth PDMSe. The most significant reduction in barnacle settlement of about 65% was provided by the 20×20 channels as shown in FIG. 10.

Based on the results of this study, surfaces were designed to probe the antifouling properties of topographical features with ~20 μm dimensions. Four replicates each of the following PDMSe topographies were prepared: smooth, 20×20 Channels (20CH), 20×40 Channels (40CH), 20×20 Sharklet (20SK) and 20×40 Sharklet (40SK). Four 0.5 cm³ drops of artificial sea water (ASW) were deposited on each sample and then 10 cyprids dispersed in ~0.5 cm³ ASW were added to each drop, bringing the total volume per drop to 1 cm³. Samples were next placed in a humidified incubator at 28° C. for 24 hrs. Samples were inspected and settlement numbers (cyprids attached+cyprids metamorphosed) were counted. Samples were then returned to the incubator and read after subsequent 24 hr periods following the same protocol. The results collected at 24 and 48 hrs from the initial assay are referred to in the following sections as "assay 1".

Figure 11A:
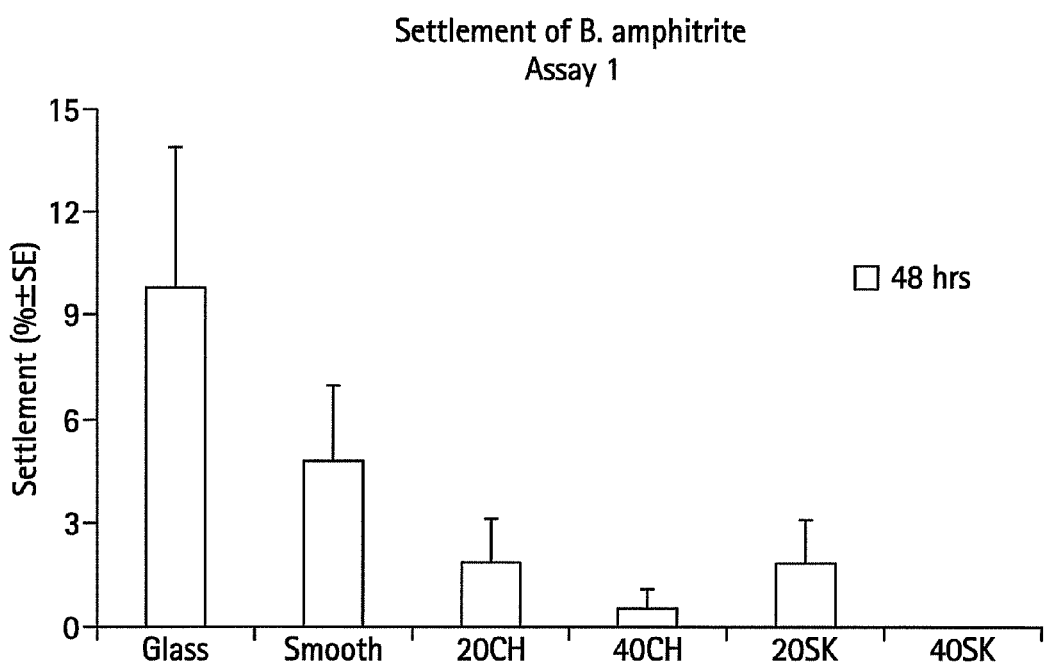
FIG. 11(*a*) is a chart showing barnacle cyprid settlement for a first assay (assay 1). Cyprids were allowed to settle for 48 hrs on each of the test surfaces. Topographies used included 20×20 channels (20CH), 20×20 Sharklet (20SK), 20×40 channels (40CH) and 20×40 Sharklet (40SK). Error bars represent ±1 standard error.

In assay 1, settlement on all surfaces was negligible after 24 hrs, but the 48 hr results shown in FIG. 11(a) appear to indicate that all of the studied topographies reduce barnacle cyprid settlement. The 40SK topography completely inhibited barnacle settlement. However, because the overall settlement counts were quite low (~10% on glass), accurate statistical interpretation of the data was not possible.

Figure 11B:
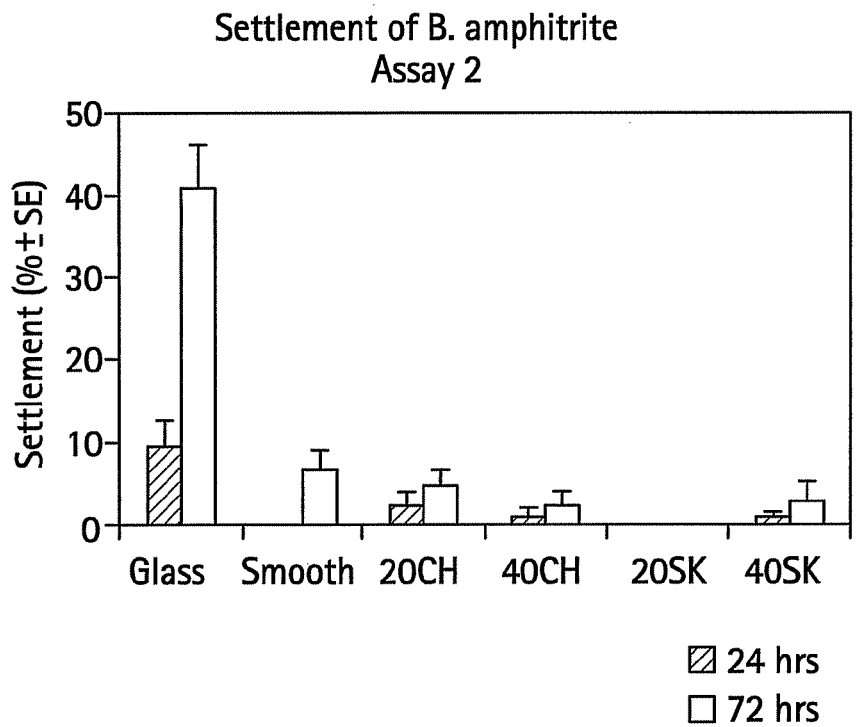

Due to low overall cyprid settlement in assay 1, the decision was made to "clean" the test surfaces and repeat the process. Briefly, surfaces were rinsed in an excess of nanopure water, gently agitated in 90% ethanol on an orbital shaker over night, and subsequently rinsed in nanopure water and allowed to dry in air. On all PDMSe surfaces there was still a vague droplet outline evident following this procedure. Closer inspection suggested that this deposit may be bacterial biofilm. Assay 2 droplets were deposited on areas of the samples not previously used for assay. The results of this second round of testing will be referred to as "assay 2" in which readings were taken after 24 and 72 hrs. Cyprids were allowed to explore for longer in assay 2 to increase settlement, but the 48 hr reading was removed to prevent the potential loss of test droplets during transfer to and from the incubator. After the 24 hr reading, salinity in most of the test droplets had increased through evaporation from ~33 ppt to ~40 ppt so reverse osmosis (RO) water was added to each droplet to return the salinity back to ~33 ppt. For assay 2, significant results were found between glass and all PDMSe surfaces as shown in FIG. 11(b) shows barnacle settlement after both 24 and 72 hrs. The 20SK topography completely inhibited barnacle settlement. However, there were still no significant differences detected between the smooth PDMSe control and the textured inventive surfaces. A repeat experiment with a fresh cyprid batch and new test surfaces was sought so that a definitive conclusion could be reached.

Figure 11C:
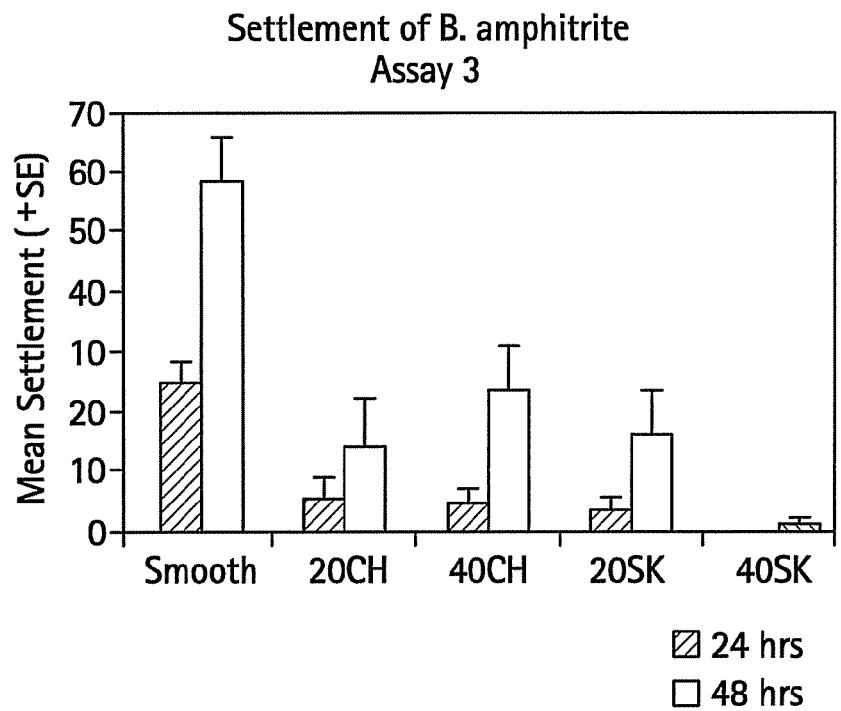

After the completion of assay 2, fresh samples were used to replicate the study. Using the same protocol as before, settlement was evaluated at 24 and 48 hrs for this study (assay 3). All topographies yielded significantly lower settlement compared to smooth after 24 hrs as shown in FIG. 11(c). After 48 hrs, the 20CH and 40SK topographies both showed a significant inhibitory affect on settlement. The 40SK topography almost completely inhibited settlement of the cyprids, which is consistent with assay 1 results. No significant differences were detected between the various topographies according to the invention.

Additional tests were performed to evaluate critical surface dimensions for bacteria. Recent literature on the relationship between zoospores and bacteria cells suggest that zoospores of eukaryote alga can sense a chemical signal produced by bacteria by utilizing a bacterial sensory system. As such, bacterial biofilms have a direct influence on the development of algal communities. Work by the present Inventors with barnacle cyprids as discussed above has also shown the presence of something resembling a bacterial biofilm that was found to remain after washing. These findings suggest that disrupting the bacterial colonization of surfaces can in turn disrupt the settlement of larger organisms such as zoospores or cyprids.

In the investigation with the bacteria *Staphylococcus aureus*, Sharklet topography with 2 μm spacing dimensions was chosen to accommodate isolated, individual bacterium (cell size ~1-2 μm) to prohibit connectivity between bacteria cells thus prohibiting the formation of a confluent biofilm. Samples of 2 μm Sharklet PDMSe, smooth PDMSe, and glass were statically exposed to $10^7$ CFU/mL in growth medium for up to 12 days to promote biofilm formation. Samples were removed on the 2nd, 4th, 7th, and 12th days, gently rinsed by immersion in de-ionized water, and air-dried for characterization.

After 12 days, scanning electron micrographs (SEM) revealed abundant biofilm on glass and slightly less on the smooth PDMSe, but no evidence of biofilm on the Sharklet surface. The SEM images acquired also suggest inhibition of bacterial cell settlement on the Sharklet surface.

It is to be understood that while the invention has been described in conjunction with the preferred specific embodiments thereof, that the foregoing description as well as the examples, which follow are intended to illustrate and not limit the scope of the invention. Other aspects, advantages and modifications within the scope of the invention will be apparent to those skilled in the art to which the invention pertains.

The invention claimed is:

1. An article having a surface topography for resisting bioadhesions of organisms comprising:
    a base surface;
    a plurality of spaced features; wherein each feature has a surface that is substantially parallel to a surface of a neighboring feature, and wherein each feature has a substantially different geometry than neighboring features; the plurality of spaced features arranged in a plurality of groupings, wherein each grouping has at least three features having a substantially different geometry from each other; the spaced features within each of the groupings being spaced apart at an average distance of about 0.5 micrometers to about 200 micrometers; the adjacent groupings of features being spaced from each other to define an intermediate sinusoidal pathway, wherein neighboring sinusoidal paths converge toward and diverge from each other in a substantially mirror symmetry, further wherein a width of each sinusoidal path as measured between two adjacent groupings is substantially uniform.

2. The article of claim 1, wherein the plurality of spaced feature extend outwardly from a surface.

3. The article of claim 2, wherein the plurality of spaced features has a similar chemical composition to the surface.

4. The article of claim 2, wherein the plurality of spaced features has a different chemical composition from that of the surface.

5. The article of claim 2, wherein the plurality of spaced features is applied to the surface in the form of a coating.

6. The article of claim 1, wherein the plurality of spaced features comprises an organic polymer, a ceramic or a metal.

7. The article of claim 6, wherein the organic polymer is selected from the group consisting of a polyacetal, a polyolefin, a polyacrylic, a polycarbonate, a polystyrene, a polyester, a polyamide, a polyamideimide, a polyarylate, a polyarylsulfone, a polyethersulfone, a polyphenylene sulfide, a polyvinyl chloride, a polysulfone, a polyimide, a polyetherimide, a polytetrafluoroethylene, a polyetherketone, a polyether etherketone, a polyether ketone ketone, a polybenzoxazole, a polyphthalide, a polyacetal, a polyanhydride, a polyvinyl ether, a polyvinyl thioether, a polyvinyl alcohol, a polyvinyl ketone, a polyvinyl halide, a polyvinyl nitrile, a polyvinyl ester, a polysulfonate, a polysulfide, a polythioester, a polysulfone, a polysulfonamide, a polyurea, a polyphosphazene, a polysilazane, a polyurethane, an ethylene propylene diene rubber, a polytetrafluoroethylene, a perfluoroelastomer, a fluorinated ethylene propylene, a perfluoroalkoxyethylene, a polychlorotrifluoroethylene, a polyvinylidene fluoride, a polysiloxane, or a combination comprising at least one of the foregoing organic polymers.

8. The article of claim 1, wherein the groupings of features are arranged with respect to one another so as to define a linear pathway or a plurality of channels.

9. The article of claim 1, wherein one or more features are shared between groupings.

10. The article of claim 1, wherein the groupings have patterns of features.

11. The article of claim 1, wherein the features have similar geometries.

12. The article of claim 1, wherein the features have different geometries.

13. The article of claim 1, wherein the features have different dimensions.

14. The article of claim 1, wherein the features are periodic.

15. The article of claim 1, wherein the features are aperiodic.

16. The article of claim 1, wherein the features have a depth to width ratio of about 1 to about 10.

17. The article of claim 1, wherein the features have an average surface roughness of about 5 to about 30.

18. The article of claim 1, wherein the spaced features comprise an inorganic material, and wherein the inorganic material is selected from the group consisting of an inorganic oxide, an inorganic carbides, an inorganic nitride, an inorganic hydroxide, an inorganic oxide having a hydroxide coating, an inorganic carbonitride, an inorganic oxynitride, an inorganic boride, an inorganic borocarbide, or a combination comprising at least one of the foregoing inorganic materials or wherein the inorganic material is a metal oxide, a metal carbide, a metal nitride, a metal hydroxide, a metal oxide having a hydroxide coating, a metal carbonitride, a metal oxynitride, a metal boride, a metal borocarbide, or a combination comprising at least one of the foregoing inorganic materials.

19. The article of claim 1, wherein the spaced features comprise a metal, the metal being selected from the group consisting of iron, copper, aluminum, tin, gold, titanium, silver, tungsten, platinum, palladium, chromium, or a combination comprising at least one of the foregoing metals.

20. The article of claim 1, wherein the article has an engineered roughness index of equal to about 5.

21. The article of claim 1, where the article has an engineered roughness index of equal to about 10.

22. The article of claim 1, where the article has a drug coating disposed thereon.

23. The article of claim 22, where the drug coating is a time release coating.

24. The article of claim 22, where the article is a biomedical implant, a breast implant shell, a fluid filled implant shell; a biomedical instrument; a biomedical device; a heart valve; a hospital surface; clothing/protective personal wear; biomedical packaging; an outside surface of sterilized packaging; a clean room surface; a surface of a semiconductor; food packaging; a food preparation surface; an exterior surface of a marine vessel; an interior surface of a marine vessel; an exterior surface of a ship; a bilge tank; an inlet or an outlet to a water pipe; an inner surface of a pipe or hose; a surface in a water treatment plant; a part of a pumping station; a surface of a power plant; a surface of a child's crib, a surface on handles of exercise equipment; a surface on an ambulance, a surface on a bus, a surface on a public transit vehicle; or a part of a swimming pool.

25. The article of claim 1, where the article comprises a bio-degradable polymer.

26. The article of claim 1, where the article is affixed to a surface by an adhesive, by electrostatic forces, by mechanical interlocking devices, or a combination comprising at least one of an adhesive, electrostatic forces or mechanical interlocking devices.

27. The article of claim 1, where the article is used as an outer and/or an inner surface of a device; an outer and/or an inner surface of an instrument; an outer and/or an inner surface of furniture; a surface on and/or in a hospital; a surface on and/or in a healthcare center; a surface on and/or in a dental office; a surface on and/or in a dispensary; a surface on and/or in a gymnasium; a surface on and/or in a rehabilitation facility; a surface on and/or in a bathroom; a surface on and/or in a waiting room; on a surface of an electrostatic film applied to operating room surfaces between surgeries; on a surface of surgical drapes used to cover patients and/or shield a doctor from fluids; on a surface of waiting room chairs and waiting room furniture; on a surfaces of operating room instruments; on a surface of operating room instrument trays; on a high tough surface in hospital rooms; on bedside table surfaces; on a bedrail switch panel surfaces; on a surface of control panels; on cover surfaces; on a bed sheet surface; on bathroom, locker room and/or waiting room surfaces; on outer and/or inner surfaces of an electronic device; on surfaces of toilets, sinks, hand washing areas, hand drying areas, mirrors, doors, door handles, door locks, push plates located on door surfaces; supporting rails in the bathrooms; surfaces of bathroom fixtures; surfaces of shower tiles; surfaces of towel racks; surfaces of shower curtains; surfaces of sources of illumination; a work surface on all surfaces that are contacted by a health care provider and/or a patient; on all surface of Class I medical devices, thermometer tips, pens, stationary, doctor and/or nurse gowns, and/or clothing used by health care providers; on a surface of laboratory culture dishes where attachment of organisms to a surface inside the dish is not desired; on the surfaces of kitchens and dining halls; surfaces of countertops; surfaces of sinks; refrigerator surfaces; microwave surfaces; oven surfaces; stove top surfaces; surfaces of food trays used in airlines, ships and on buses; surfaces of knives; surfaces of forks; surfaces of spoons; surfaces of ventilators; surfaces of an office; surfaces of a gymnasium; surfaces of a laboratory; work table surfaces; chair surfaces; handles of chairs; computer surfaces; keyboard surfaces; surfaces of a mouse; surfaces of memory sticks; clean room surfaces; exercise equipment surfaces; surfaces of public buses and trains; grab rail surfaces; push bar surfaces; hand rail surfaces; on a surface of a device used for the transportation of food; an inner and/or outer surface of a device that is used to transfer fluids, water, saline water or granular particles; as packaging for thermal insulation used in the interior of structures, buildings, airplanes and ships; as a construction surface; on surfaces to prevent the buildup of spores and mold on surfaces that contact water or moisture over extended periods of time; on internal and external surfaces of electronic devices used for entertainment; communications; on surfaces of signal transmission devices; on surfaces of devices for capturing images; on surfaces for capturing and transmitting auditory signals; on internal and external surfaces of electronic devices; the electronic devices being solid-state musical devices, solid-state gaming devices and electronic toys, cell phones, personnel digital assistant phones, laptops, digital cameras, infrared cameras, infrared scopes, night vision goggles, an optical lens, blue tooth headsets or earphones; as a surface of a filter, nozzle, valve, heater, aspirator, decanter, jar, cup, vaporizer, humidifier, air conditioner, fan, propeller, wind tunnel, exterior body panel of automobile, ship, airplane, solar panel, wind turbine, turbine blade, sidings for buildings, airfoil or siphons; on of surfaces that are contacted by the mouths of babies or toddlers; the surfaces being high chair trays, pacifiers, diaper changing pads, crib frames and rails, reusable and disposable water bottles, cups and mugs, coffee thermos, toys, blocks, coins or nipples; as surfaces on clothing and accessories, sunglass lenses, frames of sunglasses, eye glass lenses, surfaces and frames of aquariums, outdoor clothing, water resistant jackets, coats, sports clothing, swimsuits, wetsuits, surfboards, outdoor equipment, tents, lanterns, lamps, tickets, shirt and dress collars, or textile surfaces that contact armpits and other private parts of the body; as surfaces of camping equipment, tents, poles, lamps, camping gear, sports equipment, parachutes, parachute rigs, parachute bags, insides and outsides of shoes or insoles; on surfaces of marine vessels; on surfaces of boat hulls; on intake and outlet pipes for industrial and power plants; on drilling rigs for underwater surfaces; on fish tanks and aquariums; on boat surfaces above the hull; on surfaces of bilge tanks; water treatment plants or pumping station surfaces; on surfaces of bags that are used to grow algae; on the surfaces of bags that are used to deter the growth of algae; on surfaces of a bag, a handbag, a garbage bag, or a bag that is used for carrying tissue, fluids from living beings, waste and other byproducts from living beings.

28. The article of claim 1, where the article is used in replacement joints; plates; tendon and ligament ends for enhanced tissue adaptation; vascular implants; grafts; shunts; inner and outer surfaces of periodontal dressings; intravenous catheters; ports for intravenous catheters; foley catheters; plates; adhesive tapes; patches; bandages; electrical leads; dental implants; orthodontia devices; intraocular lens; hydrogel films for tissue enhancement; skin grafting; isolation of bacteria from tissues; heart-lung machine surfaces to reduce infection; clotting/thrombosis; tissue constructs for organ/tissue genesis; dialysis machine components; tubing and control panels; cochlear/otolaryngology implants and electronic devices; pace maker leads and body; fibrillator leads and body; heart valve flow surfaces and fixation surfaces; spinal implants; cranial/facial implants; biomedical instruments; heart valves; scalpels; tongs; forceps; saws; reamers; grippers; spreaders; pliers; hammers; drills; laryngoscopes; bronchoscopes; oesophagoscopes; stethoscopes; mirrors; oral/ear speculum; xray plates/frames; xray device surfaces; magnetic resonance imaging surfaces; echo cardiogram surfaces; catscan surfaces; scales; or on clipboards.

29. The article of claim 1, wherein a sum of a number of features in a grouping is equal to an odd number.

30. The article of claim 1, wherein a sum of a number of features in a grouping is equal to an even number.

31. The article of claim 1, wherein a sum of a number of features shared by two neighboring groupings is equal to an odd number.

32. The article of claim 1, wherein a sum of a number of features shared by two neighboring groupings is equal to an even number.

33. The article of claim 1, wherein the sinusoidal pathway is defined by a periodic function.

34. The article of claim 1, wherein the article comprises an organic polymer.

35. The article of claim 1, wherein the article comprises an inorganic material.

36. The article of claim 1, where the article comprises a drug coating.

37. The article of claim 1, where the surfaces that are substantially parallel to the surfaces of neighboring features are both vertical surfaces.

38. The article of claim 1, wherein the article is selected from the group consisting of a thermoplastic polymer, a blend of thermoplastic polymers, a thermosetting polymer, a blend of thermoplastic polymers with thermosetting polymers, a copolymer, a terpolymer, an oligomer, a homopolymer, a block copolymer, an alternating block copolymer, a random copolymer, a random block copolymer, a graft copolymer, a star block copolymer, a dendrimer, a polyelectrolyte, a polyampholyte, an ionomer, or a combination thereof.

39. The article of claim 1, further comprising a second plurality of spaced features; the second plurality of spaced features being disposed upon the first plurality of spaced features; the spaced features of the second plurality of spaced features being arranged in a plurality of groupings; the groupings of features of the second plurality of spaced features comprising repeat units; the spaced features within a grouping being spaced apart at an average distance of about 1 nanometer to about 50 micrometers; the groupings of features being arranged with respect to one another so as to define a sinusoidal pathway; the second plurality of spaced features providing the article with an engineered roughness index of about 5 to about 30.

40. The article of claim 1, where the article comprises an algaecide.

41. The article of claim 40, where the algaecide is selected from the group consisting of 2,2-dibromo-3-nitrilopropionamide (DNP), methylene bis-thiocyanate, 5-chloro-2-methyl-4-isothiazolin-3-one/2-methyl-4-isothiazol in-3-one, tetrahydro-3,5-dimethyl-2H,1,3,5-thiadiazine-2-thione,
sodium dimethyldithiocarbamate/sodium ethylene bis dithiocarbamate, alkyl dimethylbenzyl amonium chloride family, poly[oxyethylene (dimethyliminio)ethylene (dimethyliminio)ethylene dichloride, copper sulfate, or a combination comprising at least one of the foregoing algaecides.

42. The article of claim 1, wherein the plurality of spaced features have a first spacing and have disposed thereon a second plurality of spaced features having a second spacing.

43. The article of claim 1, where the article controls the flow of a fluid that contacts it.

44. The article of claim 1, where the article comprises biologically active agents.

45. The article of claim 44, where the biologically active agents are selected from the group consisting of anti-proliferative/antimitotic agents, vinca alkaloids, vinblastine, vincristine, vinorelbine, paclitaxel, epidipodophyllotoxins, etoposide, teniposide, antibiotics, doxycycline, dactinomycin, actinomycin D, daunorubicin, doxorubicin and idarubicin, anthracyclines, mitoxantrone, bleomycins, plicamycin, mithramycin, mitomycin, enzymes, L-asparaginase, antiplatelet agents, G(GP) IIb/IIIa inhibitors, vitronectin receptor antagonists, anti-proliferative/antimitotic alkylating agents, nitrogen mustards, mechlorethamine, cyclophosphamide and analogs, melphalan, chlorambucil, ethylenimines, methylmelamines, hexamethylmelamine, thiotepa, alkyl sulfonates-busulfan, nitrosoureas, carmustine and analogs, streptozocin, trazenes-dacarbazinine, anti-proliferative/antimitotic antimetabolites, folic acid analogs, methotrexate, pyrimidine analogs, fluorouracil, floxuridine, cytarabine, purine analogs, mercaptopurine, thioguanine, pentostatin, 2-chlorodeoxyadenosine, platinum coordination complexes, cisplatin, carboplatin, procarbazine, hydroxyurea, mitotane, aminoglutethimide, hormones, estrogen, anti-coagulants, heparin, synthetic heparin salts, inhibitors of thrombin, fibrinolytic agents, tissue plasminogen activator, streptokinase, urokinase, aspirin, dipyridamole, ticlopidine, clopidogrel, abciximab, antimigratory agents, antisecretory agents, breveldin, anti-inflammatory agents, adrenocortical steroids, cortisol, cortisone, fludrocortisone, prednisone, prednisolone, 6α-methylprednisolone, triamcinolone, betamethasone, dexamethasone, non-steroidal agents, salicylic acid derivatives, aspirin, para-aminophenol derivatives, acetominophen, indole, indene acetic acids, indomethacin, sulindac, etodalac, heteroaryl acetic acids, tolmetin, diclofenac, ketorolac, arylpropionic acids, ibuprofen and derivatives, anthranilic acids, mefenamic acid, meclofenamic acid, enolic acids, piroxicam, tenoxicam, phenylbutazone, oxyphenthatrazone, nabumetone, gold compounds, auranofin, aurothioglucose, gold sodium thiomalate, immunosuppressives, cyclosporine, tacrolimus, sirolimus, rapamycin, azathioprine, mycophenolate mofetil, angiogenic agents, vascular endothelial growth factor, fibroblast growth factor, angiotensin receptor blockers, nitric oxide donors, anti-sense oligionucleotides, cell cycle inhibitors, mTOR inhibitors, growth factor receptor signal transduction kinase inhibitors, retenoids, cyclin/CDK inhibitors, statins, protease inhibitors, or a combination comprising at least one of the foregoing biologically active agents.

46. The article of claim 44, where the biologically active agents comprise a cancer inhibitors.

47. The article of claim 46, where the cancer inhibitors are selected from the group consisting of (−)-Ci-Cdp1, (−)-Ci-Cdp2, (−)-epigallocatechin gallate, (+)-Cbi-Cdpi2, (+)-Ci-Cdp2, 10-Deacetylbaccatin Iii, 4-demethoxy daunorubicin, 5-azacytidine/5-aza-2'-deoxycytidine, 5-fluorouracil, 5-iminodoxorubicin hydrochloride, 6-mercaptopurine, aclarubicin, acodazole, actinomycin D, adenine phosphate, adenosine, aderbasib, adozelesin; U-73,975, afeletecan, alemtuzumab, alitreninoin, alosetron HCl, alphitolic acid, altretamine, alvespimycin, ambazone, ametantrone, amifostine, aminoglutethimide, amsacrine HCl, amsilarotene, amygdalin, anagrelide, anastrozole, anaxirone, ancitabine, annomontacin, annomuricin A, (C19/C20-Erythro), annomuricin B, (C10/C11,C19/C20-erythro), annomuricin C, annomuricin E, annonacin, annonacin-10-One, annonacin-A-One, annonidin B, annonin VI, annosquamosin A, annosquamosin B, antramycin, apaziquone, argimesna, aristoforin, arsenic trioxide, artemisinin, ascomycin, asparaginase, atosiban, atrimustine, axitinib, azasetron HCl, azatepa, azathioprine, azotomycin, bafetinib, balamapimod, banoxantrone, batabulin, batimastat, Bbr-34384, becatecarin, belotecan, benaxibine, bendamustine, benzodepa, berubicin, betulin, betulinic acid, betulinic aldehyde, bevacizumab, bexarotene, bicalutamide, bietaserpine, biricodar, bisantrene, bistramid A; bistratene A, bizelesin, bleomycin, bleomycin A2, bleomycin A5, bleomycin Sulfate, bortezomib, bosentan, bosutinib, brequinar sodium, brequinar, bropirimine, brostallicin, budotitane, bullatacin, buserelin, busulfan, cabazitaxel, calcium folinate, calcium levofolinate, calusterone, camptothecin, canertinib, canfosfamide, cantharidin, capecitabine, caracemide, carbetimer, carboplatin, carboprost (carboprost tromethamine), carboquone, carfilzomib, carglumic acid, carmofur, carmustine, carzelesin, cedefingol, cemadotin, cetuximab, cevipabulin, chlorambucil, chlormethine (mechlorethamine), chlorotamoxifen, chlorotrianisene, ciot-eronel, cisplatin, cladribine, clanfenur, clofarabine, clofazimine, clomifene citrate, cordycepin, corosolic acid, crisnatol, curcumin, cyclocytidine, cyclophosphamide, cytarabine, cytidine, D-aminolevulinic acid, dacarbazine, damsin, daniquidone, danusertib, daporinad, darinaparsin, dasatinib, daunoblastin, daunorubicin/daunomycin, decitabine, deferasirox, deforolimus, demecolcine, denibulin, detorubicin, dexniguldipine, dexormaplatin, dezaguanine, dianhydrodulcitolum, dibrospidium chloride, dienogest, diflomotecan, dinalin, disermolide, docetaxel, dofequidar, dolasetron mesylate, dovitinib, doxifluridine, doxorubicin, dromostanolone, duazomycin, duocarmycin, dynemicin, ecomustine, edatrexate, edotecarin, edotreotide, eflornithine, elacridar, eacytarabine, elesclomol, elinafide, elomotecan, elsamitrucin, emitefur, enloplatin, enocitabine, enpromate, entecavir, entinostat, entricitabine, enzastaurin, epirubicin, eptaloprost, eribulin, erlotinib, Esorubicin, estramustine, etalocib, etanidazole, etoglucid, etoposide, exatecan, exemestane, exisulind, fadrozole, fazarabine, fiacitabine, floxuridine, fludarabine, fluoxymesterone, flurocitabine, flutamide, formestane, forodesine, fosfluridine tidoxil, fosquidone, fostriecin, fotemustine, fotretamine, fulvestrant, fumagillin, galarubicin, galocitabine, gefitinib, gemcitabine, gemtuzumab ozogamicin, geroquinol, gigantetronenin, gigantetroneninone, gimatecan, gimeracil, gloxazone, glufosfamide, goniothalamicin, goniothalamicinone, goserelin, granisetron HCl, gusperimus, hexarelin, homoharringtonine, hydrocamptothecine, hydroxycarbamide, hydroxyurea, hypericin, ibandronate sodium, ibandronic acid, idarubicin HCl, idronoxil, ifosfamide, ilmofosine, imatinib, imatinib mesylate, imexon, improsulfan, incadronate, indibulin, indisulam, inolitazone, inproquone, intiquinatine, intoplicine, iobenguane, irinotecan hydrochloride, irofulven, irsogladine, ispinesib, ixabepilone, ketotrexate, L-alanosine, laniquidar, lapatinib ditosylate, laromustine, larotaxel, ledoxantrone, lenalidomide, lentinan, lestaurtinib, letrozole, leuprolide acetate, leuprorelin, lexacalcitol, liarozole, lobaplatin, lomustine, lonafarnib, lonidamine, losoxantrone, Ly-83583, lysipressin, mafosfamide, mannomustine, mannosulfan, marimastat, marinomycin A, masitinib, maslinic acid, masoprocol, mechlorethamine, medorubicin, megestrol, mepitiostane, mercaptopurine, mesna, methotrexate, methyl amino levulinate, metomidate, metoprine, meturedepa, miboplatin, midostaurin, mifamurtide, milataxel, miproxifene, miriplatin, misonidazole, mitindomide, mitoflaxone, mitoguazone, mitomycin, mitonafide, mitoquidone, mitotane, mitoxantrone, mitozolomide, mivobulin, mizoribine, mofarotene, mopidamol, motesanib, motexafin, mubritinib, muricapentocin, muricatacin, mustine HCl, mycophenolate mofetil, mycophenolic acid, nedaplatin, nelzarabine, nemorubicin, neocuproine, neptamustine, neratinib, nigericin, nilotinib, nilutamide, nimustine, ninopterin, nitracrine, nogalamycin, nolatrexed, norcantharidine, nor-dihydroguaiaretic acid, nortopixantrone, novembichin, obatoclax, octreotide, olaparib, oleanolic aldehyde, omacetaxine mepesuccinate, ombrabulin, omtripolide, ondansetron HCl, ortataxel, oteracil, oteracil potassium, oxaliplatin, oxisuran, oxophenarsine, paclitaxel ceribate, palifosfamide, palonosetron, pamidronate disodium, pamidronic acid, panitumumab, panobinostat, patubilone, pazelliptine, pazopanib, pegaspargase, peldesine, pelitinib, pelitrexol, pemetrexed disodium, pentostatin, peplomycin, peretinoin, perfosfamide, perifosine, pibrozelesin hydrobromide, picoplatin, pinafide, pipo-sulfan, pirarubicin, pirfenidone, piritrexim, piroxantrone, pixantrone, plevitrexed, plicamycin, plitidepsin, plomestane, podophyllotoxin, pomalidomide, porfimer sodium, pralatrexate, prinomastat, procarbazine HCl, propamidine, prospidium chloride, pumitepa, puromycin, pyrazofurin, ouarfloxin, raltegravir, raltitrexed, ramosetron HCl, ranimustine, retaspimycin, retelliptine, riboprine, ritrosulfan, rituximab, roflumilast, romidepsin, ropidoxuridine, roquinimex, rosabulin, rubitecan, sabarubicin, safingol, salirasib, sapacitabine, saracatinib, sardomozide, satraplatin, sebriplatin, seliciclib, semaxanib; SU-5416, semustine, sermorelin, simotaxel, simtrazene, sitagliptin, sizofiran, soblitodin, sobuzoxane, sodium phenylbutyrate, sorafenib, sparfosic acid, sparsomycin, spiroplatin, squalamine, squamocin, streptonigrin, streptovarycin, streptozocin, sufosfamide, sulofenur, sunitinib, swainsonine, tacedinaline, tafluposide, talabostat, talisomycin, tallimustine, talotrexin, taltobulin, tamoxifen citrate, tandutinib, tanespimycin, tariquidar, tasidotin, tasisulam, tauromustine, tegafur, tegafur-uracil, telantinib, teloxantrone, temozolomide, teniposide, tenuazonic acid, terameprocol, teriparatide, tesetaxel, testolactone, tezacitabine, thiamiprine, thioguanine, thiotepa, thymopoietin, tiazofurine, tilomisole, tilorone, timcodar, timonacic, tioguanine, tirapazamine, tocladesine, tomudex, topotecan hydrochloride, toremifene citrate, tosedostat, tositumomab, toxipantrone, trastuzumab, trenimon, tretinoin, triciribine, trilostane, trimetrexate, triplatin tetranitrate, triptolide, triptorelin, trofosfamide, tropisetron HCl, tubulozole, tylophorin, U-67786, U-68415, U-71184, U-76074, U-78057, ubenimex, uramustine, uredepa, urethane, uridine, ursolic acid, ursolic aldehyde, vadimezan, valrubicin, valspodar, vandetanib, vapreotide, vatalanib; PTK-787, verteporfin, vildagliptin, vinblastine sulfate, vincristine, vindesine, vinepidine, vinflunine, vinformide, vinfosiltine, vinleucinol, vinleurosine, vinorelbine, vinorelbine tartrate, vintriptol, vinzolidine, voriconazole, vorinostat, vorozole, wilforlide A, xanthomycin A, zalcitabine, zeniplatin, zilascorb, zinostatin, zoledronic acid, zorubicin, zosuquidar, or a combination comprising at least one of the foregoing cancer inhibitors.

48. The article of claim 44, where the biologically active agent is selected from the group consisting of abacavir, abamectin, abanoquil, abaperidone, abarelix, abecamil, abiraterone, abitesartan, ablukast, abunidazole, acadesine, acamprosate, acaprazine, acebrochol, acebutolol, acecainide, acecarbromal, aceclidine, aceclofenac, acedapsone, acediasulfone, acedoben, acefluranol, acefurtiamine, acefylline clofibrol, acefylline piperazine, aceglatone, aceglutaminde, acemetacin, aceneuramicacid, acenocoumarol, acepeprone, acepromazine, aceprometazine, acequinoline, acesulfame, acetaminosalol, acetanilide, acetarsone, acetaminophen, acetazolamide, acetiamine, acetiromate, acetohexamide, acetophenazone, acetophenetidin, acetorphine, acetosulfone, acetriozoic acid, acetylcysteine, acetyldigitoxin, acetylleucine, acetyltributyl citrate, acetyltriethyl citrate, acevaltrate, acexamin acid, acifran, acipimox, acitazanolast, acitemate, acitretin, acivicin, alcantate, aclarubicin, aclatonium napadisilate, acolbifene, aconiazide, aconitine, acotiamide, acoxatrine, acreozast, acridorex, acriflavine, acrihellin, acrisorcin, acrivastine, acroinonide, acronine, actaplanin, actarit, actinoquinol, actisolide, actodigin, acyclovir, adafenoxate, adamexine, adapalene, adaprolol, adatanserin, adefovir, adekalant, adelmidrol, ademitrionine, adenosine, adibendal, adicillin, adimolol, adinazolam, adiphenine, aditeren, aditoprim, adosopine, adozelesin, adrafinil, adrenalone, adrogolide, afalanine, afeletecan, afloqualone, afovirsen, afurolol, aganodine, aglepristone, agomelatine, aklomide, alacepril, alafosfalin, alagebrium, alamecin, alamifovir, alanine, alanosine, alaproclate, alatrofloxacin, alazanine triclofenate, albaconazole, albendazole, albuterol, albutoin, alclofenac, alclometasone, alcloxa, alcuronium, aldioxa, aldosterone, alemcinal, alendronic acid, alentemol, alepride, alestramustine, aletamine, alexidine, alexitol, alexomycin, alfacalcidol, alfadex, alfidalone, alfaprostol, alfatradiol, aldaxalone, alfentranil, alfluzosin, algeldrate, algestone, alibendol, aliconazole, alifedrine, alifurane, alilusem, alimadol, alinastine, alinidine, alipaminde, aliskiren, alitame, alitretinoin, alizapride, alletorphine, allobarbitol, allocamide, allocupreide, allomethadione, allopurinol, allylestrenol, allylprodine, almecillin, almestrone, alminoprofen, almitrine, almokalant, almotriptan, almoxatone, almurtide, alnespirone, alniditan, alonacic acid, alonimid, aloracetam, alosetron, alovudine, aloxidone, aloxiprin, aloxistatin, alozafone, alpertine, alphameprodine, alphamethadol, alphamethyldopa, alphaprodine, alpidem, alpiropride, alprafenone, alprazolam, alprenolol, alprenoxime, alprostadil, alrestatin, altanserin, altapizone, alteconazole, althiazide, altinicline, altoqualiine, altrenogast, altretamine, alvemeline, alverine, alvimopan, alvocidib, amadinone, amafalone, amanozine, amantadine, amantocillin, ambamustine, ambasilide, ambazone, ambenonium, ambenoxan, ambomycin, ambrisentan, ambroxol, ambruticin, ambucaine, ambucetamide, ambuphylline, ambuside, ambutonium, amcinafal, amcinafide, amcinonide, amdinocillin, amdoxovir, ambucort, amedalin, amelometasone, ameltolide, amelubant, amesergide, ametantrone, amethocaine, amezapine, amezinium, amfenac, amfepentorex, amfetaminil, amflutizole, amfonelic, amicarbalide, amicloral, amicycline, anidantel, amidapsone, amidephrine, amiflamine, amifloverine, amifloxacin, amifostine, amiglumide, amikacin, amikhelline, amiloride, amiloxate, aminacrine, amindocate, amineptine, aminoglutethimide, aminohippuric acid, aminolevulinic acid, aminometradine, aminopentamide, aminophenazone, aminophylline, aminopromazine, aminopterin, aminopyrine, aminoquinol, aminoquinuride, aminorex, aminosalicylic acid, aminothiazole, amiodarone, amiperone, amphenazole, amipizone, amiprolose, amiquinsin, amisometradine, amisulprode, amiterol, amithiozone, amitivir, amitraz, amitriptyline, amitriptyinoxide, amixetrine, amlexanox, amlintide, amlodipine, amocarzine, amodiaquine, amolanone, amonafide, amoproxan, amopyroquine, amorolfine, amoscanate, amosulatol, amotosalen, amotriphene, amoxapine, amoxecaine, amoxicillin, amoxydramine, amperozide, anphechloral, amphenidone, amphetamine, amphomycin, amphotalide, amphotericin, ampicillin, ampiroxicam, amprenavir, amprolium, ampyrimine, ampyzine, amquinate, amrubicin, amsacrine, amtolmetin, amustaline, amylobarbital, angestone, anagrelide, anakinra, anaritide, anastrozole, anatibant, anaxirone, anazocine, anazolene, ancarolol, ancitabine, andolast, androstenediol, androstenedione, andulafungin, anecortave, anetholtrithion, angiotensin amide, andidoxamine, anidulafungin, anilamate, anileridine, anilopam, anipamil, aniracetam, anirolate, anisacril, anisindione, anisopirol, anisotropine, anisperimus, anitrazafen, anpirtoline, ansoxetine, antafenite, antazoline, antazonite, anthelmycin, anthralin, anthramycin, antipyrine, antrafenine, apadoline, apafant, apalcillin, apaxafylline, apaziquone, apazone, apicycline, aplindore, apomorphine, apovincamine, apraclonidine, apramycin, aprepitant, aprakalim, aprindine, aprinocarsine, apofene, aprosulate, aptazapine, aptiganel, aptocaine, aranidipine, aranotin, arbaprosil, arbekacin, arbutamine, arclofenin, ardacin, ardeparin, arecoline, arfalasin, arfendazam, arformoterol, argatroban, argimesna, argipressin, argiprestocin, arlidone, arimoclomol, aripiprazole, armodafinil, arnolol, arofylline, artinolol, arprinocid, arpromidine, arsanilic acid, arteflene, artemether, artemisinin, artemotil, artenimol, artesunate, articaine, artilide, arundic acid, arzoxifene, ascorbic acid, arsenapine, aseripide, asimadoline, asobamast, asocainol, asoprisnil, aspartame, aspartocin, asperlin, aspirin, aspoxicillin, astemizole, astromicin, asulacrine, atamestane, ataprost, ataquimast, atavanavir, atenolol, atevirdine, atibeprone, atilmotin, atipamezole, atipromod, atiprosin, atizoram, atliprofen, atocalcitol, atolide, atomoxetine, atorvastatin, atosiban, atovaquone, atracurium, atrasentan, atraleuton, atrimustine, atrinositol, atromepane, atropine, atropine oxide, auranofin, aurothioglucose, avanafil, avasimibe, avicatonin, avalamycin, aviptadil, avitriptan, avizafone, avobenzone, azoparcin, avorelin, avridine, axamozide, axitirome, axomadol, azabon, azabuperone, azacitidine, azacitidine, azaclorzine, azaconazole, azacosrterol, azacyclonol, azaftozine, azalanstat, azalomycin, azaloxan, azamethiphos, azamethonium, azamulin, azanator, azanidazole, azaperone, azapetine, azaquinzole, azaribine, azarole, azaserine, azasetron, azaspirium, azastene, azatadine, azathioprine, azelaic acid, azelastine, azelinnidipine, azepexole, azepindole, azetepa, azetirelin, azidamfenicol, azidocillin, azimexon, azimilide, azintamide, azipramide, azithromycin, azlocillin, azlocillin, azolimine, azosemide, aztomycin, aztreonam, azumolene, bacampicillin, bacitracin, baclofen, bacmecillinam, bakeprofen, balaglitazone, balazipone, balofloxacin, balsalazide, bamaluzole, bamaquimast, bambermycin, bambuterol, bamethan, bamifylline, bamipine, bamirastine, bamidazole, banoxantrone, baquiloprim, barbexaclone, barbital, barixibat, barmastine, barnidipine, barucainide, barusiban, basifungin, batalbulin, batanopride, batebulast, batelapine, batilol, batimastat, batoprozine, baxitoizine, bazedoxifene, bazinaprine, becanthone, becatecarin, beciparcil, beclamide, becliconazole, beclobrate, beclomethasone, beclotiamine, befetupitant, befiperide, befloxatone, befunolol, befuraline, bekanamycin, belaperidone, belarizine, belfosdil, belotecan, beloxamide, beloxepin, bemarinone, bemegride, bemesetron, bemetizide, beminafil, bemiparin, bemetradine, bemoradan, bemotrizinol, benactyzine, benafentrine, benapryzine, benaxibine, benazepril, bencianol, bencisteine, benclonidine, bencyclane, bendacalol, bendamustine, bendazac, bendazol, benderizine, bendroflumethazide, benethamine penicillin, benexate, benfluorex, benfosformin, benfotiamine, benflurodil, benhepazone, benidipine, benmoxin, benolizime, benorilate, benorterone, benoxifos, benoxaprofen, benoxinate, benpenolisin, benperidol, benproperine, benrixate, bensalan, benserazide, bensuldazic acid, bentazepam, bentemazole, bentiamine, bentipimine, bentiromide, bentoquatam, benurestat, benzalkonium, benzarone, benzbromarone, benzestrol, benzethidine, benzethonium, benzetimide, benzilonium, benzindopyrine, benziodarone, benzmalecene, benznidazole, benzobarbital, benzocaine, benzoclidine, benzoctamine, benzodepa, benzododecinium, benzonatate, benzopyrronium, benzoquinonium, benzotript, benzoxiquine, benzoxonium, benzoylpas, benzphetamine, benzpiperylon, benzpyrinium, benzquercin, benzquinamide, benzthiazide, benztropine, benzydamine, benzylhydrochlorothiazide, benzylpenicillin, benzylsulfamide, bepafant, beperidium, bephenium, bepiastine, bepridil, beractant, beraprost, berberine, berefrine, bergenin, berlafenone, bermoprofen, bertosamil, berupipam, bervastatin, berythromycin, besigomsin, besipirdine, besonprodil, besulpamide, besunide, beta carotene, betacetylmethadol, betahistine, betaine, betameprodine, betamethadol, betamethasone, betamicin, betamipron, betaprodine, betaxolol, betazole, bethanacol, bethanidine, betiatide, betoxycaine, bevantolol, bevonium, bexarotene, bexlosteride, bezafibrate, beztiramide, bialamicol, biapenem, bibezonium, bibrocathol, bilcalutamide, bicifadine, bicoldil, biclofibrate, biclotymol, bicozamycin, bidimazium, bidisomide, bietamiverine, bietaserpine, bifemelane, bifepramide, bifeprofen, bifeprunox, bifluranol, bifonazole, bilastine, bimakalim, bimatoprost, bimoclomol, bimosiamose, bindarit, binedaline, binfloxacin, binifibrate, biniramycin, binizolast, binodenosine, binospirone, bioallethrin, botin, bipenamol, biperiden, biphenamine, biricodar, biriperone, bisacodyl, bisantrene, bisaramil, bisbendazole, bisbentiamine, bisbutiamine, bisdequilinium, bisfenazone, bisfentidine, bisnafide, bisorbin, bisoctriazole, bisoprolol, bisorcic, bisoxatin, bispyrithione, bithonol, bithionoloxide, butipazone, bitolterol, bitoscanate, bivalirudin, bizelesin, bleomycin, blonanserine, bluensomycin, bofumustine, bolandiol, bolasterone, bolazine, boldenone, bolenol, bolmantalate, bometolol, bopindolol, bornaprine, bornaprolol, borelone, borocaptane, bortezomib, bosentan, botiacrine, boxidine, brallobarbital, brasofensine, brazergoline, brefonalol, bremazocine, brequinar, bretazenil, bretyllium, brifentanil, brimonidine, brinazaprone, brindoxime, brinzolamide, brivudine, brobactam, broclepride, brocrestine, brocrinat, brodimoprim, brofaromine, brofoxine, brolaconazole, brolamfetamine, bromadoline, bromamid, bromazepam, bromchlorenone, bromebric acid, bromerguride, brometenamine, bromfenac, bromhexene, bomindione, bromisovalum, bromociclen, bromocriptine, bromodiphenylhydramine, bromofenfos, bromofos, bromopride, bromoxanide, bromperidol, brompheniramine, broparestrol, broperamol, bropirimine, broquinaldol, brosotaminde, brostallicin, brosuximide, brotianide, brotizolam, brovanexine, brovincamine, broxaldine, broxaterol, broxitalamide, broxuridine, broxyquinoline, bucainide, bucetin, buciclovir, bucillamine, bucindolol, bucladesine, buclizine, buclosaminde, bucloxic acid, bucolme, bucricaine, bucromarone, bucumolol, budesonide, budipine, budotitane, budralazine, bufenadrine, bufeniode, bufetolol, bufexamac, bufezolac, buflomedil, bufogentin, buformin, bufrolin, bufuralol, bufylline, bulaquine, bumadizone, bumecaine, bumepidil, bumetanide, bumetriazole, bunaftine, bunamidine, bunamiodyl, bunaprolast, bunazosin, bunitrolol, bunolol, buparvaquone, bupicomide, bupivacaine, bupranolol, buprenorphine, bupropion, buquinerin, buquinolate, buquiterine, buramate, burodiline, buserelin, buspirone, busulfan, butobarbital, butacaine, butacetin, butaclamol, butadiazamide, butafosfan, butalamine, butalbital, butamben, butamirate, butamisole, butamoxane, butanilicaine, butanserin, butantrone, butaperazine, butaprost, butaverine, butedronate, bytenafine, buterizine, butenamate, buthiazide, butibufen, butifrine, butikacin, butilfenin, butinazocine, butinoline, butirosin, butixirate, butixocort, butobendine, butoconazole, butocrolol, butoctamide, butofiolol, butonate, butopamine, butopiprine, butoprozine, butopyrammonium, butorphanol, butoxamine, butoxylate, butriptyline, butropium, butylscopolamine, butynamine, buzepide, cabastine, cabergoline, cactinomycin, cadralazine, cadrofloxacin, cafaminol, cafedrine, caffeine, calcifediol, calciprotriene, calcitriol, calcobutrol, caldaret, caldiamine, caloxetic acid, calteridol, clausterone, camazepam, cambendazole, camaglibose, camiverine, camptothecin and its analogues, 9-amino camptothecin, 10-hydroxy camptothecin, 7-ethyl-10-hydroxy camptothecin, 9-nitro camptothecin and all other camptothecin analogues with six, seven and eight membered lactone rings, camonagrel, camostat, camylofin, canbisol, candesartan, candicidin, candocuronium, candoxatril, candoxatrilat, canertinib, canfosfaminde, cangrelor, cannabinol, canrenoate, canrenone, capectitabine, capobenate, capobenic acid, capravirine, capreomycin, capromorelin, caproxamine, capsaicin, captamine, captodiame, captopril, capuride, carabersat, caracemide, carafiban, caramiphen, carbachol, carbadox, carbamazepine, carbentel, carbasone, carbaspirin, carbazeran, carbazochrome, carbazocine, cabenicillin, carbenoxolone, carbenzide, carbetapentane, carbetocin, carbidopa, carbimazole, carbinoxamine, carbiphene, carbofenotion, carboplatin, carboprost, carboquone, carbubarb, carburazepam, carbutamide, carbuterol, carcainium, carebastine, carfentanil, carfimate, cargutocin, cariporide, carisoprodol, carmantadine, carmofur, carmoterol, carmustine, carnidazole, carnitine, carocainide, caroverine, caroxazone, carperidine, carperitide, carperone, carphenazine, carpindolol, carpipramine, carprazidil, carprofen, capronium, carsalam, carsatrin, cartasteine, cartazolate, carteolol, carubicin, carumonam, carvedilol, carvotroline, carzelesin, carzenide, casanthranol, casokefamide, caspofungin, cathine, cathinone, cebaracetam, cedefingol, cefaclor, cefadroxil, cefalonium, cefaloram, cefamandole, cefaparole, cefatriazine, cefazaflur, cefazedone, cefazolin, cefbuperazone, cefanel, cefcapene, cefclidin, cefdaloxime, cefdinir, cefditoren, cefedrolor, cefempidone, cefepime, cefetamet, cefetecol, cefetriaole, cefivtril, cefixime, cefmatilen, cefmenoxine, cefmepidium, cefmetazole, ceminox, cefodizime, cefonicid, cefoperazone, ceforanide, cefoselis, cefotaxime, cefotetan, cefotiam, cefovecin, cefoxazole, cofoxitin, cefozopran, cefpimizole, cefpiramide, cefpodoxime, cefprozil, cefquinome, cefrotil, cefroxadine, cefsulodin, cefsumide, ceftazidime, cefteram, ceftezole, ceftibuten, ceftioflur, ceftiolene, ceftioxide, ceftioxime, ceftriaxone, cefuracetamide, cefuroxime, cefuzonam, celecoxib, celgosivir, celiprolol, cemadotin, cephacetrile, cephadrine, cephalexin, cephaloglycin. Cephaloridine, cephalothin, cephapirin, cepharanthine, cephradine, cericlamine, cerivastatin, ceronapril, ceruletide, cetaben, cetalkonium, cetamolol, cetefloxacin, cethexonium, cethromycin, cetiedil, cetilistat, cetirizine, cetocycline, cetopheincol, cetotiamine, cetoxime, cetraxate, cetrimonium, cetylpyridinium, cevimeline, chaulmosulfone, chenodiol, chinofon, chloftbrate, chlophendianol, chloracyzine, chloralose, chlorambusil, chloramines-T, chloramphenicol, chlorazanil, chlorbenoxamine, chlorbetamide, chlorcyclizine, chlordantoin, chlordiazepoxide, chlordimorine, chlorhexidine, chlorindanol, chlorisondamine, chloramadione, chlormerodrin, chlormezanone, chlormidazole, chlornaphazine, chloroazodin, chloroprednisone, chloroprocaine, chloropyramine, chloroquine, chloroserpidine, chlorothen, chlorothiazide, chlorotrianisene, chloroxine, chloroxylenol, chlorphenesin, chlorpheniramine, chlorphenoctium, chlorphenoxamine, chlorphentermine, chlorproethazine, chlorproguanil, chlorpromazine, chlorpropamide, chlorprothixene, chlorpyrifos, chlortetracycline, chlorthalidone, chlorthenoxazine, chlorzoxazone, cholecalciferol, cholesterol, choline alfoscerate, choline, chromic chloride, chromonar, ciadox, ciaftalan, ciamexon, cianergoline, cianidanol, cianopramine, ciapilome, ciaprost, cicarperone, ciclactate, ciclafrine, ciclazindol, ciclesonide, cicletanine, cicliomenol, ciclonicate, ciclonium, ciclopirox, ciclopramine, cicloprofen, cicloprolol, ciclosidomine, ciclotizolam, ciclotropium, cicloxilic acid, cicloxolone, cicortonide, cidofovir, cidoxepin, cifenline, cifostodine, ciglitazone, ciheptolane, ciladopa, cilansertron, cilastatin, cilazapril, cilengitide, cilexin, cilnidipine, cilobamine, cilobradine, cilofungin, cilomilast, cilostamide, cilostazol, ciluprevir, cilutazoline, cimaterol, cimemoxin, cimetidine, cimetropium, cimicoxib, cimoxatone, cinacalcet, cinalukast, cinametic acid, cinamolol, cinanserin, cinaproxen, cinchophen, cinecromen, cinepazet, cinepazide, cinfenine, cinfenoac, cinflumide, cingestol, cinitapride, cinmetacin, cinnamaverine, cinnamedrine, cinnarizine, cinnofuradione, cinoctramide, cinodine, cinolazepam, cinoquidox, cinoxacin, cinoxate, cinoxolone, cinoxopazide, cinperene, cinprazole, cinpropazide, cinpromide, cintazone, cintriamide, cinuperone, cioteronel, cipamfylline, cipemastat, ciprafamide, cipralisant, ciprazafone, ciprefadol, ciprocinonide, ciprofibrate, ciprofloxacin, ciprokiren, cipropride, ciproquazone, ciprestene, ciramadol, cirazoline, cirolemycin, cisapride, cisatracurium, cinconazole, cismadinone, cisplatin, cistinexine, citalopram, citatepine, citenamide, citenazone, citicoline, citiolone, cizolirtine, cladribine, clamidoxic acid, clamikalant, clamoxyquin, clanfenur, clanobutin, clantifen, clarithromycin, clavulanate, clazolam, clazolimine, clazuril, clebopride, clefamide, clemastine, clemeprol, clemizole, clenbuterol, clenpirin, clentiazem, cletoquine, clevidipine, clevudine, clibucaine, clidafidine, clidanac, clindium, climazolam, climbazole, climiqualine, clinafloxacin, clindamycin, clinofibrate, clinolamide, clinprost, clioquinol, clioxanide, cliprofen, cliropamine, clobazam, clobenoside, clobenzepam, clobenorex, clobenztropine, clobetasol, clobetasone, clobutinol, clobuzarit, clocanfamide, clocapramine, clociguanil, clocinizine, clocortolone, clocoumarol, clodacaine, clodanolene, clodazon, clodoxopone, clodronate, clofarabine, clofazimine, clofenamic acid, clofeniclan, clofenetamine, clofenoxyde, clofevine, clofexamine, clofezone, clofibrate, clofibric acid, clofibride, clofilium, clofucarba, clofoctol, cloforex, clofurac, clogestone, cloguanamil, clomacrin, clomegestone, clometacin, clometherone, clomethiazole, clometocillin, clomifenoxide, clominorex, clomiphene, clomipramine, clomocycline, clomoxir, clonazepam, clonazoline, clonidine, clonitazine, clonixeril, clonixin, clopamide, clopenthixol, cloperastine, cloperidone, clopidogrel, clopidol, clopimozide, clopipazan, clopirac, cloponone, cloprendol, cloprostenol, cloprothiazole, cloquinate, cloquinozine, cloracetadol, cloranolol, clorazepate, clorazepic acid, clorethane, chlorexolone, clorfenvinos, clorgiline, cloricromen, cloridarol, clorindanic acid, clorindione, clormecaine, cloroperone, clorophene, cloroqualone, clorotepine, clorprenaline, clorsulon, clortermine, closantel, closiramine, clostebol, clothiapine, clothixamide, clotiazepam, cloticasone, clotioxone, clotixamide, clotrimazole, clovoxamine, cloxacepride, cloxacillin, cloxazolam, cloxestradiol, cloximate, cloxotestosterone, cloxypendyl, cloxyquin, clozapine, cobalamide, cocaine, codeine, codoxime, cofistatin, cogazocine, colchicines, colestolone, colfenamate, colforsin, co lfosceril, colimecycline, colterol, coluracetam, conessine, congazone, conivaptan, conorphone, cormethasone, corticorelin, cortisone, cortisuzol, cortivazol, cortodoxone, cotinine, cotriptyline, coumaphos, coumazolin, coumermycin, coumetarol, creatinine, creatinolfosfate, cresotamide, cridanimod, crilvastin, crisnatol, crobenetine, croconazole, cromakalim, cromitrile, cromoglicate lisetil, cromolyn, crolom, cronidipine, cropropamide, crotamiton, crotetamide, crotoniazide, crotoxyfos, crufomate, cuprimyxin, cuproxoline, cyacetacide, cyamemazine, cyanocobalamine, cyclacillin, cyclamate, cyclamic acid, cyclandelate, cyclarbamate, cyclazocine, cyclazodone, cyclexanone, cyclindole, cycliramine, cyclizine, cyclobarbital, cyclobendazole, cyclobenzaprine, cyclobutoic acid, cyclobutyrol, cyclocumarol, cyclofenil, cycloguanil, cycloheximide, cyclomenol, cyclomethycaine, cyclopentamine, cyclopenthiazide, cyclopentolate, cyclophenazine, cyclophosphamide, cyclopregnol, cyclopyrronium, cycloserine, cyclothiazide, cyclovalone, cycotiamine, cycrimine, cyfluthrin, cyhalothrin, cyheptamide, cyheptropine, cynarine, cypenamine, cypermethrin, cypothrin, cyprazepam, cyprenorphine, cyprodenate, cyproheptadine, cyprolidol, cyproquinate, cyproterone, cyproximide, cyromazine, cysteamine, cysteine, cystine, cytarabine, cycythiolate, dabelotine, dabigatran, dabuzalgron, dacarbazine, dacemazine, dacinostat, dacisteine, dacopafant, dactinomycin, dacuronium, dagapamil, dagluril, dalbavancin, dalbraminol, dalcotidine, daledalin, dalfopristin, dalteparin, daltroban, dalvastatin, dametralast, damotepine, danazol, daniquidone, danittracen, danofloxacin, danosteine, danthron, dantrolene, dapiprazole, dapitant, dapivirine, dapoxetine, dapsone, daptomycin, darbufelone, darenzepine, darglitazone, darifenacin, darodipine, darunavir, darusentan, dasantafil, dateliptium, daunorubicin, daxalipram, dazadrol, dazepinil, dazidamine, dazmegrel, dazolicine, dazopride, dazoquinast, dazoxiben, deboxament, debrisoquin, decamethonium, decimemide, decitabine, decitropine, declenperone, declopramide, decloxizine, decominol, decoquinate, dectaflur, deditonium, deferasirox, deferiprone, deferoxamine, deflazacort, defosfamine, defoslimod, degarelix, dehydroacetic acid, dehydrocholic acid, dehydroemetine, delanterone, delapril, delavirdine, delquamine, deergotrile, delfantrine, delfaprazine, selmadinove, delmetacin, delmpinol, delorazepam, deloxolone, delprostenate, deluceumine, dembrexine, demecarium, demeclocycline, demecolcine, demecycline, demegestone, demelverine, demexiptiline, democonazole, demoxepam, demoxytocin, denatonium, denaverine, denbufylline, denipride, denofungin, denopamine, denotivir, denpidazone, denufosol, denzimol, depelestat, depramine, depreotide, deprodone, deprostil, deptropine, dequalinium, deracoxib, deramciclane, deriglidole, derpanicaine, dersalazine, desapidin, desciclovir, descinolone, deserpidine, desipramine, deeslanoside, desloratidine, deslorelin, desmeninol, desmethylmoramide, desmopressin, desocriptine, desogestrel, desmorphine, desonide, desoximetasone, desoxycorticosterone, desvenlafaxine, detajmium, detanosal, deterenol, detirelix, deticiclovir, detromidine, detorubicin, detrothyronine, devapamil, devazepide, dexamethasone, dexamisole, dexbrompheniramine, dexbudesonide, dexchlorpheniramine, dexclamol, dexecadotril, dexefaroxan, dexetimide, dexetozoline, dexfenfluramine, dexfosfoserine, dexibuprofen, deximafen, dexindoprofen, dexivacaine, dexketoprofen, dexlo fexidine, dexloxiglumide, dexmedetomidine, dexmethylphenidate, dexnafenodonee, dexniguldipine, dexnorgestrel, dexormaplatin, dexoxadrol, dexpanthenol, dexpemedolac, dexpropranolol, dexproxibutene, dexrazoxane, dexsecoverine, dexsotalol, dextilidine, dextiopronin, dextofisopam, dextroamphetamine, dextrofemine, dextromethorphan, dextromoramide, dextrorphan, dextrothyroxine, dexcerapimil, sezaguanine, dezinamide, dezocine, diacerein, diacetamate, diacetolol, diamfenetide, diamocaine, diampromide, diamthiazole, diapamide, diarbarone, diathymosulfone, diatrizoate, diaveridine, diazepam, diaziquone, diazoxide, dibekacin, dibemethine, dibenzepin, dibenzothiophene, dibrompropamidine, bibromsalan, dibrospidium, dibucaine, dibuprol, dibupyrone, dibusadol, dicarbine, dicarfen, dichloralphenazone, dichloramine, dichlorisone, dichlormezanone, dichlorophen, dichlorphenarsine, dichloroxylenol, dichlorphenamide, dichlovos, diciferron, dicirenone, diclazuril, diclofenac, diclofenamide, diclofensine, diclofutrime, diclometide, diclonixin, dicloralurea, dicloxacillin, diclolinium, dicumrol, dicyclomine, didanosine, didrovaltrate, dieldrin, dienestrol, dienogest, diethadione, diethylphthalate, diethylcarbamazine, diethylpropion, diethylstilbestrol, dethylthambutene, diethyltoluamide, dietifen, difebarbamate, difemerine, difemetorex, difenamizole, difencloxazine, difenoximide, difenoxin, difetarsone, difeterol, diflomotecan, diflorasone, difloxacin, difluanine, diflucortolone, diflumidone, diflunisal, difluprednate, diftalone, digitalis, digitoxin, digoxin, dihexyverine, dihydralazine, dihydro codeine, dihydroergotamine, dihydrostreptomycin, dihydrotachysterol, diisobutylaminobenzoyloxypropyl theophylline, diisopromine, diisopropanolamine, diisopropylamine, dilazep, dilevalol, dilmefone, diloxanide, diltiazem, dimabefylline, dimadectin, dimecamine, dimeclonium, dimecrotic acid, dimefadane, dimefline, dimelazine, dimenhydrinate, dimenoxadol, dimepheptanol, dimepranol, dimepregnen, dimepropion, dimeprozan, dimesna, dimesone, dimetacrine, dimetamfetamine, dimethadione, dimethazan, dimethisoquin, dimethisterone, dimetholizine, dimethothizine, dimethoxanate, dimethylaminoethyl reserpilinate, dimethylthambutene, dimethyltubocurarinium, dimetipirium, dimetofrine, dimetridazole, diminazene, dimiracetam, dimoxamine, dimoxaprost, dimoxyline, dimpylate, dinaline, dinazafone, diniprofylline, dinitolmide, dinoprost, dinoprostone, dinsed, diohippuric acid, diosmin, diotyrosine, dioxadrol, dioxamate, dioxaphetyl butyrate, dioxation, dioxethedrin, dioxifedrine, dioxybenazone, dioxyline, dipenine, diperodon, diphemanil, diphenadione, diphenan, diphenchloxazine, diphenhydramine, diphenidol, diphenoxylate, diphenylpiperidinomethyldioxolan, diphenylpyraline, diphenoxazide, dipipanone, dipiproverine, dipivefrin, diprafenone, diprenorphine, diprobutine, diprofene, diprogulic acid, diproleandomycin, diprofylline, diproqualone, diproteverine, diprotrizoate, diproxadol, dipyridamole, dipyrithione, dipyrocetyl, dipyrone, diquafosol, dirithomycin, dirlotapide, disermolide, disquonium, disobutamide, sidofenin, sdisogluside, disopyramide, disoxaril, distigmine, disufenton, disulergine, disulfamide, disulfiram, disuprazoole, ditazole, ditekiren, ditercalinium, dithiaanine, ditiocade, ditiocarb, ditiomustane, ditolamide, ditophal, divabuterol, divalproex, divaplon, dixanthogen, dizatrifone, dizcilpine, dobesilate, dobupride, dobutamide, dobutamine, docarpamine, docebenone, docetaxel, doconazole, doconexent, docosanol, docusate, dodeclonium, dodicin, dofamium, dofequidar, dofetilide, dolasetron, doliracetam, domazoline, domiodol, domiphen, domipizone, domitroban, domoprednate, domoxin, domperidone, donepezil, donetidine, donitriptan, dopamantine, dopamine, dopexamine, dopropidil, doqualast, dorampimod, doramectin, doranidazole, dorastine, soreptide, doretinel, doripenem, dorzolamide, dosergoside, dosmalfate, dotarizine, dotefonium, dothiepin, doxacurium, doxapram, doxaprost, doxazosin, doxefazepam, doxenitoin, doxepine, doxergocalciferol, doxibetasol, doxifluridine, doxofylline, doxorubicin, doxpicomine, doxycycline, doxylamine, draflazine, dramedilol, draquinolo, drazidox, dribendazolew, drimidene, drobuline, drocinonide, droclidinium, drofenine, droloxifene, drometrizole, dromostanolone, dronabinol, drinedarone, dropempine, droperidol, droprenilamine, dropropizine, drospirenone, drotaverine, drotebanol, droxacin, droxicainide, droxicam, droxidopa, droxinavir, droxypropine, duazomycin, dulofibrate, duloxetine, dulozafone, dumorelin, dumetacin, duoperone, dupracetam, dutasteride, dyclonine, dyhydrogestrone, dymanthine, dyphylline, ebalzotan, ebastine, eberconazole, ebiratide, ebrotidine, ebselen, ecabapide, ecabet, ecadotril, ecalcidene, ecamsule, ecastolol, ecenofloxacin, echothiophate, eciprimidil, eclanamine, eclazolast, ecomustine, econazole, ecopipam, ecraprost, ectylurea, edaglitazone, edaravone, edatrexate, edelfosine, edetol, edifolone, edogestrone, edonentan, edotecarin, edotreotide, edoxudine, edratide, edronocaine, edrophonium, efaproxiral, efaroxan, efavirenz, efegatran, efepristin, efetozole, efletirizine, eflornithine, efloxate, eflucimibe, elfumast, efonidipine, efrotomycin, eganoprost, eglumetad, egtazic acid, equalen, elacridar, elantrine, elanzepine, elaarofiban, elbanizine, eldacimibe, eletriptan, elfazepam, elgotipine, elinafide, eliprodil, elisartan, ellagic acid, elliptinium, elmustine, elnadipine, elopiprazole, elsamitrucin, eltanolone, eltenac, eltoprazine, elucaine, elvucitabine, elzasonan, elziverine, emakalim, emapunil, embramine, embusartan, embutramide, emedastine, emepronium, emetine, emeglitate, emilium, emiteflur, emiverine, emodepside, emopamil, emorfazone, emtricitabine, emylcamate, enadoline, enalapril, enalaprilat, enalkiren, enazadrem, enbucrilate, encainide, enciprazine, enclomiphene, encyprate, endixaprine, endomide, endralazine, endrysone, enecadin, enefexine, enestebol, enfenamic acid, enfluvirtide, englitazone, eniclobrate, enilconazole, enilospirone, eniluracil, eniporide, enisoprost, enloplatin, enocitabine, enofelast, enolicam, enoxacin, enoxamast, enoxaparin, enoximone, enoxolone, enipiprazole, enpiroline, enprazepine, enprofylline, enpromate, enprostil, enramycin, enrasentan, enrofloxacin, ensacillin, ensulizole, entacapone, entecavir, entsufon, enviomycin, enviradene, enviroxime, enzacamene, anzastaurin, epalrestat, epanolol, eperezolid, eperisone, epervudine, ephedrine, epicainide, epicillin, epicriptine, epiestriol, epimestrol, epinastine, epinephrine, epinepheryl, epipropidine, epirizole, apiroprim, epirubicin, epitetracycline, epithiazide, epitiostanol, eplerenone, elivanserin, epoprostenol, epostane, eprazinone, eprinomectin, epristeride, eprobemide, eprosartan, eprovafen, eproxindine, eprozinol, epsipranel, epaloprost, eptapirone, eptaplatin, eptastigmine, eptazocin, eptifibatide, equillin, erbulozole, erdosteine, ergocalciferol, ergonovine, ergotamine, eritoran, erizepine, erlotinib, ercainide, ersentilide, ertapenem, ertiprotafib, erythrity tetrnitrate, erythromycin, esafloxacin, esaprazole, esatenolol, escitalopram, esculamine, eseridine, esflurbiprofen, esketamine, escarbazepine, esmolol, esomeprazole, esonarimod, esorubicin, esoxybutynin, espatropate, esproquin, estazolam, estradiol, estramustine, estrazinol, estriol, estrofurate, estrone, estropipaten esupone, eszopclone, etabenzarone, etacepride, etafedrine, etafenone, etalocib, etamestrol, etaminile, etamiphylline, etamocycline, etanidazole, etanterol, etaqualone, etarotene, etasuline, etazepine, etazolate, etebenecid, eterobarb, etersalate, ethacridine, ethacrynic acid, ehtambutol, ethamivan, ethamsylate, ethaverine, ethenzameide, ethiazide, ethinamate, ethinyl estradiol, ethionamide, ethisterone, ethoheptazine, ethomoxane, ethonam, ethopabate, ethopropazine, ethosuximide, ethotoin, ethoxazene, ethoxazorutoside, ethoxzolamide, ethybenztropine, ethyl biscoumacetate, ethyl carfluzepate, ethyl cartrizoate, ethyl dibunate, ethyl dirazepate, ethyl loflazepate, ethylestrenol, ethylhydrocupreine, ethylmethylthiambutene, ethylmorphine, ethylnorepinepherine, ethylstilbamine, ethylnerone, ethylnodil, ethypicone, etibendazole, eticlopride, eticyclidine, etidocaine, etidronate, etidronic acid, etifelmine, etifenin, etifoxine, etilamfetamine, etilefrine, etilevodopa, etinidine, etipirium, etiprendol, etiproston, etiracetam, etiroxate, etisazole, etisomicin, etisulergine, etizolam, etocarlide, etocrylene, etodolac, etodroxizine, etofamide, etofenamate, etofenprox, etofibrate, etofermin, etofuradine, etofylline, etoglucid, eorolex, etolotifen, etoloxamine, etomidate, etomidoline, etomoxir, etomitazene, etonogestrel, etoperidone, etoposide, etoprindole, etoprine, etoricoxib, etorphine, etosalamide, etoxadrol, etoxeridine, etozolin, etrabamine, etravirine, etretinate, etriciguat, etryptamine, etymemazine, eucaine, eucalyptol, eugenol, euprocin, evandamine, evernimicin, everolimus, evicromil, exalamide, exametazime, examorelin, exaprolol, exatecan, exemestane, exepanol, exifone, exiprofen, exisulind, ezetimibe, ezlopitant, fadolmidine, fadrozole, falecalcitriol, falintolol, falipamil, falnidamol, famciclovir, famirapinium, famotidine, famotine, fampridine, famprofazone, fampronil, fananserin, fanapanel, fandofloxacin, fandosentan, fanetizole, fantofarone, fantridone, farglitazar, fasidotril, fasiplon, fasoracetam, faudil, fazadinium, fazarabine, febantel, febarbamate, febuprol, febuverine, febuxostat, feclemine, feclobuzone, fedotozine, fedrilate, felbamate, felbinac, felipyrine, felodipine, feloprentan, felypressin, femoxetine, fenabutene, fenacetinol, fenaclon, fenadiazole, fenaftic acid, fenalamide, femalcomine, fenamifuril, fenamole, fenaperone, fenbendazole, fenbenicillin, fenbufen, fenbutreazate, fencamfamin, fencibutirol, fenclexonium, fleclofenac, fenclonine, fenclorac, fenclozic acid, fendiline, fendizoate, fendosal, feneritrol, fenestrel, fenethazine, fenethylline, fenetradil, fenflumizole, fenfluramine, flenfluthrin, fengabine, fenharmane, fenimide, feniodium, fenipentol, fenirfibrate, fenisorex, fenitrothion, fenleuton, fenmetozole, fenmetraminde, fenobam, fenocinol, fenocitimine, fenofibrate, fenoldopam, fenoprofen, fenoterol, fenoerine, fenoxazoline, fenoxedil, fenozolone, fenpentadiol, fenperate, fenprpalone, fenpipramide, fenpiprane, fenpiverinium, fenprinast, fenproporex, fenprostalene, fenquiaone, fenretinide, fenspiride, fentanyl, fenthion, fentiazac, fenticlor, fenticonazolem, fentonium, fenvalerate, fenyripol, fepentolic acid, fepitrizol, fepradinol, feprazone, fepromide, feprosidnine, ferpifosate, fesoterodine, fetoxylate, fexicaine, fexinidazole, fexofenadine, fezatione, fezolamine, fiacitabine, fialuridine, fibracillin, fidarestat, fidexaban, fiduxosin, figopitant, filaminast, filenadol, filipin, finafloxacin, finasteride, fingolimod, fipamezole, fipexide, fipronil, firocoxib, flavamine, flavodic acid, flavodilol, flavoxate, flazalone, flecainide, flerobuterol, fleroxacin, flesinoxan, flestolol, fletazepam, flezelastine, flibanserin, flindokalner, flocalcitriok floctafenine, flomoxef, floptopione, florantyrone, flordipine, floredil, florfenicok florifenine, flosatidil, flosequinan, flosulide, flotrenizine, floverine, floxacillin, floxacrine, floxuridine, flucizine, flualamine, fluanisone, fluazacort, fluazuron, flubanilate, flubendazole, flubepride, flucarbril, flucetorex, flucindole, flucinprazine, flucloronide, fluconazole, flucrylate, flucytosine, fludalanine, fludarabine, fludazonium, fludeoxyglucose, fludiazepam, fludorex, fludoxopone, fludrocortisone, flufenamic acid, flufenisal, flufosal, flufylline, flugestone, fluindarol, fluindione, flumazenil, flimecinol, flumedroxone, flumequine, flumeridone, flumethasone, flumethiazole, flumetramide, flumexadol, flumezapine, fluminorex, flumizole, flumoxonide, flunamine, flunarizine, flunidazole, flunisolide, flunitrazepam, flunixin, flunoprost, flunoxaprofen, fluocinolone, fluocinonide, fluocortin butyl, fluocortolone, fluorescein, fluoresone, fluorodopa, fluorometholone, fluorosalan, fluorouracil, fluotracen, fluoxetine, fluoxymesterone, fluparoxan, flupentixol, fluperamide, fluperlapine, fluperolone, flupheazine, flupimazine, flupirtine, flupranone, fluprazine, fluprednidene, fluprednisolone, fluprofen, fluprofylline, fluproquazone, fluprostenol, fluquazone, fluradoline, flurandrenolide, flurantel, flurazepam, flurbiprofen, fluretofen, flurithromycin, flurocitabine, flurofamide, flurogestone, flusoxolol, fluspiperone, fluspirilene, flutamide, flutazolam, flutemazepam, flutiazin, fluticasone, flutizenol, flutomidate, flutonidine, flutoprazepam, flutrimazole, flutroline, flutropium, fluvastatin, fluvoxamine, fluzinamide, fluzoperine, fodipir, folic acid, fomepizole, fomidacillin, fominoben, fomiversen, fomocaine, fonazine, fondaparinux, fopirtoline, forasartan, forfenimex, formebolone, formestane, formetorex, forminitrazole, formocortal, formoterol, forodesine, foropafant, fosamprenavir, fosarilate, fosazepam, fosenazide, fosfluconazole, fosfocreatinine, fosfomycin, fosfonet, fosfosal, fosfructose, fosinopril, fosinoprilat, fosmenic acid, fosmidomycin, fosopamine, fosphenyloin, fospirate, fosquidone, fostedil, fosrtriecin, fosveset, fotemustine, fortrenamine, fozivudine, frabuprofen, fradafiban, frakefamide, framycetin, frentizole, freselestat, fronepidil, fropenem, frovatriptan, froxiprost, ftaxilide, ftivazide, ftormetazine, ftorpropazine, fubrogonium, fudosteine, fuladectin, fulvestrant, fumagillin, fumoxicillin, fungimycin, fuprazole, furacrinic acid, furafylline, furalazine, furaltadone, furaprofen, furazabol, furazolidone, furazolium, furbicillin, furcloprofen, furegrelate, furethidine, furfenorex, furidarone, furmethoxadone, furnidipine, furobufen, furodazole, furofenac, furomazine, furomine, furosemide, furostilbestrol, fursalan, fursultiamine, furterene, furtrethonium, fusafungine, fusidate, fusidic acid, fuzlocillin, gabapentin, gabapexate, gaboxadol, gacyclidine, gadobenate, gadobutrol, gadocolectic acid, gadodiamine, gadofosveset, gadomelitol, gadopenamide, gadopentetate, gadoteric acid, gadoteridol, gadoversetamide, gadoxetate, gadoxeticaicid, galamustine, galntamine, galarubicin, galasomite, galdansetron, gallamine triethiodide, gallopamil, galocitabine, galosemide, galtifenin, gamfexine, gamolenic acid, gamaxolone, ganciclovir, ganefromycin, ganglefene, ganstigmine, gantacurium, gantoflban, gapicomine, gapromidine, garenoxacin, gatifloxacin, gavestinel, geclosporin, gedocarnil, gefarnate, gefitinib, gemazocine, gemcabene, gemcadiol, gemcitabine, gemeprost, genfibtrozil, gemifloxacin, gemopatrilat, gentamicin, gepefrine, gepirone, geroquinol, gestaclone, gestadienol, gestodene, gestonorone, gestrinone, gevotroline, gimatecan, gimeracil, giparmen, giracodazole, giractide, girisopam, gitaloxin, gitoformate, glafenine, glaspimod, glatiramer acetate, glemanserin, glenvastatin, gliamilide, glibotnuride, glibutimine, glicaramide, glicetanide, gliclazide, glicondamine, glidazamide, gliflumide, glimepiride, glipalamide, glipizide, gliquidone, glisamuride, glisentide, glisindamine, glisolamide, glisoxepide, gloxazone, gloximonam, glucametacin, glucosamine, gluronolactone, glucuronamide, glunicate, glyburide, glybuthiazole, glubuzole, gycopyrrolate, glycylamide, glyhexamide, glymidine, glyoctamide, glyparamide, glypinamide, glyprothiazole, glysobuzole, goralatide, goserelin, gramicidin, granisetron, grepafloxacin, griseofulvin, guabenxan, guacetisal, guafecainol, guaiactamine, guaiapate, guaietolin, guaifenesin, guaimesal, guaisteine, guaithylline, guanabenz, guanacline, guanadrel, guanazodine, guanclofine, guancydine, guanethidine, guanfacine, guanisoquin, guanoclor, guanoctine, guanoxabenz, guanoxan, guanoxyfen, gusperimus, halazepam, halazone, halcinonide, halethazole, halobetasol, halocortolone, halofantrine, halofenate, halofuginone, halometasone, halonamine, halopemide, halopenium, haloperidol, halopredone, haloprogesterone, haloprogin, haloxazolam, haloxon, haloqionol, hamycin, hedaquinium, heliomycin, hepronicate, heptabarbital, heptaverine, heptolamide, hepzidine, heroin, hetacillin, hetaflur, heteronium, hexachlorophene, hexacyclonate, hexacyprone, hexadiline, hexafluorenium, hexamethonium, hexaminolevulinate, hexapradol, hexaprofen, hexapropymate, hexasonium, hexazole, hexedine, hexestrol, hexetidine, hexobarbital, hexobendine, hexocyclium, hexoprenaline, hexopyrronium, heylcaine, histamine, histapyrrodine, histidine, homarylamine, homatropine, homidium, homochlorcyclizine, homofenazine, homopipramol, homosalate, homprenorphine, hopantenic acid, hoquizil, hycanthone, hydracarbazine, hydralazine, hydragaphen, hydrobentizide, hydrochlorothiazide, hydrocodone, hydrocortisone, hydroflumethiazide, hydromadinone, hydromorphinol, hydromorphone, hydroquinone, hydroxyindasate, hydroxyindasol, hydroxocobalamin, hydroxyamphetamine, hydroxychloroquin, hydroxydione, hydroxypethidine, hydroxyphenamate, hydroxyprocaine, hydroxyprogesterone, hydroxypyridine tartrate, hydroxystenozole, hydroxystilbamidine, hydroxytetracaine, hydroxyzine, hymecromone, hyoscyamine, ibafloxacin, ibandronate, ibazocine, ibopamine, ibrolipim, ibrotamide, ibudalast, ibufenac, ibuprofen, ibuproxam, ibutamoren, ibuterol, ibutilide, ibuverine, icaridin, icatibant, iclaprim, icazepam, icodulinium, icofungipen, ifometasone, icopezil, icosapent, icospiramide, icotidine, icrocaptide, idarubicin, idaverine, idazoxan, idebenone, idenast, idoxifene, idoxuridine, idralfidine, idramantone, idraparinux, idrapril, idremcinal, idrociliamide, idronoxil, idropranolol, iferanserin, ifetroban, ifosfamide, ifoxetine, iganidipine, igmesine, iguratimod, ilaprazole, ilatreotide, ilepcimide, iliparcil, ilmofosine, iloomastat, ilonidap, iloperidone, imafen, imanixil, imatinib, imazodan, imcarbofos, imiclopazine, imidafenacin, imidapril, imidaprilat, imidocarb, imidoline, imidurea, imiglitazar, imiloxan, iminophenimide, imipenem, imipramine, impiraminoxide, imiquimod, imirestat, imitrodast, imolamine, imoxiterol, impacarzine, implitapide, impromidine, improsulfan, imuracetam, inamirone, inaperisone, incadronic acid, indacaterol, indacrinone, indalpine, indanazoline, indanidine, indanorex, indapamide, indatraline, indecainide, indeloxazine, indenolol, indibulin, indigotindisulfonate, indinavir, indiplon, indisetron, indobufen, indocate, indocyanine green, indolapril, indolidan, indomethacin, indopanolol, indopine, indoprofen, indoramin, indorenate, indoxole, indriline, inecalcitol, ingliforib, inicarone, inocterone acetate, inogatran, inosine, inositol, improquoone, intoplicine, intrazole, intriptyline, inulin, iobenguane, iobenzamic acid, iobitridol, iobutoic acid, icanlidic acid, iocarmic acid, iocetamic acid, iodamine, iodipamide, iodixanol, iodoantipyrine, iodocholesterol, iodohippurate, iodoquinol, iodothiouracil, idoxamic acid, iofetamine, ioflupane, iofratol, ioglicic acid, ioglucol, ioglunide, ioglycamic acid, iogulaamide, iohexol, iolidonic acid, iolixanic acid, iolopride, iomazenil, iomeglamic acid, iomeprol, iomethin, iometopane, iomorinic acid, iopamidol, iopanoic acid, iopentol, iophendylate, iophenoxic acid, iopromide, iopronic acid, iopydol, iopydone, iosarcol, isofenamic acid, ioseric acid, iosimenol, iosimide, iosulamide, iosumetic acid, iotasul, ioteric acid, iothalamate, iothalamic acid, iotranic acid, iotriside, iotrizoic acid, iotrolan, iotroxic acid, iotyrosine, iovesol, ioxabrolic acid, ioxaglic acid, ioxilan, ioxitalamic acid, ioxotrizoic acid, iozomic acid, ipamorelin, ipazilide, ipenoxazone, ipexidine, ipidacrine, ipodate, iprgratine, ipramidil, ipratropium, ipravacaine, iprazochrome, ipriflavone, iprindole, ipocinidine, iproclozide, iprocrodol, iprofenin, iproheptine, iproniazide, ipronidazole, iproplatin, iprotiazem, iproxamine, iprozilamine, ipsalazide, ipsapirone, iquindamine, iralukast, irampanel, irbesartan, irindalone, irinotecan, irloxacin, irofulven, irolapride, iroxanadine, irsogladine, irtemazole, isalidole, isalsteine, isamfazone, isamoltan, isamoxole, isatoribine, isaxonine, isbogrel, isbufylline, ispamicin, isoamilinile, isobromindione, isobucaine, isobutamben, isocarboxazid, isoconazole, isocromil, isoetharine, isoflupredone, isoflurophate, isomazole, isomerol, isometamidium, isomethadone, isomethadone, isomethepdene, isomolpan, isoamylamine, isoniazid, isonixin, isoprazole, isoprednidene, isoprofen, isopropamide, isopropicillin, isoproterenol, isosrbide, isospaglumic acid, isosulfan blue, isosulpride, isothipendyl, isotiquimide, isotretinoin, isoxaprolol, isoxepac, isoxicam, isoxsuprine, isradipine, israpafant, istrdefylline, itameline, itanoxone, itasetron, itazigrel, itopride, itraconazole, itriglumide, itrocainide, itrocinonide, iturelix, ivbradine, ivarimod, ivermectin, ivoqualine, ixabepilone, izonsteride, josamycin, kainic acid, kalafungin, kanamycin, kebuzone, keracyanin, ketamine, ketanserin, ketazocine, ketazolam, kethoxal, ketipramine, ketobemidone, ketocaine, ketocainol, ketoconazole, ketoprofen, ketorfanol, ketorolac, ketotifen, ketotrexate, khellin, khelloside, kitasamycin, labetalol, labradimil, lachesine, lacidipine, lacosamide, lactalfate, lactilol, lactulose, ladirubicin, ladostigil, laflunimus, lafutiine, laidlomycin propionate, lamifiban, lamivudine, lamotrigine, lamitidine, lanatoside, landiolol, lanepitant, lanicemine, laniquidar, lanoconazole, lanperisone, lanproston, lanreotide, lansoprazole, lapatinib, lapisteride, laprafylline, lapyrium, laquinimod, lasalocid, lasinavir, lasofoxifene, latanoprost, laudexium, laurcetium, laurocapram, lauroguadine, laurolinium, lauryl isoquinolinium, lavoltidine, lazabemide, lecimibide, ledazerol, ledoxantrone, lefetamine, leflunomide, lefradafiban, leiopyrrole, lemidosul, lemidipine, leminoprazole, lemoxinol, lemuteporfin, lanalidomine, lenampicillin, lenapenem, leniquisin, leuperone, leptacline, lercanidipine, lergotrile, lerisetron, lesoptiron, lestaurtinib, leteprinim, leteprinim, letimide, letosteine, letrazuril, letrozole, leucinocaine, leucocianidol, leucovorin, leurubicin, levalbuterol, levallorphan, levamfetamine, levamisole, levcromakalim, levcycloserine, levdobutamine, levemoamil, levetiracetam, levisoprenaline, levlofexidine, levmetamfetamine, levobetaxolol, levobunolol, levobupiacaine, levocabastine, levocamitine, levodopa, levodropropizine, levofacetoperane, levofenfluramine, levofloxacin, levofluraltadone, levoleucovorin, levomenol, levomepromazine, levomethadone, levomethadyl acetate, levomethorphan, levometiomeprazine, levomoprolol, levomoramide, levonantradol, levonordefrin, levonorgestrel, levophenacylmorphan, levopropoxyphene, levopropuylcilline, levopropuylhexedrine, levoprotiline, levorin, levormeloxifene, levorphanol, levosalbutamol, levosemotiadil, levosimendan, levosulpiride, levothyroxine, levotofisopam, levoxadrol, lexipafant, lexithromycin, lexofenac, liarozole, libecillide, libenzapril, licarbazepine, licofelone, licostinel, lidadronic acid, lidamine, lidanserin, lidocaine, lidoferin, lidorestat, lifariaine, lifibrate, lifibrol, lilopristone, limaprost, limazocic acid, linarotene, lincomycin, lindane, linetastine, linezolid, linogliride, linopirdine, linotroban, lisinidomine, lintitript, lintopride, liothyronine, lipoic acid, liraglutide, liranaftate, lirequinil, lirexapride, lirimilast, liroldine, lisadimate, lisinopril, lisofylline, lisuride, litomeglovir, litoxetine, litracen, lividomycin, lixazinone, lixivaptan, lobapolatin, lobeline, lobendazole, lobenzarit, lobucavir, lobuprofen, locicortolone, lodaxaprine, lodazecar, lodelaben, lodenosine, lodinixil, lodiperone, lodoxamide, lofemizole, lofendazam, lofentanil, lofepramine, lofexidine, loflucarban, lombazole, lomefloxacin, lomeguarib, lomerizine, lometraline, lometrexol, lomevactone, lomifylline, lomofungin, lomustine, lonafarnib, lonapalene, lonaprofen, lonazolac, lonidamine, loperamide, lopinavir, lopirazepam, lopobutan, loprazolam, loracarbef, lorajmine, lorapride, lorazepam, lorbamate, lorcainide, lorcinadol, loreclezole, lorglumide, lormetazepam, lornoxicam, lopiprazole, lortalamine, lorzafone, losartan, losigamone, losindole, losmiprofen, losoxantrone, losulazine, loteprednol, lotrafiban, lotrifen, lotucaine, lovastatin, loviride, loxanast, loxapine, loxiglumide, loxoprofen, loxoribine, lozilurea, lubazodone, lubeluzole, lubiprostone, lucanthone, lucartamide, lucimycin, lufenuron, lufironil, lufuradom, luliconazole, lumiracoxib, lupitidine, luprostiol, lurasidone, lurosetron, lurototecan, lusaperidone, luxabendazole, lydimycin, lymecycline, lynestrenol, lypressin, mabuprofen, mabuterol, maduramicin, mafenide, mafoprazine, mafosfamide, malathion, maleylsulfathiazole, malotilate, mangafodipir, manidipine, manifaxine, mannomustine, manozodil, mantabegron, mapinastine, maprotiline, maraviroc, marbofloxacin, maribavir, maridomycin, marimastat, mariptiline, maropitant, maroxepin, masoprocol, maxacalcitol, maytansine, mazapertine, mazaticol, mazindol, mazipredone, mazokalim, mebanazine, mebendazole, menbenoside, mebeverine, mebezonium, mebhydrolin, mebiquine, mebolazine, mebrofenin, mebutamate, mebutizide, mecamylamine, mecarbinate, mecetronium, meciadanil, mecinarone, meclinertant, meclizine, meclocycline, meclofenamaic acid, meclofenoxate, meclonazepam, mecloqualone, meclorisone dibutyrate, mecloxamine, mecobalamin, medazepam, medazomide, medetomidine, medibazine, medifoxamine, medorinone, medorubicin, medrogestrone, medronic acid, medroxalol, medroxyprogesterone acetate, medrylamine, medrysone, mefeclorazine, mefenamic acid, mefenidil, mefenidramium, mefenorex, mefeserpine, mefexamide, mefloquine, mefruside, megalomyciin, megestrol, megace, meglitinide, meglucycline, meglumine, meglutol, meladrizine, melagatran, melarsomine, melarsonyl, melarsoprol, meldonium, melengestrol acetate, meletimide, melevodopa, melinamide, melitracen, melizame, meloxicam, melperone, melphalan, melquinast, meluadrine, mamantine, memotine, menabitan, menadiol, menadione, menadoxime, menatetrenone, menbutone, menfegol, menglytate, menitrazepam, menoctone, menogaril, menobentine, mepazine, mepenzolate, meperidine, mephenesin, mephenoxalone, mephentermine, mephenyloin, mephobarbital, mebaral, mepindolol, mepiperphenidol, mepiprazole, mepiroxol, mepitiostane, mepivacaine, mepixanox, mepramidil, meprednisone, meprobamate, meprochol, meproscillarin, meprotixol, meprylcaine, meptazinol, mequidox, mequinol, mequitamium, mequitazine, meradimqate, menthyl anthranilate, merafloxacin, meralein, meralluride, merbaphen, merbromin, mercaptomerin, mercaptopurine, mercuderamide, mercufenol, mercumatilin, mergocriptine, meribendan, merimepodib, meropenem, mersalyl, mertialide, mesabolone, mesalamine, meseclazone, mesocarb, mesoridazine, mesipiperone, mespirenone, mestanolone, mesterolone, mestranol, mesudipine, mesulergine, mesulfamide, mesulfen, mesuprine, metabromsalan, metbutethamine, metabutoxycaine, metacetamol, metaclazepam, metacresol, metaglycodol, metahexamide, metalkonium, metalol, metamelfalan, metamfazone, metamfenpramone, metampicillin, metanixin, metapramine, metaproterenol, metaraminol, metaxalone, metazamide, metazide, matazocine, metbufen, meteneprost, metergoline, metergotamine, metescufylline, metesculetol, metesind, metetoheptazine, metformin, methacholine, methacycline, methadone, methadyl acetate, methallenestril, methallibure, methalthiazide, methamphetamine, methandriol, methandrostenolone, methaniazide, methantheline, methaphenilene, methapyrilene, methaqualone, metharbital, methastyridone, methazolamide, methdilazine, methenamine, methenolone, metheptazine, methestrol, methetoin, methikcillin, methimazole, methiodal, methiomeprazine, methionine, methisazone, methitural, methixene, methocarbamol, methocidin, methohexital, methopholone, methoprene, methoserpidine, methotrexate, methotrimeprazine, methoxamine, methoxsalen, methoxyphedrine, methoxyphenamine, methoxypromazine, methscopolamine, methsuximide, methyclothiazide, methyl aminolevulinate, methyl palmoxirate, methyl salicylate, methylatropine, methylbenactyzium, methylbenzethonium, methylcromone, methyldesorphine, methyldihydromorphine, methyldopa, methylene blie, methylephedrine, methylergometrine, methylergonovine, methylparaben, methylphenidate, methylprednisolone, methyltestosterone, methylthiouracil, methynodiol, methyprylon, methysergide, metiamide, metiapine, metiazinic acid, metibride, meticrane, metildigoxin, metindizate, metioprim, metioxate, metipirox, metiprenaline, metitepine, metizoline, metkephamid, metochalcone, metocinium, metoclopramide, metocurine, metofenazate, metogest, metolazone, metomidate, metopimazine, metopon, metoprine, metoprolol, metoquizine, metoserpate, metostilenol, metoxepin, metrafazoline, metralindole, metrazifone, metrenperone, metribolone, metrifonate, metrifudil, metrizamide, metrizoate, metronidazole, meturedepa, metyrapone, metyrosine, mevastatin, mexafylline, mexazolam, mexenone, mexiletine, mexiprosil, mexoprofen, mexrenoate, mezacopride, mezepine, mezilamine, mezlocillin, miaanserin, mibefradil, mibolerone, mieboplatin, micafungin, miconazole, micronomicin, midaflur, midafotel, midaglizole, midamaline, midaxifylline, midazogrel, midazolam, midecamycin, midestein, midodrine, midostaurin, mifentidine, mifepristone, mifobate, miglitol, miglustat, mikamycin, milacainide, milacemide, milameline, milataxel, milenperone, milfasartan, milipertine, miloxacin, milrinone, miltefosine, milverine, mimbane, minalrestat, minamestane, minaprine, minaxolone, mindodilol, mindoperone, minepentate, minocromil, minocycline, minodronic acid, minopafant, minoxidil, mioflaazine, mipitroban, mipragoside, miproxifene, mirfentanil, mirincamycin, miripirium, miriplatin, mirisetron, miristalkonium, miroprofen, mirosamicin, mirostipen, mirtazapine, misonidazole, misoprostol, mitemcinal, mitiglinide, mitindomine, mitobronitol, mitocarcin, mitoclomine, mitocromin, mitoflaxone, mitogillin, mitoguazone, mitolactol, mitomalcin, mitomycin, mitonafide, mitopodozide, mitoquidone, mitosper, mitolane, mitotenamine, mitoxantrone, mitozolomide, mitradipide, mivacurium, mivobulin, mivotilate, mixidine, mizolastine, mizoribine, mobecarb, mobenzoxamine, mocimycin, mociprazine, moclonemide, moctamide, modafinil, modaline, modecainide, modipafant, moexipril, moexiprilat, mofarotene, mofebtazone, mofegiline, mofezolac, mofloverine, mofoxine, mofuisteine, molfarnate, molinazone, molindone, molracetam, molsidomine, mometasone, monalazone, monatepil, monesin, monobenzone, monoctanoin, monometacrine, monophosphothiamine, monoxerutin, montelukast, monterelin, moperone, mopidamol, mopidralazine, moprolol, moquizone, morantel, morazone, morclofone, morforex, moricizine, morinamide, momiflumate, morocromen, moroxydine, morpheridine, morphine, morsuximide, mosapramine, mosapride, motapizone, motexafin, motrazepam, motrtinide, moveltipril, moxadolen, moxalactam, moxaprindine, moxastine, moxaverine, moxazocine, moxestrol, moxicoumone, moxidectin, moxifloxacin, moxilubant, moxipraquine, moxirapine, moxisylate, moxnidazole, moxonidine, mozavaptan, mozenavir, mubritnib, mupirocin, murabutide, muraglitazar, mureletecan, murocainide, muzolimine, mycophenolic acid, myfadol, myrophine, myrtecaine, nabazenil, nabilone, nabitan, naboctate, nabumetone, nacartocin, nadide, nadiofloxacin, nadolol, nadoxolol, nafagrel, nafamostat, nafarelin, nafazatrom, nafcaproic acid, nafcillin, nafenodone, nafenopin, nafetolol, nafimidone, nafiverine, naflocort, nafomine, nafoxadol, nafoxidine, nafronyl, naftalofos, naftazone, naftifine, naftopidil, naftoxate, naftypamide, naglivan, nalbuphine, nalfurafine, nalidixic acid, nalmefene, nalmexone, nalorphine, naloxone, naltrexone, naminidil, naminterol, namirotene, namoxyrate, nanafrocin, nandrolone, nanterinone, nantradol, napactadine, napamezole, naphazoline, naphthonone, napirimus, napitane, naproxime, naproxen, naproxol, napsagatran, naranol, narasin, naratriptan, nardetoterol, naroparcil, natamycin, nateglinide, navuridine, naxagolide, naxaprosteine, naxifylline, nealbarbital, nebantan, nebidrazine, nebivolol, neboglamine, nebracetam, nebramycin, necopidem, nedaplatin, nedocromil, nefazodone, nefiracetam, neflumozide, nefopam, nelarabine, neldazosin, nelezaprine, nelfinavir, neltenexine, nelzarabine, nemadectin, nemazoline, nemifitide, nemonapride, nemorubicin, neocinchophen, neomycin, neostigmine, nepadutant, nepafenac, nepaprazole, nepicastat, nepinalone, nequinate, neramexane, neraminol, nerbacadol, neridronic acid, nerisopam, nesapidil, nesiritide, nesosteine, nestifylline, neticonazole, netilmicin, netivudine, netobimin, netoglitazone, netupitant, neutramycin, neviparine, nexeridine, nexopamil, niacin, niacinamide, nialamide, niaprazine, nibroxane, nicafenine, nicainoprol, nicametane, nicanartine, nicaraven, nicarbazin, nicardipine, nicergoline, niceritol, niceverine, niclofolan, niclosamide, nicoboxil, nicoclonate, nicocodine, nicocortonide, nicocidodine, nicoduozide, nicofibrate, nicofuranose, nifurate, nicogrelate, nicomol, nicomorphine, nicopholine, nicoracetam, nicorandil, nicothiazone, nicotredole, nicoxamat, nictiazem, nictindole, nidroxyzone, nifedipine, nifekalant, nifenalol, nifenazone, niflumic acid, nifungin, nifiradene, nifuraldezone, nifuralide, nifuratel, nifuratrone, nifurdazil, nifurethazone, nifurfoline, nifurimide, nifurizone, nifurmazole, nifurmerone, nifuroquine, nifuroxazide, nifuroxime, nifurpipone, nifurpirinol, nifirprazine, nifurquinazol, nifursemizone, nifursol, nifurthiazole, nifurtimox, nifurtoinol, nifurvidine, nifurzide, nigludipine, nihydrazone, nikethamide, nileprost, nilprazole, niludipine, nilutamide, nilvadipine, nimazone, nimesulide, nimetazepam, nimidane, nimodipine, nimorazole, nimustane, neometacin, niperotidine, nipradilol, niprofazone, nitavoline, nirdazole, nisbuterol, nisobamate, nisoldipine, nisoxetine, nisterime, nitarsone, nitazoxanide, nitecapone, nithiamide, nitisinone, nitracrine, nitrafudan, nitralamine, nitramisole, nitraquazone, nitrazepam, nitrefazole, nitrendipine, nitrocefin, nitroclofene, nitrocycline, nitrodan, nitrofurantoin, nitrofurazone, nitromersol, nitromide, nitromifene, nitroscanate, nitrovin, nitroxinil, nitroxoline, nivazol, nivimedone, nizatidine, nizofenone, noberastine, nocloprost, nocodazole, nofecainide, nogalamycin, nolatrexed, nolinium, nolomirole, nolpitantium, nomegestrol, nomelidine, nomifensine, nonabine, nonaperone, nonapyrimine, nonathymulin, nonivamide, noracymethadol, norbolethone, norbudroine, norcholestenol, norclostebol, norcodeine, nordazepam, nordefrin, nordinone, norelgestromin, norepinepherine, norethandrolone, noethindrone, norethynodrel, noreximide, norfenefrine, norfloxacin, norgesterone, norgestimate, norgestomet, norgestrel, norgestrieneone, norletimol, norlevorphenol, normethadone, normorphine, norpipanone, nortetrazepam, nortopixantrone, nortriptyline, norvinisterone, nosantine, noscapine, nosiheptide, novobiocin, noxiptiline, noxytiolin, nuclomedone, nuclotixene, nufenoxole, nupafant, nuvenzepine, nylestriol, nylidrin, nystatin, obidoxime, ocaperidone, ocfentanil, ociltide, ocinaplon, octacaine, octafonium, octamoxin, octapinol, octatine, octaverine, octazamide, octenidine, octicizer, octimibate, octinoxate, octisalate, octocrylene, octodrine, octopamine, octotiamine, octreotide, octriptyline, octriazole, odalprofen, odapipam, odiparcil, ofloxacin, ofomine, oftasceine, oglufanide, olaflur, olamufloxacin, olanexidine, olanzapine, olaquindox, olcegepant, oleandomycin, oletimol, olmesartan, olopatadine, olpadronic acid, olpimedone, olprinone, olradipine, olsalazine, oltipraz, olvanil, omaciclovir, omapartrilat, omeprazole, omidoline, omigapil, omiloxetine, omoconazole, omonasteine, onapristone, ondansetron, ontazolast, ontianil, opanixil, opaviraline, opiniazide, opipramol, opratonium, orazamide, orazipone, orbofiban, orbutopril, orconazole, orientiparcin, oritavancin, orlistat, ormaplatin, ormeloxifene, ormetoprin, ornidazole, ornipreessin, ornithine, ornoprostil, orotic acid, orotirelin, orpanoxin, orphenadrine, ortataxel, orteteamine, osanetant, osaterone, oseltamivir, osemozotan, osmadizone, ospemifene, ostreogrycin, osutidine, otamixaban, otenzepad, oteracil, otilonium, otimerate, ouabain, oxabolon, oxabrexine, oxaceprol, oxacillin, oxadimedine, oxaflozane, oxaflumazine, oxagrelate, oxalinast, oxaliplatin, oxamarin, oxametacin, oxamisole, oxaminiquinem oxanamide, oxandrolone, oxantel, oxapadol, oxapium, oxaprazine, oxaprotiline, oxaprozin, oxcarbazole, oxatomide, oxazafone, oxazepam, oxazidone, oxazolam, oxazorone, oxcarbazepine, oxdralazine, oxeclosporin, oxedrine, oxeglitazar, oxeladin, oxendolone, oxepinac, oxetacillin, oxethazine, oxetorone, oxfendazole, oxfenicine, oxibendazole, oxibetaine, oxiconizole, oxidapamine, oxidronic acid, oxfentorex, oxifungin, oxigluttione, oxilofrine, oxilorphan, oximonam, oxindanac, oxiniacic acid, oxperomide, oxiracetam, oxiramide, oxisopred, oxisuran, oxitefonium, oxitriptan, oxitriptyline, oxtriponium, oxmetidine, oxodipine, oxogestone, oxolamine, oxolinic acid, oxomermazine, oxonazine, oxophenarsine, oxoprosto;l, oxpheneridine, oxprenoate, oxprenolol, oxtriphylline, oxbenzone, oxybutynin, oxychlorosene, oxycinchophen, oxyclipine, oxyclozanide, oxycodone, oxydipentonium, oxyfedrine, oxymesterone, oxymetazoline, oxymethalone, oxymorphone, oxypendyl, oxypertine, oxyphenbutazone, oxyphencyclimine, oxyphenisatin, oxyphenonium, oxypurinol, oxypurronium, oxyquinoline, oxyridazine, oxysonium, oxytetracycline, oxytocin, ozagrel, ozagamicin, ozolindone, paclitaxel, pacrindolol, pactimibe, padimate A, padimate Q, pafenolol, pagoclone, paldimycin, palinavir, paliperidone, palmidrol, palmoxirate, palonidipine, palonosertron, palosuran, pamabron, pamaqueside, pamaquin, pamicogrel, pamidronic acid, panadiplon, panamesine, pancopride, pancuronium, panipenem, panomifene, pantenicate, pantethine, panthenol, pantoprazole, panuramine, papverine, papveroline, parachlorphenol, paraflutizide, paramethadione, paramethasone acetate, paranitrosulfathiazole, paranyline, parapenzolate, parapropamol, pararosaniline, paraxazone, parbendazole, parcetasal, parconazole, parecoxib, pareptide, parethoxycaine, pargeverine, pargolol, pargyline, paricalcitol, paridocaine, parodilol, paromomycin, paroxetine, paroxypropione, parsalmide, particin, parvaquone, pasiniazid, pasireotide, patamostat, patupilone, paulomycin, paxamate, pazelliptine, pazinaclone, paxoxide, pazufloxacin, pecilocin, pecocycline, pefloxocin, pelanserin, peldesine, peliomycin, pelitinib, pelitrexol, pelretin, pelrinone, pelubiprofen, pemedolac, pemerid, pemetrexed, pemirolast, pemoline, penamecillin, penbutolol, penciclovir, pendecamine, pendetide, penfluridol, penflutizide, pengitoxin, penicillamine, penicillin G, penicillin V, penimepicycline, penimocycline, penirolol, penmesterol, penoctonium, penprostene, pentabamate, pentacynium, pentfluranol, pentagastrin, pentagestrone, pentalamide, pentamethonium, pentamidine, pentamorphone, pentamoxane, pentamustine, pentapiperide, pentapiperium, pentaquine, pentazocine, pentetic acid, pentreotide, penthienate, penthrichloral, pentiapine, pentifylline, pentigetide, pentisomicin, pentisomeide, pentizidone, pentobarbital, pentolinium, pentolonium, pentomone, pentopril, pentorex, pentosalen, pentostatin, pentoxifylline, pentoxyverine, pentrinitrol, pentylenetetrazol, peplomycin, pepstatin, peraclopone, peradoxime, perafensine, peralopride, peramivir, peraquisin, perastine, peratizole, perazine, perbufylline, perfomedil, perfosfamide, pegolide, perhexiline, periciazine, perifosine, perimetazine, perindopril, perindoprilat, perisoxal, perlapine, permethrin, perospirone, perphenazine, persilic acid, perzinfotel, petrichloral, pexantel, phanquone, phenacemide, phenacemide, phenacetin, phenactropinium, phenadoxone, phenaglycodol, phenamazoline, phenapromide, phenaphthazine, phenarsone, phenazocine, phenazopyridine, phenbutazone, phencarbamide, phencyclidine, phendimetrazine, phenelzine, pheneridine, phenethicillin, pheneturide, phenylglutarimide, phenicarbazide, phenindamine, phenindione, pheniprazine, pheniramine, phenisonone, phenmetrazine, phenobarbital, phenobutiodil, phenomorphan, phenothiazine, phenothrin, phenoxybenzamine, phenoxypropazine, phenprobamate, phenprocoumon, phenpromethamine, phensuximide, phentermine, phentolamine, phenyl aminosalicylic acid, phenylalanine, phenylbutazone, phenylephrine, phenylpropanolamine, phenylthiolone, phenyltoloxamine, phenyracillin, phenyramidol, phenyloin, pnetharbital, pholcodine, pholedrine, phoxim, phthalofyne, phthylsulfacetamide, phthalylsulfamethiazole, phthalylsulfathiazole, physostigmine, phytic acid, phytonadione, pibaxizine, pibecarb, piberaline, piboserod, pibrozelesin, pibutidien, picafibrate, picartamide, picenadol, picilorex, piclamilast, piclonidine, piclopastine, picloxydine, picobenzide, picodralazine, picolamine, piconol, picoperine, picoplatin, picoprazole, picotamide, picotrin, picumast, picumeterol, pidobenzone, pidolacetamol, pidolicaicd, pidotimod, pifarnine, pifinate, pifexole, piflutixol, piketoprofen, pildralazine, pilocarpine, pilsicainide, pimagedine, pimeclone, pimecrolimus, pimefylline, pimelautide, pimetacin, pimethixene, pimetine, imetremide, pimilprost, piminodine, pimobendan, pimonidazole, pimozide, pinacidil, pinadoline, pinafide, pinaverium, pinazepam, pincainide, pindolol, pinokalant, pinolcaine, pinoxepine, pioglitazone, pipacycline, pipamazine, pipamperone, pipazethate, pipebuzone, pipecuronium, pipemidicacid, pipendoxifene, pipenzolate, pipequaline, piperacetazine, piperacillin, piperamide, piperidolate, piperilate, piperocaine, piperonyl butoxide, piperoxan, piperphenidol, piperylone, pipobroman, pipoctanone, pipofezine, piposulfan, pipotiazine, pipoxizine, pipoxolan, pipradimadol, pipradrol, pipramadol, pipratecol, piprinhydrinate, pipocurarium, piprofurol, piprozolin, piquindone, piquizil, piracetam, pirandamine, pirarubicin, piraxelate, pirzmonam, pirazolac, pirbenicillin, pirbuterol, pirdonium, pirenoxine, pirenperone, pirezepine, pirepolol, piretanide, pirfenidone, pirbendil, piridicillin, piridocaine, piridoxilate, piridronic acid, pirifibrate, pirimiphos-ethyl, pirindazole, pirinixic acid, pirinixil, piriprost, piriqualone, pirisudanol, piritramide, piritrexin, pirlimycin, pirlindole, pirmagrel, pirmenol, pirnabine, piroctone, pirodavir, priodomast, pirogliride, piroheptine, pirolate, pirolazamide, piromidic acid, piroxantrone, piroxicam, piroxicillin, piroximone, pirozadil, pirprofen, pirquinozol, pirralkonium, pirsidomine, pirtenidine, pitenodil, pitofenone, pituxate, pivagabine, pivampicillin, pivenfrine, pivopril, pivoxazepam, pixantrone, pizotyline, plafbride, plaunotol, plauracin, pleconaril, pleuromulin, plevitrexed, plicamuycin, plomestane, pobilukast, podilfen, podofilox, poldine, polymixin, polythiazide, pomisartan, ponalrestat, ponazuril, ponfibrate, porfiromycin, posaconazole, posatirelin, posizolid, poskine, practolol, pradolfoxacin, prajmalium, pralatrexate, pralidoxime, pralmorelin, pralnacasan, pramipexole, pramiracetam, pramoxine, prampine, pranazepide, pranidipine, prankulast, pranolium, pranoprofen, pranosal, prasterone, prasugrel, pratosartan, pravadoline, pravastatin, praxadine, prazarelix, prazepam, prazepine, praziquantel, prazitone, prazocillin, prazosin, preclamol, prednazate, prednazoline, prednicarbate, prednimustine, prednisolamate, prednisolone, prednisone, prednival, prednylidene, pregabalin, pregnadiol, pregnenolone, premafloxacin, premazepam, prenalterol, prenisteine, prenoverine, prenoxdiazine, prenylamine, pretamazium, pretiadoil, prezatide, pribecaine, pridefine, prideperone, pridinol, prifelone, prifinium, prifuroline, pilocalne, primaperone, primaquine, primidolol, primidone, primycin, prinomastat, prinomide, prinoxodan, pristinol, pristinamycin, prizidilol, proadifen, probarbital, probenecid, probicromil, probucol, procainamide, procaine, procarbazine, procaterol, prochlorperazine, procinolol, procinonide, proclonol, procromil, procyclidine, procymate, prodeconium, prodilidine, prodipine, prodolic acid, profadol, profexalone, proflavine, proflazepam, progabide, progesterone, proglumetacin, proglumide, proheptazine, proligestone, praline, prolintane, prolonium, promazine, promegestone, promestriene, promethazine, promolate, promoxolane, prontalol, propacetamol, propafenone, propagermanium, propamidine, propanidid, propanocaine, propantheline, proparacaine, propatyl nitrate, propazolamide, propenidazole, proprntofylline, propenzolate, properidine, propetamide, propetamfos, propetandrol, propicillin, propikacin, propinetidine, propiomazine, propiocaine, propiram, propisergide, propiverine, propizepine, propofol, propoxate, propoxur, propoxycaine, propoxyphene, propranolol, propyl docetrizoate, propyl gallate, propylhexedrine, propyliodone, propylthiouracil, propyperone, propyphenazone, propyromazine, proquazone, proquinolate, prorenoate, proroxan, prscillardin, prospidium, prostalene, prosulpride, prosultiamine, proterguride, protheobromine, prothipendyl, prothixene, protiofate, protionamide, protirelin, protizinic acid, protokylol, protoporphyrin, protriptyline, proxole, proxibarbal, proxibutene, proxicromil, proxifezone, proxorphan, proxymetacaine, proxyphylline, prozapine, prucalopride, prulifloxacin, pruvanserin, pseudo ephedrine, pumafentrine, pumaprazole, pumitepa, pumosetrag, puromycin, pyrabrom, pyrantel, pyrathiazine, pyrazinamide, pyrazofurin, pyricarbate, pyridarone, pyridinol, pyridofylline, pyridostigmine, pyridoxal, pyridoxamine, pyridoxine, pyrilamine, pyrimethamine, pyrimate, pyrinoline, pyrithione, pyrithyldione, pyritidium, pyritinol, pyrophenindane, pyrovalerone, pyroxamine, pyrrobutamine, pyrrocaine, pyrrolifene, pyrroliphene, pyrrolnitrin, pyrroxane, pyrvinium, pytamine, quadazocine, quadrosilan, quatacaine, quazepam, quazinone, quazodine, quazolast, quetiapine, quifenadine, quiflapon, quillifoline, quilostigmine, quinacainol, quinacillin, quinacrine, quinagolide, quinaldine blue, quinapril, quinaprilat, quinazosin, quibolone, quincarbate, quindecamine, quindonium, quindoxin, quinelorane, quinestradol, quinestrol, quinethazone, quinetolate, quinezamide, quinfamide, quingestanol acetate, quingestrone, quinidine, quinine, quinotolast, quinpirole, quinterenol, quitiofos, quinuclium, quinupramine, quinupristin, quipazine, quisultazine, rabeprazole, raclopride, ractopamine, radafaxine, rafoxanide, ragaglitazar, ralitoline, raloxifene, raltitrexed, raluridine, ramatroban, ramciclane, ramelteon, ramifenazone, ramipril, ramiprilat, ramixotidine, ramnodigin, ramnoplanin, ramorelix, ramosetron, ranelic acid, ranimustine, ranimycin, ranirestat, ranitidine, ranolaine, rapacuronium, rasagiline, rasburicase, rathyronine, ravuconazole, razaxaban, razinodil, razobazam, razoxane, rebimastat, reboxetine, recainam, reclazepam, regadenoson, reglitazar, relcovaptan, relomycin, remacemide, remifentanil, remikiren, remiprostol, remoxipride, renanolone, rentiapril, renzapride, repaglinide, reparixin, repinotan, repirinast, repromicin, reproterol, rescimetol, rescinnamine, resequinil, reserpine, resiquimod, resocortol butyrate, resorantel, resorcinol, retapamulin, retelliptine, retigabine, retinol, revaprazan, revatropate, revenast, reviparin, revizinone, revospirone, ribavirin, riboflavin, riboprine, ribostamuycin, ricasetron, ridazolol, ridogrel, rifabutin, rifalazil, rifametane, rifamexil, rifamide, rifampin, rifapentine, rifaximin, rilapine, rilmakalim, rilmazafone, rilmenidine, rilopirox, rilozarone, rilpovorine, riluzole, rimantadine, rimazolium, rimcazole, rimexolone, rimiterol, rimonabant, rimoprogin, riodipine, rioprostil, ripazepam, ripisartan, risarestat, risedronicacid, risocaine, risotilide, rispenzepine, risperidone, ristianol, ristocetin, ritanserin, ritometan, ritipenem, ritobegron, ritodrine, ritolukast, ritonavir, ritropirronium, ritrosulfan, rivaroxaban, rivastigmine, rivoglitazone, rizatriptan, robalzotan, robenidine, rocastine, rocepafant, rociclovir, rocuronium, rodocaine, rodorubicin, rofecoxib, rofelodine, rofleponide, roflumilast, rogletimide, rokitamycin, rolafagrel, roletamide, rolgamidine, rolicyclidine, rolicyprine, rolipram, rolitetracycline, rolodine, rolziracetam, romazarit, romergoline, romifenone, romifidine, romurtide, ronactolol, ronidazole, ronifibrate, ronipamil, runnel, ropinirole, ropitoin, ropivacaine, ropizine, roquinimex, rosaprostol, rosaramicin, rose bengal, rosiglitazone, rosoxacin, rostafuroxin, rostaporfin, rosterolone, rosuvastatin, rotamicillin, rotigotine, rotoxamine, rotaxate, roxadimate, roxarsone, roxatidine acetate, roxibolone, roxifiban, roxindole, roxithromycin, roxolonium, roxoperone, rubitecan, ruboxistaurin, rufinamide, rufloxacin, rupatadine, rupintrivir, rutamycin, ruvazone, ruzadolane, sabarubicin, sabcomeline, sabeluzole, sabiporide, saccharin, safingol, safirinol, sagandipine, salacetamide, salafibrate, salantel, salazodine, salazosulfadimidine, salazosulfamide, salazosulfathiazole, salcaprozoic acid, salcolex, salethamide, salflucerine, salicyl alcohol, salicylamide, salicylic acid, salinazid, salinomycin, salmefamol, salmeterol, salmisteine, salnacedin, salprotoside, salsalate, sameridine, samixogrel, sampatrilat, sampirtine, sancycline, sanfetrinem, sanguinarium, saperconazole, saprisartan, sapropterin, saquinavir, sarafloxacin, sarakalim, saralasin, sarcolysin, sardomozide, saredutant, saripedem, sarizotan, sarmazenil, samoxicillin, sarpicillin, sarpogrelate, saterinone, satigrel, satranidazole, satraplatin, saviprazole, savoxepin, scopafungin, scopinast, scopolamine, secalciferol, seclazone, secnidazole, secobarbital, securinine, sedecamycin, sedoxantrone, seganserin, segesterone, seglitide, selamectin, selgiline, selfotel, soldenoson, selprazine, sampimod, sematilide, semaxanib, semduramicin, semorphone, semotiadil, semustine, senazodan, seocalcitol, sepazonium, seperidol, sepimostat, seprilose, seproxetine, sequifenadine, seratrodast, serazapine, serfibrate, sergolexole, sermetacin, sertindole, sertraline, setastine, setzindol, setipafant, setiptiline, setoperone, sevitropium, sevopramide, sezalamide, sagoside, sibenadet, sibopirdine, sibrafiban, sibutramine, siccanin, sifrprazine, siguazodan, silandrone, sildenafil, silibinin, silcristin, sildianin, silodosin, silodrate, silperisone, siltenzepine, simendan, simetride, simfibrate, simtrazene, simvastatin, sincalide, sinefungin, sinitrodil, sintropium, sipatrigine, siramesine, siratiazem, sirolimus, sisomicin, sitafloxacin, sitalidone, sitamaquine, sitaxentan, sitofibrate, sitoglusoide, sivelestat, soblidotin, sobuzoxane, solabegron, solifenasin, solimastat, solpecainol, solypertine, somatadine, soneclosan, sonepiprazole, sopitazine, sopromidine, soquinolol, sorafenib, soraprazan, sorbinicate, sorbinil, sorivudine, sornidipine, sotalol, soterenol, spaglumic acid, sparfloxacin, sparfosate, sparsomycin, sparteine, spectinomycin, spiclamine, spiperone, spiradoline, spiramide, spiramycin, spirapril, spiraprilat, spirendolol, spirgetine, spirilene, spiriprostil, spirofylline, spirogermanium, spiroglumide, spiromustine, spironolactone, spiroplatin, spirorenone, spirotriazine, spiroxasone, spiroxatrine, spiroxepin, spizofurone, sprodiamine, squalamine, squalane, stacofylline, stllimycin, stannsoprfin, stanolone, stanoaolol, stavudine, stearylsufamide, steffimycin, stenbolone, strpronin, stercuronium, stevaladil, stibamine, stibophen, stibamidine, stilbazium, stilonium, strimazole, stiripentol, stirocainide, stirofos, streptomycin, streptonicozid, streptonigrin, streptozocin, styramine, subathiazone, subendazole, succinylcholine, succinylsulfathiazole, succisulfone, suclofenide, sucralfate, sucralose, sucrose octaacetate, sucrosufate, sudexanox, sudoxicam, sufenatil, sufotidine, sufugolix, sugammadex, sulamserod, sulazepam, sulazuril, sulbactam, sulbenicillin, sulbenox, sulbentine, sulbutiamine, sulclamine, sulconazole, sulfabenz, sulfabenzamide, sulfabromomethazine, sulfacarbamide, sulfacecole, sulfacetamide, sulfachlorpyridazine, sulfachrysoidine, sulfaclomide, sulfaclorazole, sulfaclozine, sulfacytine, sulfadiazine, sulfadimethoxine, sulfadoxine, sulfaethidole, sulfaguanidine, sulfaguanole, sulfalene, sulfaloxic acid, sulfamazone, sulfamerazine, sulfameter, sulfamethaziine, sulfamethizole, sulfamethoxazole, sulfamethoxypyridazine, sulfametmidine, sulfametrole, sulfamonomethoxine, sulfamoxole, sulfanilamide, sulfanilate, sulfaanitran, sulfaperin, sulfaphenazole, sulfaproxyline, sulfapyridine, sulfaquinoxaline, sulfarsphenamine, sulfasalazine, sulfasomizole, sulfasuccinamide, sulfasymazine, sulfathiazole, sulfathiourea, sulfatolamide, sulfatroxazole, sulfatrozole, sulfazamet, sulfinaolol, sulfinpyrazone, sulfiram, sulfisomidine, sulfisoxazole, sulfobromophthalein, sulfonterol, sulforidazine, sulfosalicylic acid, sulfoxone, sulcrinat, sulindac, sulisatin, sulisobenzone, sulmarin, sulmazole, sulmepride, sulnidazole, sulocarbilate, suloctidil, sulodexide, sulofenur, sulopenem, sulosemide, sulotroban, suloxifen, sulpiride, sulprosal, sulprostone, sultamicillin, sultiame, sultopride, sultosilic acid, sultroponium, sulukast, sulverapride, sumacetamol, sumanirole, sumarotene, sumatriptan, sumetizide, sunagrel, suncillin, sunepitron, supidimide, supalast, suproclone, suprofen, suramin, suricainide, suriclone, suritozole, suronacrine, susalimod, suxemerid, suxethonium, suxibuzone, symclosene, synetine, tabilautide, tabimorelin, tacalcitol, tacapenem, tacedinaline, taclamine, tacrine, tacrolimus, tadalafil, tafluposide, taglutamine, tagorizine, talampanel, talampicillin, talaporfin, talastine, talbutal, taleranol, talibegron, talinolol, talipexole, talisomycin, tallimustine, talmetacin, talmetoprim, talnetant, talniflumate, talopram, talsalate, toloximine, talsaclidine, talsupram, taltirelin, taltobulin, taltrimide, taludipine, talviraline, tameridone, tameticillin, tametraline, tamibarotene, tamitinol, tanolarizine, tamoxifen, tampramine, tamsulosin, tanaproget, tandamine, tandospirone, tandutinib, taniplon, tanomastat, tapentadol, taprizosin, taprostene, tarazepide, tariquindar, tasosartan, tasuldine, taurolidine, tauromustine, tauroselcholic acid, taurosterone, tazadolene, tazanolast, tazarotene, tazasubrate, tazeprofen, tazifylline, taziprinone, tazobactam, tazofelone, tazolol, tazometine, tebanicline, tebatizole, tebipenem, tebufelone, tebuquine, tecadenoson, tecalcet, tecastemizole, teclthiazide, teclozan, tedisamil, tefazoline, tefenperate, teflufazine, teflutixol, tegafur, tegaserod, teglicar, teicopanin, telavancin, telbivudine, telenzepine, telinavir, telithromycin, telmesteine, telmisartan, teloxantrone, teludipine, temafloxacin, temarotene, tematropium, temazepam, temefos, temelastine, temiverine, temocapril, temocaprilat, temocillin, temodox, temoporfin, temozolomide, temisirolimus, temurtide, tenamfetamine, tenatoprazole, tendamistat, tenidap, tenilapine, teniloxazine, tenilsetam, teniposide, tenivastatin, tenocyclidine, tenofovir, tenofovir disoproxil, tenonitrozole, tenosal, tenosiprol, tenoxicam, tenylidone, teoprantil, teoprolol, tepirindole, tepoxalin, teprenone, teprotide, terazosin, terbequinil, terbinafine, terbogrel, terbucromil, terbufirol, terbuficin, terbuprol, terbutaline, terciprazine, terconazole, terdecamycin, teerestigmine, terfeadine, terflavoxate, terfluranol, terguride, teriflunomide, terikalant, terizidone, terlakiren, terlipressin, temidazole, terodiline, terofenamate, teroxalene, teroxirone, tertatolol, tesaglitazar, tesicam, tesimide, tesimilifene, tesofensine, testolactone, testosterone, tetomilst, tetrabarbital, tetrabenazine, tetracaine, tetracycline, tetrahydrozoline, tetramethrin, tetramisole, tetraxetan, tetrazepam, tetrazolast, tetriprofen, tetrofosmin, tetronasin, tetroquinone, tetroxoprin, tetrydamine, teverelix, texacromil, tezacitabine, tezosentan, thalidomide, thebacon, thenalidine, thenium, thenyldiamine, theobromine, theodrenaline, theofibrate, theophylline, thiabendazole, thiacetarsamide, thialbarbital, thiamazole, thiamine, thiamiprine, thiamphenicol, thamylal, thiazesim, thiazinamium, thiazolsulfone, thiethyperazine, thihexinol ethylbromide, thimerfonate, thimerosal, thiocolchicoside, thioctic acid, thiofuradene, thioguanine, thiohexamide, thioinosine, thiopental, thiophanate, thiopropazate, thioproperazine, thioridazine, thiosalan, thiostrpton, thiotepa, thiotetrabarbital, thiothixene, thiphenamil, thiphencillin, thiram, thonzonium, thonzylamine, thozalinone, threonine, thymocartin, thymoctonan, thymol, thymopentin, thymotrinan, thyromedan, thyropropic acid, thyroxin, tiacrilast, tiadenol, tiafibrate, tiagabine, tiamenidine, tiametomnium, tiamulin, tianafac, tianeptine, tiapamil, tiapirinol, tiapride, tiaprofenic acid, tiaprost, tiaramide, tiazofurin, tiazuril, tiabalosin, tibeglisene, tibenelast, tibenzate, tibezonium, tibolone, tibric acid, tibrofan, ticabesine, ticalopride, ticarbodine, ticarcillin, ticlatone, ticlopidine, ticolubant, ticrynafen, tidembersat, tidiacic acid, tiemonium, tienocarbine, tienopramine, tienoxolol, tifemoxone, tifenazoxide, tiflamizole, tiflorex, tifluadom, tiflucarbine, tiformin, tifurac, tigecycline, tigemonam, tigestol, tigloidine, tilargenine, tiletamine, tilidine, tiliquinol, tilisolol, tilmacoxib, tilmicosin, tilnoprofen, tilomisole, tilorone, tilozepine, tilsuprost, tiludonic acid, timcodar, timefurone, timegadine, timelotem, timepidium, timiperone, timirdine, timobesone acetate, timofibrate, timolol, timonacic, timoprazole, tinabinol, tinazoline, tinidazole, tinisulpride, tinofedrine, tinoridine, tiocarlide, tioclomarol, tioconazole, tioctilate, tiodazosin, tiodonium, tiomergine, tiomesterone, tioperidone, tiopinate, tiopronin, tiopropamine, tiospirone, tiotidine, tiotropium, tioxacin, tioxamast, tioxaprofen, tioxidazole, tioxolone, tipentosin, tipepidine, tipetropium, tipifarnib, tipindole, tipranavir, tipredane, tiprenolol, tiprinast, tiprodil, tiprostanide, tiportimod, tiqueside, tiquinamide, tiquizium, tiracizine, tirapazamine, tiratricol, tirilazad, tirofiban, tiropramine, tisartan, tisocalcitate, tisocromide, tisopurine, tisoquone, tivanidazole, tiviciclovir, tivirapine, tixadil, tixanox, tixocortol, tizabrin, tizanidine, tizolemide, tizoprolic acid, tobicillin, toborinone, tobramycin, tocainide, tocamphyl, tocladesine, tocofenoxate, tocofibrate, tocophersolan, todralazine, tofenacin, tofetridine, toflmilast, toflsoline, tofisppam, tolafentrine, tolamolol, tolazamide, tolboxane, tolbutamide, tolvapone, tolciclate, toldimfos, tolfamide, tolfenamic acid, tolgabide, tolimidone, tolindate, toliodium, toliprolol, tolmesoxide, tometin, tolnaftate, tolnapersine, tolnidamine, toloconium, tolonidine, tolonium, toloxatone, toloxychlorinol, tolpadol, tolpentamide, tolperisone, tolpiprazole, tolpronine, tolpropamide, tolpyrramide, tolquinzole, tolrestat, tolterodine, toltrazuril, tolufazepam, tolvaptan, tolycaine, tomeglovir, tomelukast, tomoglumide, tomoxiprole, tonabersat, tonazocine, topilutamide, topiramate, topixantrone, topotecan, toprilidine, topterone, toquizine, torbafylline, torcetrapib, torcitabine, toremifene, toripristone, torsemide, tosagestin, tosifen, tosufloxacin, tosulur, trabectedin, traboxopine, tracazolate, tradecamide, tralonide, tramadol, tramazoline, trandolapril, trandolaprilat, tranexamic acid, tranilast, transcainide, trantelinium, tranycypromine, trapencaine, trapidil, travoprost, traxanox, traxoprodil, trazitiline, trazium, trazodone, trazolopride, trebenzomine, trecadrine, trecetilide, trefentanil, trelnarizine, treloxinate, trenbolone, trengestone, trenizine, treosulfan, trepibutone, trepipam, trepirium, treprostinil, treptilamine, terquisin, tresperimus, trestolone, trethinium, trethocanoic acid, tretinoin, tretinoin tocoferil, tretoquinol, triacetin, triafungin, triamcinolone, triamcinolone acetonide, triamcinolone benetonide, triamcinolone furetonide, triampyzine, triamternem triaziquone, triazolam, tribendilol, tribenoside, tribromsalan, tribuzone, tricaprilin, tricetamide, trichlorfon, trichlormethiazide, trichlomethine, triciribine, triclabendazole, triclacetamol, triclazate, triclobisonium, triclocarban, triclodazol, triclofenol, triclofos, triclofyllin, triclonide, triclosan, tricyclamol, tridihexethyl, tridolgosir, trientine, triethylenemelamine, trifenagrel, trifezolac, triflocin, triflubazam, triflumidate, triflomeprazine, trifluperazine, trifluperidol, triflupromazine, trifluidine, triflusal, trifosmin, trigevolol, trihexylpheidyl, triletide, trilostane, trimazosin, trimebutine, trimecain, trimedoxime, trimegestone, trimeperidine, trimeprazine, trimetazidine, trimethadone, trimethamide, trimethaphan, trimethidinium, trimethobenzamide, trimethoprim, trimetozine, trimetrexate, trimexiline, trimipramine, trimoprostil, trimoxamine, trioxifene, trioxsalen, tripalmitin, tripamide, triparanol, tripelennamine, triplatin, triprolidine, triptorelin, tritoqualine, trixolane, trizoxime, trocimine, troclosene, trodusquemine, trofosfamide, troglitazone, troleandomycin, tromanttadine, tropabazate, tropanserin, tropapride, tropatepine, tropenziline, tropicamide, tropigline, tropirine, tropisetron, tropodifene, troquidazole, trospectomycin, trospium, trovafloxacin, trovirdine, troxacitabine, troxerutin, troxipide, troxolamide, troxonium, troxypyrrolium, truxicurium, truxipicurium, tryparsamide, tubocurarine, tubulozole, tucaresol, tuclazepam, tulathromycin, tulobuterol, tulopafant, turosteride, tuvatidine, tybamate, tylosin, tymazolin, tyropanoate, tyrosine, tyrothricin, ubenimex, ubidecarenone, ubisindine, ufenamate, ufiprazole, uldazepam, ulifloxacin, uliprisnil, umespirone, undecylenic acid, unoprostone, upenazime, upidosin, uracil, uracil mustard, urapidil, uredepa, uredofos, ureflbrate, ursodiol, urulcholic acid, utibapril, utibaprilat, vadocaine, valaciclovir, valconazole, valdecoxib, valdetamide, valdipromide, valethamate, vlaganiciclovir, valine, valnemulin, vlanoctamide, valofane, valomaciclovir, valperinol, valproate, vlaproicacid, valpromide, valrocemide, valrubicin, valsartan, valorcitabine, valtrate, vamicamide, vancomycin, vandetanib, vaneprim, vanitiolide, vanoxerine, vanyldisulfamide, vapiprost, vapreotide, vardenfanil, varenicline, varespladib, vatalanib, vatanidipine, vebufloxacin, vecuronium, vedaclidine, vedaprofen, velaresol, velnacrine, venlafaxine, venritidine, verodoline, veralipride, verapamil, verazide, verilopam, verlukast, verofylline, versetamide, verteporfin, vesnarinone, vestipitant, vetrabutine, vidarabine, vigabatrin, vilazodone, vildaglipin, viloxazine, vinbarbital, vinblastine, vinburnine, vincamine, vincanol, vincofos, vinconate, vincristine, vindeburnol, vindesine, vinpidine, vinflunine, vinformide, vinfosiltine, vinglycinate, vinleucinol, vinleurosine, vinmegallate, vinorelbine, vinpocetine, vinpoline, vinrosidine, vintiamol, vintoperol, vintriptol, vinylbital, vinzolidine, viomycin, viprostol, viqualine, viquidil, virginiamycin, viridofulvin, viroxime, visnadine, visnafylline, vofopitant, voglibose, volazocine, volpristin, voriconazole, vorozole, voxergolide, xaliproden, xamoterol, xanomeline, xanoxic acid, xanthinol, xantifibrate, xantocillin, xantofyl palmitate, xemilofiban, xenalipin, xenazoic acid, xenbucin, xenipentone, xenothiorate, xenygloxal, xenylhexenicacid, xenylropium, xibenolol, xibornol, xidecaflur, xilobam, ximelagatran, ximoprofen, xinidamine, xinomiline, sipamide, xipranolol, xorphanol, xylamidine, xylazine, xylocoumarol, xylometazoline, xyloxemine, yohimbic acid, zabicipril, zabiciprilat, zacopride, zafirlukast, zafuleptine, zalcitabine, zalderide, zaleplon, zalospirone, zalitidine, zaltoprofen, zamifenacin, zanamivir, zanapezil, zankiren, zanoterone, zapizolam, zaprinast, zardaverine, zatebradine, zatosetron, zelandopam, zenarestat, zenazocine, zeniplatin, zepastine, zeranol, zetidoline, zidapamide, zidometacin, zidovudine, zifrostilone, zilantel, zilascorb, zileuton, zilpaterol, zimeldine, zimiidoben, zindotrine, zindoxifene, zinconazole, zinostatin, zinterol, zinviroxime, zipeprol, ziprsidone, zocainone, zofenopril, zofenoprilat, zoficonazole, zolamine, zolasartan, zolazepam, zolendronic acid, zolenzepine, zolertine, zolimidine, zoliprofen, zolmitriptan, zoloperone, zolpidem, zomebazam, zomepirac, zometapine, zonampanel, zoniclezole, zoniporide, zonisamide, zopiclone, zopolrestat, zorbamycin, zorubicin, zosuquidar, zotepine, zoticasone, zoxazolamine, zucapsaicin, zuclomiphene, zuclopenthixol, zylofuramine, or a combination comprising at least one of the foregoing biologically active agents.

* * * * *